(12) United States Patent
Hartmann et al.

(10) Patent No.: US 9,271,963 B2
(45) Date of Patent: Mar. 1, 2016

(54) SELECTIVE INHIBITORS OF HUMAN CORTICOSTEROID SYNTHASES

(75) Inventors: Rolf Hartmann, Saarbrücken (DE); Marieke Voets, Herent (BE); Ursula Müller-Vieira, Saarbrücken (DE)

(73) Assignee: UNIVERSITAT DES SAARLANDES, Saarbrucken (DE)

( * ) Notice: Subject to any disclaimer, the term of this patent is extended or adjusted under 35 U.S.C. 154(b) by 1510 days.

(21) Appl. No.: 11/885,605

(22) PCT Filed: Mar. 2, 2006

(86) PCT No.: PCT/EP2006/060410
§ 371 (c)(1),
(2), (4) Date: Oct. 29, 2008

(87) PCT Pub. No.: WO2006/092430
PCT Pub. Date: Sep. 8, 2006

(65) Prior Publication Data
US 2009/0221591 A1    Sep. 3, 2009

(30) Foreign Application Priority Data

Mar. 3, 2005    (DE) .................. 10 2005 009 705
Jun. 24, 2005    (DE) .................. 10 2005 029 372

(51) Int. Cl.
| | |
|---|---|
| *C07D 213/16* | (2006.01) |
| *C07D 213/24* | (2006.01) |
| *C07D 213/30* | (2006.01) |
| *C07D 233/54* | (2006.01) |
| *C07D 233/56* | (2006.01) |
| *C07D 233/64* | (2006.01) |
| *C07D 239/26* | (2006.01) |
| *C07D 239/30* | (2006.01) |
| *C07D 239/34* | (2006.01) |
| *C07D 263/32* | (2006.01) |
| *A61K 31/4164* | (2006.01) |
| *A61K 31/4406* | (2006.01) |
| *A61K 31/4709* | (2006.01) |
| *A61K 31/505* | (2006.01) |
| *C07D 213/55* | (2006.01) |
| *C07D 213/56* | (2006.01) |
| *C07D 213/57* | (2006.01) |

(52) U.S. Cl.
CPC ......... *A61K 31/4164* (2013.01); *A61K 31/4406* (2013.01); *A61K 31/4709* (2013.01); *A61K 31/505* (2013.01); *C07D 213/16* (2013.01); *C07D 213/30* (2013.01); *C07D 213/55* (2013.01); *C07D 213/56* (2013.01); *C07D 213/57* (2013.01); *C07D 233/54* (2013.01); *C07D 233/56* (2013.01); *C07D 233/64* (2013.01); *C07D 239/26* (2013.01); *C07D 239/30* (2013.01); *C07D 239/34* (2013.01); *C07D 263/32* (2013.01)

(58) Field of Classification Search
None
See application file for complete search history.

(56) References Cited

U.S. PATENT DOCUMENTS

| | | | |
|---|---|---|---|
| 3,098,077 A | | 7/1963 | Allen |
| 3,118,895 A | | 1/1964 | Allen |
| 3,165,525 A | | 1/1965 | Bencze |
| 3,541,109 A | | 11/1970 | Kauer |
| 4,510,149 A | | 4/1985 | Cozzi et al. |
| 4,585,575 A | * | 4/1986 | Sugimori et al. ........ 252/299.61 |
| 5,480,883 A | * | 1/1996 | Spada et al. .................. 514/249 |
| 5,656,643 A | | 8/1997 | Spada et al. |
| 6,150,347 A | | 11/2000 | Weber |
| 6,608,047 B2 | | 8/2003 | MacLaughlan et al. |
| 2002/0013303 A1 | | 1/2002 | Weber |
| 2002/0123485 A1 | | 9/2002 | Alexander et al. |
| 2003/0220310 A1 | | 11/2003 | Schuh |
| 2003/0220312 A1 | | 11/2003 | Schuh |
| 2004/0092521 A1 | * | 5/2004 | Altenbach et al. ............ 514/243 |

FOREIGN PATENT DOCUMENTS

| | | | |
|---|---|---|---|
| DE | 34 20 592 A1 | | 12/1984 |
| JP | 07-165717 A | * | 6/1995 |
| WO | WO 91/17987 A | | 11/1991 |
| WO | WO 92/11240 A | | 7/1992 |
| WO | WO 93/10114 | * | 5/1993 |
| WO | WO 96/40255 | | 12/1996 |
| WO | WO 00/31036 A1 | | 6/2000 |
| WO | WO 01/34132 A2 | | 5/2001 |
| WO | WO 01/76574 A2 | | 10/2001 |
| WO | WO 03/051805 A2 | | 6/2003 |
| WO | WO 2004/046145 A1 | | 6/2004 |

OTHER PUBLICATIONS

Lin et al. Bioorganic & Medicinal Chemistry Letters, 2001, vol. 11, pp. 631-633.*
Muller-Vieira et al. Journal of Steroid Biochemistry & Molecular Biology, Aug. 2005, vol. 96, pp. 259-270.*
English Translation of JP 07-165717 A (Jun. 1995).*
Pivsa-Art et al. Bulletin of the Chemical Society of Japan, 1998, 71(2), 467-473 (Abstract/HCAPLUS Entry Attached).*
Higashii et al. (JP 07233109; Published Sep. 5, 1995) (HCAPLUS Accession No. 1996:56085, Document No. 124:87031) (English Abstract/Hcaplus Entry Attached).*

(Continued)

*Primary Examiner* — James D Anderson
(74) *Attorney, Agent, or Firm* — Ballard Spahr LLP

(57) ABSTRACT

The invention relates to compounds for selectively inhibiting human corticosteroid synthases CYP1 1 B1 and CYP1 1 B2, and to the production and use thereof for treating hypercortisolism, diabetes mellitus, hyperaldosteronism, cardiac insufficiency, myocardial fibrosis, depression, age-related cognitive decline and metabolic syndrome.

25 Claims, 1 Drawing Sheet

(56) References Cited

OTHER PUBLICATIONS

Higashii et al. (JP 07206715; Published Aug. 8, 1995) (HCAPLUS Accession No. 1995:969546, Document No. 124:8841) (English Abstract/HCAPLUS Entry Attached).*

Sanchez-Viesca et al. (Revista Latinamericana de Quimica, 1985, vol. 16, Nos. 2-3, pp. 91-94) (HCAPLUS Accession No. 1986:497380, Document No. 105:97380) (English Abstract/HCAPLUS Entry Attached).*

Agarwal et al., "Antimineralocorticoids," Renal Physiol. Biochem., 14: 217-223 (1991).

Alberts et al., "Selective Inhibition of 11β-hydroxysteroid Dehydrogenase Type 1 Decreases Blood Glucose Concentrations in Hyperglycaemic Mice," Diabetologica, 45:1528-1532 (2002).

Bencze et al., "Adrenal Cortical Inhibitors and Potent Synthetic Estrogens," J. Med. Pharm. Chem., 8:213-214 (1965).

Bencze et al., "Selective Adrenal Cortical and Gonadal Inhibitors," J. Med. Pharm. Chem., 5:1298-1306 (1962).

Bhatnagar et al., "Highly Selective Inhibition of Estrogen Biosynthesis by CGS 20267, a New Non-Steroidal Aromatase Inhibitor," J. Steroid Biochem. Mol. Biol., 37(6):1021-1027 (1990).

Bolli et al., "The Dawn Phenomenon"—A Common Occurrence in Both Non-Insulin-Dependent and Insulin-Dependent Diabetes Mellitus, N. Engl. J. Med., 310:746-750 (1984).

Brilla, "Aldosterone and Myocardial Fibrosis in Heart Failure," Herz, 25(3):299-306 (2000).

Brilla, "Renin-Angiotensin-Aldosterone System and Myocardial Fibrosis," Cardiovascular Research, 47:1-3 (2000).

Chowdhury et al., "Palladium Catalyzed Cross-Coupling Between Phenyl- or Naphthylboronic Acids and Benzylic Bromides," Tetrahedron Letters, 40(43):7599-7603 (1999).

Coates et al., "New Therapeutic Agents of the Quinoline Series. Introduction and I. Monopyridylquinolines," J. of Chem. Society, M19:401-404 (1944).

Cozzi et al., "N-Imidazolyl Derivatives of the Napththalene and Chroman Rings as Thromboxane $A_2$ Synthase Inhibitors," Eur. J. Med. Chem., 26:423-433 (1991).

DeFronzo, Pathogenesis of Type 2 Diabetes: Metabolic and Molecular Implications for Identifying Diabetes Genes, Diabetes Reviews, 5(3):177-269 (1997).

Demers et al., "The Effects of CGS 16949A, an Aromatase Inhibitor on Adrenal Mineralocorticoid Biosynthesis," J. Clinical Endocrinology and Metabolism, 70(4):1162-1166 (1990).

Denner et al., "Cloning and Stable Expression of the Human Mitochondrial Cytochrome P45011B1 cDNA in V79 Chinese Hamster Cells and Their Application for Testing of Potential Inhibitors," Pharmacogenetics, 5:89-96 (1995).

Dowsett et al., "Potency and Selectivity of the Non-Steroidal Aromatase Inhibitor CGS 16949A in Postmenopausal Breast Cancer Patients," Clinical Endocrinology, 32:623-634 (1990).

Dumouchel et al., "Synthesis and Reactivity of Lithium Tri(quinolinyl)magnesates," Tetrahedron, 59:8629-8640 (2003).

Ehmer et al., "Development of a Test System for Inhibitors of Human Aldosterone Synthase (CYPI1B2): Screening in Fission Yeast and Evaluation of Selectivity in V79 Cells," J. Steroid Biochemistry & Molecular Biology, 81:173-179 (2002).

Ehmer et al., "Development of a Simple and Rapid Assay for the Evaluation of Inhibitors of Human 17α-hydroxylase-$C_{17,20}$-lyase (P450c17) by Coexpression of P450c17 with NADPH-Cytochrome-P450-Reductase in Escherichia coli," J. Steroid Biochemistry & Molecular Biology, 75:57-63 (2000).

Foster et al., "Analogues of Aminoglutethimide: Selective Inhibition of Colesterol Side-Chain Cleavage," J. Med Chem, 26:50-54 (1983).

Fürstner et al., "Iron-Catalyzed Cross-Coupling Reactions," JACS, 124(46):13856-13863 (2002).

Furukawa et al., "Preparation of Pyridyl Grignard Reagents and Cross Coupling Reactions with Sulfoxides Bearing Azaheterocycles," Tetrahedron Letters, 28(47):5845-5848 (1987).

Gazdar et al., "Establishment and Characterization of a Human Adrenocortical Carcinoma Cell Line that Expresses Multiple Pathways of Steroid Biosynthesis," Cancer Research, 50:5488-5496 (1990).

Graves et al., "Stereoselective Inhibition of Aromatase by Enantiomers of Aminoglutethimide," Endocrinology, 105(1):52-57 (1979).

Hartmann et al., "Discovery of Selective CYP11B2 (aldosterone synthase) Inhibitors for the Therapy of Congestive Heart Faiulre and Myocardial Fibrosis," Eur. J. Med. Chem., 38(4):363-366 (2003).

Hartmann et al., "Synthesis and Evaluation of Azole-Substituted Tetrahydronaphthalenes as Inhibitors of P450 AROM, P450 17, and P450 TXA2," Arch. Pharm. Pharm. Med., 339:251-261 (1996).

Hartmann et al., "Aromatase Inhibitors. Synthesis and Evaluation of Mammary Tumor Inhibiting Activity of 3-Alkylated 3-(4-Aminophenyl)piperidine-2,6-diones," J. Med. Chem., 29:1362-1369 (1986).

Häusler et al., "Evidence that Corticosterone is not an Obligatory Intermediate in Aldosterone Biosynthesis in the Rat Adrenal," J. Steroid Biochem., 34(1-6):567-570 (1989).

Heffelfinger et al., "Glucocorticoid Effects on Memory Function over the Human Life Span," Development and Psychopathology, 13:491-513 (2001).

Hey et al., "New Therapeutic Agents of the Quinoline Series. Part VII. 2-3-, and 4-Pyridylquinolines, 4-Pyridylquinaldines, and 2-Pyridyl lepidines," J. Chem. Soc. 1678-1683 (1950).

Hutschenreuter et al., "Synthesis of Hydroxy Derivatives of Highly Potent Non-Steroidal CYP 17 Inhibitors as Potential metabolites and Evaluation of their Activity by a Non Cellular Assay Using Recombinant Human Enzyme," J. Enzyme Inhibition and Medicinal Chemistry, 19(1):17-32 (2004).

Jacobs et al.,"1-Imidazolyl(alkyl)-Substituted Di- and Tetrahydroquinolines and Analogues: Syntheses and Evaluation of Dual Inhibitors of Thromboxane $A_2$ Synthase and Aromatase," J. Med. Chem., 43:1841-1851 (2000).

Jagdmann et al., "A Mild Efficient Procedure for the Conversion of Carboxylic Acid Esters to Primary Amides Using Formamide/Methanolic Sodium Methoxide," Synthetic Comm., 20(8):1203-1208 (1990).

Johnson et al., "The Synthesis of 1 Arylimidazoles, a New Class of Steroid Hydroxylation Inhibitors," Journal of Medicinal Chemistry, 12(6):1024-1028 (1969).

Kawamoto et al., "Role of Steroid 11β-Hydroxylase and Steroid 18-Hydroxylase in the Biosynthesis of Glucocorticoids and Mineralocorticoids in Humans," Proc. Natl. Acad. Sci. USA, 89:1458-1462 (1992).

Kelley et al., "Syntheses and Photophysical Properties of Some 4-Arylpyridinium Salts," Journal Het. Chem., 38(11):11-23 (2001).

Kulbertus, "Clinical Study of the month. The RALES study (randomized aldactone evaluation study)," Rev. Med. Liege, 54:770-772 (1999).

Lam et al., "New Aryl/Heteroaryl C-N Bond Cross-Coupling Reactions via Arylboronic Acid/Cupric Acetate of Arylation," Tetrahedron Letters, 29:2941-2944 (1998).

Lan et al., "A Simple Copper Salt Catalysed the Coupling of Imidazole with Arylboronic Acids in Protic Solvent," Chem. Communication, 188-189 (2004).

Lijnen et al., "Induction of Cardiac Fibrosis by Aldosterone," J. Mol. Cell. Cardiol., 32:865-879 (2000).

Losert et al., "Mespirenone and Other 15,16-Methylene-17-spirolactones, a New Type of Steroidal Aldosterone Antagonists," Drug Res., 36:1583-1600 (1986).

Lowry et al., "Protein Measurement With the Folin Phenol Reagent," J. Biol. Chem., 193:265-275 (1951).

MacFadyen et al., "Aldosterone Blockade Reduces Vascular Collagen Turnover, Improves Heart Rate Variability and Reduces Early Morning Rise in Heart Rate in Heart Failure Paitents," Cardiovascular Research, 35:30-34 (1997).

Maguire et al., "A New Series of PDGF Receptor Tyrosine Kinase Inhibitors: 3-substituted Quinoline Derivatives," Journal of Medicinal Chemistry, 37:2129-2137 (1994).

Mornet et al., "Characterization of Two Genes Encoding Human Steroid 11β-Hydroxylase (P-$405_{11B}$)," J. Biological Chemistry, 264(35):20961-20967 (1989).

Nickisch et al., "Aldosterone Antagonists. 2. New 7α-(Acetylthio)-1'5,16-methylene Spirolactones," J. Med. Chem., 30(8):1403-1409 (1987).

(56) References Cited

OTHER PUBLICATIONS

Nickisch et al., "Aldosterone Antagonists. 4. Synthesis and Activities of Steroidal 6,6-Ethylene-15,16-Methylene 17-Spirolactones," *J. Med. Chem.*, 34:2464-2468 (1991).
Nieman, "Medical Therapy of Cushing's Diseases," *Pituitary*, 5:77-82 (2002).
Phillips et al., "Elevated Plasma Cortisol Concentrations: A Link Between Low Birth Weight and the Insulin Resistance Syndrome?" *J. Clin. Endocrinol. Metab.*, 83(3):757-760 (1998).
Pigini et al., "Imidazoline Receptors: Qualitative Structure-Activity Relationships and Discovery of Tracizoline and Benazoline. Two Ligands with High Affinity and Unprecedented Selectivity," *Bioorganic & Med. Chem.*, 5(5):833-841 (1997).
Pitt et al., "Eplerenone, a Selective Aldosterone Blocker, in Patients with Left Ventricular Dysfunction after Myocardial Infarction," *New Engl. J. Med.*, 348:1309-1321 (2003).
Pitt et al., "The Effect of Spironolactone on Morbidity and Mortality in Patients with Severe Heart Failure," *New Engl. J. Med.*, 341(10):709-717 (1999).
Raman et al., "Studies on Aldosterone Biosynthesis in Vitro," *Biochemistry*, 5(6):1795-1804 (1966).
Santen et al., "Specificty of Low Dose Fadrozole Hydrochloride (CGS 16949A) as an Aromatase Inhibitor," *Journal of Clinical Endocrinology and Metabol.*, 73(1):99-106 (1991).
Shapiro et al., "Nocturnal Elevation of Glucose Levels during Fasting in Noninsulin-Dependent Diabetes," *Journal of Clinical Endocrinol. and Metab.*, 72(2):444-454 (1991).
Soberman et al., Spironolactone in Congestive Heart Failure, *Current Hypertension Reports*, 2:451-456 (2000).
Stewart et al., "11β-Hydroxysteroid Dehydrogenase," *Vitamin and Hormones*, 57:249-324 (1999).
Taymans et al., "Human CYP11B2 (Aldosterone Synthase) Maps to Chromosome 8q24.3," *J. Clin. Endocrinol. and Metab.*, 83(3):1033-1036 (1998).
Temple et al., "Inhibitors of Adrenal Steroid Biosynthesis," *Annual Review of Pharmacology*, 10(VII):199-218 (1970).
Thompson et al., "Utilization of Oxygen and Reduced Nicotinamide Adenine Dinucleotide Phosphate by Human Placental Microsomes during Aromatization of Androstenedione," *J. Biol. Chem.*, 249(17):5364-5372 (1974).
Ulmschneider et al., "Development and Evaluation of a Pharmacophore Model for Inhibitors of Aldosterone Synthase (CYP11B2)," *Bioorganic & Med. Chem. Let.*, 16(1):25-30 (2006).
Ulmschneider et al., "Synthesis and Evaluation of Imidazolylmethylenetetrahydronaphthalenes and Imidazolylmethyleneindanes: Potent Inhibitors of Aldosterone Synthase," *J. Med. Chem.*, 48(6):1796-1805 (2005).
Voets et al., "Synthesis and Evaluation of Heteroaryl-Substituted Dihydronaphthalenese and Indenes: Potent and Selective Inhibitors of Aldosterone Synthase (CYP11B2) for the Treatment of Congestive Heart Failure and Myocardial Fibrosis," *J. Med. Chem.*, 49(7):2222-2231 (2006).
Voets et al., "Heteroaryl-Substituted Naphthalenes and Structurally Modified Derivatives: Selective Inhibitors of CYP11B2 for the Treatment of Congestive Heart Failure and Myocardial Fibrosis," *J. Med. Chem.*, 48(21):6632-6642 (2005).
Weber et al., "Pathological Hypertrophy and Cardiac Interstitium," *Circulation*, 83:1849-1865 (1991).
Weindel et al., "Inhibitory Effects of the Novel Anti-aldosterone Compound Mespirenone on Adrenocortical Steroidogenesis in vitro," *Arzneimittel Forschung Drug Research*, 41(II):946-949 (1991).
Young et al., "Aldosterone and the Heart," *Trends Endocrinol. Metab.*, 11(6):224-226 (2000).
Young et al., "Halogen Reactivites. Certain Heterocyclic Iminohalide Systems," *JACS*, 4773-4775 (1951).
Zannad et al., "How Early Should Eplerenone be Initiated in Acute Myocardial Infarction Complicated by Heart Failure? An Analysis of Early vs. Late Initiation in the Ephesus Trial," *Eplerenone's Heart Failure Efficacy and Survival Study*, Presentation No. 404-9 (2003).

* cited by examiner

SELECTIVE INHIBITORS OF HUMAN CORTICOSTEROID SYNTHASES

CROSS-REFERENCE TO RELATED APPLICATIONS

The present application is a National Phase Application of International Application No. PCT/EP2006/060410, filed Mar. 2, 2006, which claims priority to German Patent Application No. 10 2005 009 705.7, filed Mar. 3, 2005 and to German Patent Application No. 10 2005 029 372.7, filed Jun. 24, 2005, which applications are incorporated herein fully by this reference.

The invention relates to compounds for the selective inhibition of human corticoid synthases CYP11B1 and CYP11B2, the preparation thereof and the use thereof for treating hypercortisolism, diabetes mellitus, hyperaldosteronism, heart failure, myocardial fibrosis, depression, age-related cognitive decline and metabolic syndrome.

BACKGROUND OF THE INVENTION

The adrenal glands of humans are subdivided into two regions, the adrenal medulla and the adrenal cortex. The latter secretes a number of hormones that are known as corticoids and belong to one of two categories, Glucocorticoids (mainly hydrocortisone or cortisol) primarily act on the carbohydrate and glucose metabolism, and secondarily, they can delay wound healing by interfering with the inflammatory processes, and the formation of fibrous tissue. The second category, the mineral corticoids, are primarily involved in sodium retention and potassium excretion. The most important and effective mineral corticoid is aldosterone.

The biosynthesis of glucocorticoids is controlled, inter alia, by adrenocorticotropic hormone (ACTH). Steroid 11β, hydroxylase (CYP11B1) is the key enzyme of the biosynthesis of glucocorticoids in humans. In all diseases accompanied by increased cortisol production, this enzyme could play a crucial role. Such clinical pictures include hypercortisolism, especially Cushing's syndrome, and a more specific form of diabetes mellitus that is characterized by an extreme morning rise of the cortisol plasma level.

In the case of Cushing's syndrome, the therapy is usually selected as a function of the cause of the disease. A distinction is made between hypothalamic-pituitary and adrenally caused Cushing's syndrome, which develops due to corticoid-producing tumors of the adrenal cortex.

For the therapy of hypothalamic-pituitary Cushing's syndrome, neuromodulatory substances, such as bromocriptine, cyproheptadine, somastatin or valproic acid, are usually employed; they are supposed to reduce cortisol production through their influence on ACTH release. This therapy proved little effective in the past.

In adrenal Cushing's syndrome, especially if a surgical removal of the primary tumor is not possible, a therapy with inhibitors of steroid biosynthesis is performed. The substances employed include the non-specific CYP enzyme inhibitors aminoglutethimide, metyrapone, ketoconazole and mitotane, which are often employed in the form of a combination therapy. However, the effect on steroidogenesis is based on an attack on CYP11A1, desmolase, in the case of amino-glutethimide, or on the inhibition of CYP17 in the case of ketoconazole. The other compounds mentioned also act non-specifically. Both the combination of several non-selective inhibitors of the steroidogenic CYP enzymes and the high doses that must be employed are objectionable therapeutically. This is of importance mainly in view of the fact that the therapy must be performed for a lifetime and is associated with severe side effects due to the lack of selectivity of the compounds mentioned (Nieman, L. K., Pituitary 5; 77-82 (2002)). In this case, an approach to a solution is the therapy with highly selective inhibitors of the key enzyme of glucocorticoid biosynthesis, CYP11B1. In this case too, selectivity of the compounds is desired lest side effects should occur, especially on androgen production in males (ketoconazole) or on the biosynthesis of mineral corticoids, as described in the past.

Increased cortisol levels are also associated with neurodegenerative diseases. The decline of memory and learning ability upon exposure to increased concentrations of both exogenous and endogenous glucocorticoids (cortisol) has been described (Heffelfinger et al., Dev. Psychopathol. 13: 491-513 (2001)).

In a special form of stress-related diabetes mellitus, a rapid morning rise of the plasma cortisol level occurs. This so-called dawn phenomenon frequently occurs in type 2 diabetics and is characterized by reduced glucose tolerance and a reduction of insulin sensitivity in the early morning hours. The dawn phenomenon complicates diabetic control, so that insulin pump therapy often becomes necessary. With respect to the pathologically altered circadiane rhythm of glucose metabolism in type 2 diabetes, there are results that clearly indicate that this disorder is due to an increase of night cortisol concentrations (Bolli et al., N. Engl. J. Med. 310 (1984) 746-750; Shapiro et al., J. Clin. Endocrinol. Metab. 72 (1991) 444-454; Schultes and Fehm, Der Internist 9 (2004) 983-993).

Further, in diabetes mellitus, increased cortisol levels are attributed to the development of insulin resistance and impairment of glucose tolerance (Phillips et al., J. Clin. Endocrinol. Metab. 83: 757-760 (1998)). The liver plays a central role in the control of glucose equilibrium and in the development of glucose intolerance and type 2 diabetes mellitus. Under physiological conditions, 25% of the glucose supply is accounted for by gluconeogenesis (synthesis of glucose from lactate, pyruvate, glycerol and amino acids) in the liver, while 90% of the glucose are generated in the liver by gluconeogenesis in diabetes mellitus type 2 patients. Glucocorticoids antagonize the action of insulin, regulate hepatic glucose release and result in an increase of the blood glucose levels in diabetes mellitus. Their action consists in controlling the transcription of several genes involved in the regulation of hepatic gluconeogenesis (DeFronzo et al., Diabetes Rev. 5 (1997) 177-269).

The tissue-specific response is regulated by glucocorticoid receptor and the intracellular synthesis of active glucocorticoids by 11beta-hydroxysteroid dehydrogenase type 1 (11β-HSD-1). 11β-HSD-1 catalyzes the production of cortisol from cortisone in the liver and in adipocytes and the pancreatic beta cells and thus controls the effect of glucocorticoids in the respective target tissues (Stewart and Krozowski, Vitam. Horm, 57: 249-324 (1999)).

Currently, the application of inhibitors of 11β-HSD-1 is tested for regulating the blood glucose level. In this connection, Alberts et al. report that the selective 11β-HSD-1 inhibitor BVT.2733 resulted in the reduction of both blood glucose levels and insulin levels in hyperglycemic and hyperinsulinic mice (Alberts et al., Diabetologica 45 (2002) 1528-1532). In this case too, selective CYP11B1 inhibitors could reduce the increased cortisol release that results in a rise of the blood glucose levels and reduction of insulin sensitivity.

The application of inhibitors of 11β-HSD-1 for the regulation of blood glucose level is described, for example, in EP 1 461 333. The indications for 11-HSD-1 inhibitors also apply, mutatis mutandis, for the application of CYP11B1 inhibitors. In this case too, the inhibition of glucocorticoid biosynthesis by the direct and selective inhibition of the key enzyme CYP11B1 could be a therapeutic alternative.

Aldosterone secretion is regulated by a number of signals: the plasma concentrations of sodium and potassium and the renin-angiotensin-aldosterone system (RAAS), which proceeds through several steps. In this system, in response to a low blood pressure, the kidneys secrete renin that releases angiotensin I from a precursor peptide. Angiotensin I is in turn cleaved into angiotensin II, which comprises 8 amino acids and is a potent vasoconstrictor. In addition, it acts as a hormone for stimulating the release of aldosterone (Weber, K. T. & Brilla, C. G., Circulation 83: 1849-1865 (1991)).

The key enzyme of mineral corticoid biosynthesis, CYP11B2 (aldosterone synthase), a mitochondrial cytochrome P450 enzyme, catalyzes the production of the most potent mineral corticoid, aldosterone, from its steroidal substrate 11-deoxycorticosterone (Kawamoto, T. et al., Proc. Natl. Acad. Sci. USA 89: 1458-1462 (1992)). Excessive plasma aldosterone concentrations are related to clinical pictures such as congestive heart failure, myocardial fibrosis, ventricular arrhythmia, stimulation of cardiac fibroblasts, cardiac hypertrophy, reduced renal perfusion and hypertension, and they are also involved in the progression of these diseases (Brilia, C. G., Herz 25: 299-306 (2000)). Especially in patients suffering from chronic heart failure or reduced renal perfusion of kidney artery stenoses, a pathophysiological activation of the renin-angiotensin system (RAAS) occurs in contrast to its physiological action (Young, M Funder, J. W., Trends Endocrinol. Metab. 11: 224-226 (2000)). Angiotensin II-mediated vasoconstriction and water and sodium restriction, which occur due to the increased aldosterone levels, result in an additional extra load of the myocardium, which is already subject to primary insufficiency. In a kind of vicious circle, this results in a further reduction of renal perfusion and increased renin secretion. In addition, the increased plasma aldosterone and angiotensin II levels as well as aldosterone secreted locally in the heart induce fibrotic structural changes of the myocardium, which results in the formation of myocardial fibrosis, which leads to a further reduction of heart performance (Brilla, C. G., Cardiovasc. Res. 47: 1-3 (2000); Lijnen, P. & Petrov, V., J. Mol. Cell. Cardiol. 32: 865-879 (2000)).

Fibrotic structural changes are characterized by the formation of tissue that is characterized by an abnormally high amount of fibrotic material (mainly collagen strands). In some situations, such as wound healing, such fibroses are useful, but may also be deleterious, such as when adversely affecting the function of inner organs, inter alia. In myocardial fibrosis, the heart muscle is nerved by fibrotic strands that render the muscle stiff and inflexible and thereby impair its function.

Since the mortality is 10-20% even for patients with only a slight cardiac failure, it is absolutely necessary to interfere by using a suitable drug therapy. Despite long-term therapy with digitalis glycosides, diuretics, ACE inhibitors or AT-II antagonists, the plasma aldosterone levels remain elevated in the patients, and the drug treatment has no effect with respect to the fibrotic structural changes.

Mineral corticoid antagonists, especially aldosterone-blocking drugs, are already the subject of numerous patents. Thus, the steroidal mineral corticoid antagonist spironolactone (17-hydroxy-7-alpha-mercapto-3-oxo-17-α-pregn-4-ene-21-carboxylic acid γ-lactone acetate; Aldactone®) blocks aldosterone receptors in competition with aldosterone and thus prevents the receptor-mediated action of aldosterone. US 2002/0013303, U.S. Pat. No. 6,150,347 and U.S. Pat. No. 6,608,047 describe the dosing of spironolactone for the therapy or prophylaxis of cardiovascular diseases and myocardial fibrosis while retaining the patient's normal electrolyte and water metabolism.

The "Randomized Aldactone Evaluation Study (RALES)" (Pitt, B. et al., New Engl. J. Med. 341: 709-717 (1999)) impressively showed that the administration of the aldosterone receptor antagonist spironolactone (Aldactone®) in addition to the basic therapy with ACE inhibitors and loop diuretics could significantly improve the survival rate of patients with severe heart failure, because the action of aldosterone was sufficiently inhibited (Kulbertus, H., Rev. Med. Liege 54: 770-772 (1999)). However, the application of spironolactone was accompanied by severe side effects, such as gynecomasty, dysmenorrhoea and breast pain, which are due to the steroidal structure of the substance and the resulting interactions with other steroid receptors (Pitt, B. et al., New Eng, J. Med. 341: 709-717 (1999); MacFadyen, R. J. et al., Cardiovasc. Res. 35: 30-34 (1997); Soberman, J. E. & Weber, K. T., Curr. Hypertens. Rep. 2: 451-456 (2000)).

Mespirenone (15,16-methylene-17-spirolactone) and its derivatives were considered promising alternatives for spironolactone, since they exhibit only a low percentage of the anti-androgenic effect of spironolactone (Losert, W. et al., Drug Res. 36: 1583-1600 (1986); Nickisch, K. et al., 3 Med Chem 30(8); 1403-1409 (1987); Nickisch, K. et al., J. Med. Chem. 34: 2464-2468 (1991); Agarwal, M. K., Lazar, G., Renal Physiol. Biochem. 14: 217-223 (1991)). Mespirenone blocks aldosterone biosynthesis as part of a complete inhibition of mineral corticoid biosynthesis (Weindel, K. et al., Arzneimittelforschung 41(9): 946-949 (1991)). However, like spironolactone, mespirenone inhibits aldosterone biosynthesis only in very high concentrations.

WO 01/34132 describes methods for the treatment, prophylaxis or blocking of pathogenic change resulting from vascular injury (restenoses) in mammals by administering an aldosterone antagonist, namely eplerenone (an aldosterone receptor antagonist) or related structures which are in part epoxysteroidal and all of which can be derived from 20-spiroxanes.

WO 96/40255, US 2002/0123485, US 2003/0220312 and US 2003/0220310 describe therapeutic methods for treating cardiovascular diseases, myocardial fibrosis or cardiac hypertrophy by using a combination therapy of an angiotensin II antagonist and an epoxy-steroidal aldosterone receptor antagonist, such as eplerone or epoxymexrenone.

The recently published study EPHESUS ("Eplerenone's Heart Failure Efficacy and Survival Study", 2003) could support the RALES results. Administered as a supplement to the basic therapy, the first selective steroidal mineral corticoid receptor antagonist eplerone (Inspra®) clearly reduces morbidity and mortality in patients with acute myocardial infarction and the occurrence of complications, for example, reduced left-ventricular ejection fraction and heart failure (Pitt., B. et al., N. Eng. J. Med. 348: 1390-1382 (2003)).

RALES and EPHESUS clearly demonstrated that aldosterone antagonists are a therapy option that is not to be underestimated. However, their side effect profile urges a demand for substances which are distinguished from spironolactone in structure and mechanism of action. A promising alternative are non-steroidal inhibitors of mineral corticois biosynthesis, because it is better to reduce the pathologically increased aldosterone concentration than just to block the receptors. In this connection, CYP11B2 as a key enzyme offers itself as a target for specific inhibitors and has already been proposed as a target for specific inhibitors in earlier studies (Hartmann, R.

et al., Eur. J. Med. Chem. 38: 363-366 (2003); Ehmer, P. et al., J. Steroid Biochem. Mol. Biol. 81: 173-179 (2002)). Thus, the excessive generalized release of aldosterone and especially cardiac aldosterone production can be reduced by the selective inhibition of its biosynthesis, which in turn reduces structural changes in the myocardium.

Selective aldosterone synthase inhibitors could also be a promising class of substances that promote the healing of the impaired myocardial tissue with reduced scar formation after a myocardial infarction and thus reduce the occurrence of severe complications.

WO 01/76574 describes a medicament which comprises an inhibitor of aldosterone production or one of its pharmaceutically acceptable salts, optionally in combination with other active substances. WO 01/76574 relates to the use of, at the time, commercially available non-steroidal inhibitors of aldosterone production, especially the (+)-enantiomer of fadrozole, a 4-(5,6,7,8-tetrahydroimidazo-[1,5-a]pyridine-5-yl)benzonitrile, and its synergistic action with angiotensin II receptor antagonists.

Anastrozole (Arimidex®) and exemestane (Coromasin®) are further non-steroidal aromatase inhibitors. Their field of application is the treatment of breast cancer by inhibiting the aromatase that converts androstendione and testosterone to estrogen.

Human steroid 11β-hydroxylase CYP11B1 shows a homology of more than 93% with human CYP11B2 (Kawamoto, T. et al., Proc. Natl. Acad. Sci. USA 89: 1458-1462 (1992); Taymans, S. E. et al., J. Clin. Endocrinol. Metab. 83: 1033-1036 (1998)). Despite the high structural and functional similarity between these two enzymes, strong inhibitors of aldosterone synthase must not influence the steroid 11β-hydroxylase and therefore must be tested for selectivity. In addition, non-steroidal inhibitors of aldosterone synthase should be preferably applicable as therapeutic agents since less side effects on the endocrine system are to be expected. This has been pointed out in earlier studies, as has the fact that the development of selective CYP11B2 inhibitors that do not influence CYP11B1 is complicated by the high similarity between the two enzymes (Ehmer, P. et al., J. Steroid Biochem. Mol. Biol. 81: 173-179 (2002); Hartmann, R. et al., Eur. J. Med. Chem. 38: 363-366 (2003)).

The inhibitors should also affect other P450 (CYP) enzymes as little as possible. The only active substance known to date which influences the corticoid synthesis in humans is the aromatase (estrogen synthase, CYP19) inhibitor fadrozole, which is employed in breast cancer therapy. It may also influence aldosterone and cortisone levels, but only when ten times the therapeutic dose is administered (Demers, L. M. et al., J. Clin. Endocrinol. Metabol. 70: 1162-1166 (1990)).

For inhibitors of the human aldosterone synthase CYP11B2, a test system for screening chemical compounds with *Schizosaccharomyces pombe* cells that stably express human CYP112 and for subsequently testing the selectivity with V79MZ cells that stably express either CYP11B2 or CYP11B has been developed (Ehmer, P. et al., 3, Steroid Biochem, Mol. Biol. 81: 173-179 (2002)). By means of the *S. pombe* system, 10 substances were tested in an exemplary manner, of which one was identified as a potent and selective non-steroidal inhibitor of human CYP11B2 (and strong aromatase inhibitor) and four others were identified as non-selective inhibitors, but which were stronger towards CYP11B1, by means of the V79MZ system (A: CYP11B2 inhibitor; B-D: non-selective CYP11B1 inhibitors):

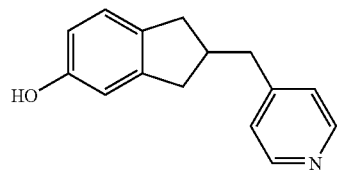

A

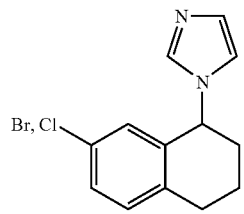

B

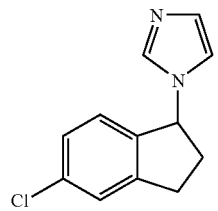

C

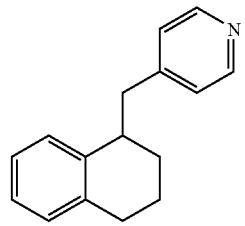

D

However, this publication was focused on the provision of an effective test system for the screening for selective CYP11B2 inhibitors, and except the quite general reference to the aromatic N atom and the three structures shown above, it gives very few indications of what classes of substances could be particularly effective ultimately. Further, it may be noted that most of the structures presented in this publication were strong CYP11B1 inhibitors and therefore should not be taken into account for immediate use as selective CYP11B2 inhibitors.

The screening of a P450 inhibitor library of more than 100 substances for inhibitors of bovine aldosterone synthase (CYP18, CYP11B) (in part published in Hartmann, R. W. et al., Arch. Pharm. Pharm. Med. 339, 251-61 (1996)) by means of the test system presented by Ehmer et al. (Ehmer, P. et al., 1. Steroid Biochem. Mol. Biol. 81: 173-179 (2002)) yielded a high number of compounds that have an inhibitors effect on CYP11B2 (Hartmann, R. et al., Eur. J. Med. Chem. 38; 363-366 (2003)). In the scope of the cited study, these substances were also tested for oral availability and further for in vitro inhibition of human CYP11B2 stably expressed in yeast and, if these tests showed a strong inhibition of CYP11B2, in V79MZ cells. Comparisons with the inhibition of other CYPs, including CYP11B1, expressed in V79MZ cells were also made in order to establish the selectivity of the test substances. By structural variation, finally, CYP11B2 inhibitors that showed $IC_{50}$ values in the low nanomolar range were found, namely cyclopropatetrahydronaphthalene derivatives and arylmethyl-substituted indanes. It has been established that the CYP11B inhibition is strongly influenced by the substituent at the benzene ring and by the heteroaryl residue. Compounds E and F were found as promising lead structures:

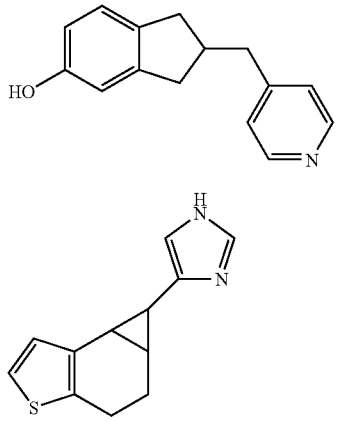

E

F

The above mentioned scientific publications indicate that the presence of an aromatic nitrogen atom is essential to the complexing of the iron atom in the target enzyme (Ehmer, P. et al., J. Steroid Biochem. Mol. Biol. 81: 173-179 (2002); Hartmann, R. et al., Eur. J. Med. Chem. 38; 363-366 (2003)). In addition, this N atom must be unsubstituted and sterically accessible (Ehmer, P. et al., J. Steroid Biochem. Mol. Biol. 81: 173-179 (2002)).

Only a few heteroaryl-substituted dihydronaphthalenes were tested for their activity as inhibitors of non-specific bovine CYP11B already in the preliminaries to the invention presented here (Hartmann, R. W. et al., Arch. Pharm. Pharm. Med. Chem. 329: 251-261 (1996)):

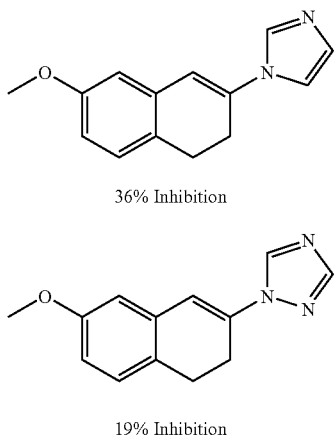

G

36% Inhibition

H

19% Inhibition

Their effect on CYP17 and CYP19 is also described in this publication. However, they proved to be too non-specific to be considered as therapeutic agents for the selective inhibition of CYP11B2. In addition, the bovine enzyme is not optimal for evaluating the therapeutic usefulness of compounds for the inhibition of human CYP11B enzymes, since the homology between this bovine enzymes and the human enzymes is not high (75%) (Mornet, E. et al., J. Biol, Chem. 264, 20961-20967 (1989)).

Further, the effect of the following compound on CYP17, CYP19 and TxA2 (thromboxane A2 synthase) has been described, but an inhibitory effect on CYP11B has not been mentioned (Jacobs, C. et al., J. Med. Chem. 43: 1841-1851 (2000)):

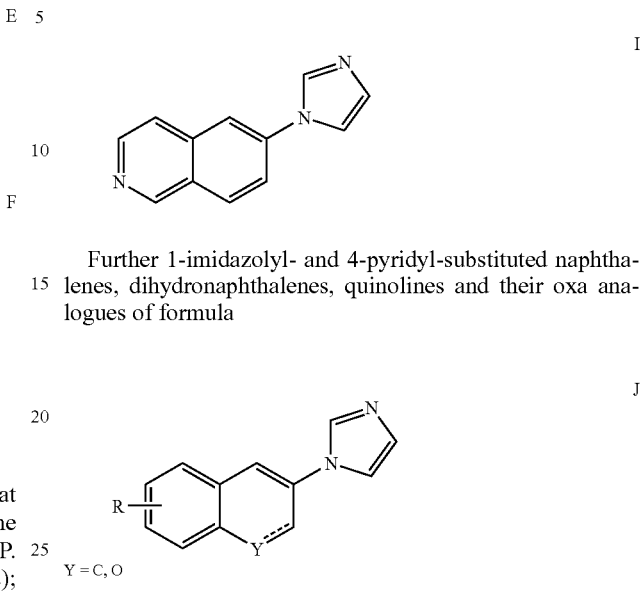

I

Further 1-imidazolyl- and 4-pyridyl-substituted naphthalenes, dihydronaphthalenes, quinolines and their oxa analogues of formula

J

Y = C, O are described as TxA2 inhibitors (Cozzi, P. et al., Eur. J. Med. Chem. 26: 423-433 (1991)).

Also,

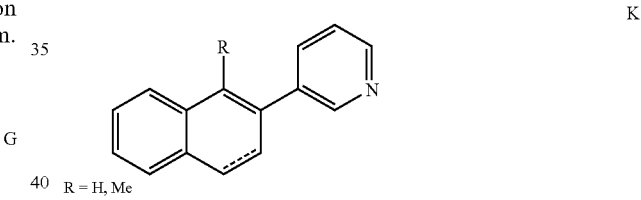

K

R = H, Me has already been mentioned as an inhibitor of CYP17 (Bencze, W. L. and Barsky, L. I., J. Med. Pharm. Chem. 5: 1298-1306 (1962) and U.S. Pat. No. 3,165,525).

Further,

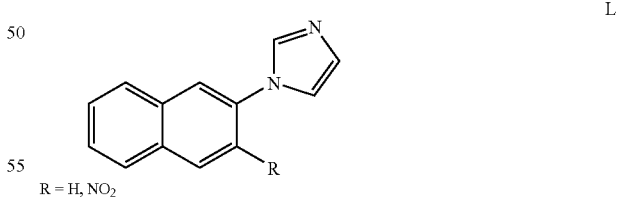

L

R = H, NO$_2$ has been proposed as a tool for the diagnosis of primary and secondary aldesteronism and diabetes mellitus as an alternative for metyrapone (Johnson, A. L. et al., J. Med. Chem. 12(5): 1024-1028 (1969)).

Some pyridine-substituted quinolines are thought to have a spasmolytic effect (Hey, D. H. und Williams, J. M., J. Chem. Soc. 1678-83 (1950)).

U.S. Pat. No. 3,098,077 discloses 2-pyridylindenes and their use for inhibiting hyperadrenocortfcism.

All inhibitors of aldosterone or glucocorticoid production known to date have substantial drawbacks: Etomidate and metyrapone inhibit glucocorticoid production more strongly than they inhibit aldosterone production. Etomidate is a strong narcotic, and metyrapone is a relatively non-selective CYP inhibitor which is therefore employed only as a diagnostic agent. Fadrozole has been described to inhibit aldosterone production more strongly than it inhibits glucocorticoid production (Bhatnagar, A. S. et al., J. Steroid Biochem. Mol. Biol. 37: 1021-1027 (1990); Hausler, A. et al., J. Steroid Biochem. 34: 567-570 (1989); Dowsett, M. et al., Clin. Endocrinol. (Oxf.) 32: 623-634 (1990); Santen, R. J. et al., J. Clin. Endocrinol. Metabol. 73: 99-106 (1991); Demers, L. M. et al., J. Clin. Endocrinol. Metabol. 70; 1162-1166 (1990)). This substance cannot be considered for application as an inhibitor of aldosterone or glucocorticoid production either, because it is a very strong aromatase inhibitor and therefore interferes with the production of sexual hormones with high potency. In the light of the above mentioned prior art, there has been a need for potent and selective inhibitors of the 11β-hydrolase CYP11B1 and the aldosterone synthase CYP11B2.

3-Pyridyl-substituted quinolines and quinoxalines were prepared already by a Fe(salen)Cl-catalyzed cross-coupling reaction of a correspondingly chlorinated heteroaryl with a pyridyl Grignard compound (Furstner, A. et al., JACS 124: 13866-13863 (2002)).

The 3-pyridyl Grignard compound also reacts with ethyl-2-quinolinyl sulfoxide to give 2-pyridine-3-ylquinoline 20 (Furukawa, N. et al., Tet. Lett. 28(47): 5845-8 (1987)). Another synthesis method for this compound is the treatment of o-aminobenzaldehyde with 3-pyridylmethylketone (Hey, D. H. and Williams, J. M., J. Chem. Soc. 1678-83 (1950)).

3-Pyridine-3-ylquinoline 19 can be prepared by a palladium-catalyzed cross-coupling reaction of tri(quinolinyl)magnesate with 6-bromopyridine (Dumouchel, S. et al., Tetrahedron 59: 8629-8640 (2003)). 2-Pyridine-3-ylquinoxaline 21 is obtainable by reacting o-phenylenediamine with brominated 3-pyridylmethylketone (Sarodnick G. and Kempter G., Pharmazie 40(6); 384-7 (1985)).

All mentioned cross-coupling reactions with iron or palladium complexes have drawbacks: For preparing the iron complex, an additional synthetic step becomes necessary, and the coupling of arylmagnesates requires the expensive ligand dppf (1,1'-bis(diphenylphosphino)ferrocene). In addition, the safe handling of the reagents is difficult, and a dry atmosphere and low temperatures are indispensable.

The mentioned reaction of 3-pyridylmethylketone with o-aminobenzaldehyde or o-phenylenediamine results in low yields (20% maximum). Although the synthesis of 4-(6-methoxy-2-naphthyl)pyridine 31 has been described (Kelley, C. J., J. Het. Chem. 38(1): 11-23 (2001)), it involves quite a lot of individual steps.

Therefore, there has also been a need for a simple synthesis method for heteroaryl substituted naphthalenes, 3,4-dihydroxynaphthalenes and indanes, which can be applied to a broad range of heteroaryls.

SUMMARY OF THE INVENTION

It has been found that certain aromatic compounds are suitable for selectively inhibiting the 11β-hydroxylase CYP11B1 and/or the aldosterone synthase CYP11B2. Their biological activity with respect to the inhibition of human CYP11B2 and CYP11B1 as well as for establishing the selectivity of human CYP17 (17α-hydroxylase C17,20-lyase, key enzyme of androgen biosynthesis) and CYP19 has been examined. As compared to CYP11B2 inhibitors that have already been described (Hartmann, R. W. et al., Eur. J. Med. Chem. 38: 363-366 (2003)) and to known inhibitors of corticoid biosynthesis (fadrozole) or steroid biosynthesis (ketoconazole), the compounds presented in the following are more potent and selective.

Further, a suitable synthesis method has been developed for these aromatic compounds whose main representatives are 3-pyridyl-substituted naphthalenes, 3,4-dihydronaphthalenes and indanes.

Thus, the invention relates to:
(1) the use of a compound having a structure of formula (I)

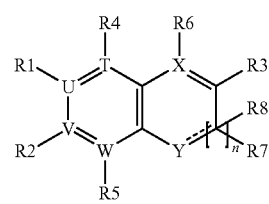

wherein
Y is selected from

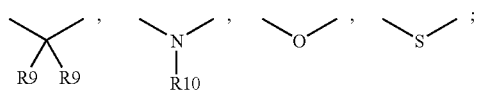

T, U, V, W, X are independently selected from C and N;
$R^1$ and $R^2$ are independently selected from H, halogen, CN, hydroxy, nitro, alkyl, alkoxy, alkylcarbonyl, alkylcarbonyloxy, alkylcarbonylamino, alkylsulfonylamino, alkylthio, alkylsulfinyl and alkylsulfonyl (wherein the alkyl residues are straight-chain, branched-chain or cyclic, saturated or unsaturated and substituted with 1 to 3 residues $R^{12}$), arylalkyl, heteroarylalkyl, aryl and heteroaryl residues and their partially or completely saturated equivalents, which may be substituted with 1 to 3 residues $R^{12}$, arylalkyloxy, heteroarylalkyloxy, aryloxy and heteroaryloxy residues, wherein aryl and heteroaryl have the meaning as defined above, —$COOR^{11}$, —$CON(R^{11})_2$, —$SO_3R^{11}$, —CHO, —$CHNR^{11}$, —$N(R^{11})_2$, —$NHCOR^{11}$ and —$NHS(O)_2R^{11}$, and, if U or V is an N atom, a lone electron pair; or
$R^1$ with $R^1$ or $R^4$, or $R^2$ with $R^5$ of the neighboring ring atom and the related carbon atoms form a saturated or unsaturated anellated aryl or heteroaryl ring, wherein the atoms of the anellated aryl or heteroaryl ring may be substituted with 1-3 residues $R^{12}$;
$R^3$ is selected from nitrogen-containing monocyclic or bicyclic heteroaryl residues and their partially or completely saturated equivalents, which may be substituted with 1 to 3 residues $R^{12}$ and have at least one nitrogen atom that is not substituted; and/or
$R^3$ through $R^{12}$ with $R^6$ or $R^7$, or $R^8$ of the neighboring ring atom and the related carbon atoms form a saturated or unsaturated anellated aryl or heteroaryl ring, wherein the atoms of the anellated aryl or heteroaryl ring may be substituted with 1-3 residues $R^{12}$;
$R^4, R^5, R^6, R^7, R^8$ and $R^9$ are independently selected from H. halogen, CN, hydroxy, nitro, lower alkyl, lower alkoxy, lower alkylcarbonyl, lower alkylcarbonyloxy, lower alkylcarbonylamino, lower alkylsulfonylamino, lower alkylthio, lower alkylsulfinyl and lower alkylsulfonyl (wherein the lower alkyl residues are straight-chain, branched-chain or cyclic, saturated or unsaturated and may be substituted with 1 to 3 residues $R^{12}$), arylalkyl, heteroarylalkyl, aryl and heteroaryl residues and their partially or completely saturated equivalents, which may be substituted with 1 to 3 residues $R^{12}$, arylalkyloxy, heteroarylalkyloxy, aryloxy and heteroaryloxy residues, wherein aryl and heteroaryl have the meaning as defined above, —COOR$^{11}$, —CON(R$^{11}$)$_2$, —SO$_3$R$^{11}$, —CHO, —CHNR$^{11}$, —N(R$^{11}$)$_2$, —NHCOR$^{11}$ and —NHS(O)$_2$R$^{11}$; or $R^4$, $R^5$ and $R^6$ is a lone electron pair if T, W or X is an N atom; or $R^7$ or $R^8$ with $R^3$ or $R^{10}$ and/or with $R^7$ or $R^8$ of the neighboring ring atom form one or two double bonds; or $R^9$ and/or $R^7$ (and $R^8$) with $R^9$ (and $R^{10}$) of the neighboring ring atom and the related carbon atoms form a saturated or unsaturated anellated aryl or heteroaryl ring, wherein the atoms of the anellated aryl or heteroaryl ring may be substituted with 1-3 residues $R^{12}$;

$R^{10}$ is selected from H, lower alkyl, lower alkylcarbonyl (wherein the lower alkyl residues are straight-chain, branched-chain or cyclic, saturated or unsaturated and substituted with 1 to 3 residues $R^{12}$), arylalkyl, heteroarylalkyl, aryl and heteroaryl residues and their partially or completely saturated equivalents, which may be substituted with 1 to 3 residues $R^{12}$, and —COOR$^{11}$, or is a lone electron pair; or forms a double bond with $R^7$ or $R^8$ of the neighboring carbon atom; or forms a saturated or unsaturated anellated heteroaryl ring with $R^7$ (and $R^8$) of the neighboring carbon atom and the related carbon atoms, wherein the atoms of the anellated heteroaryl ring may be substituted with 1-3 residues $R^{12}$;

$R^{11}$ independently of the occurrence of further $R^{11}$ residues is selected from H, lower alkyl (which may be straight-chain, branched-chain or cyclic, saturated or unsaturated and substituted with 1 to 3 $R^{12}$) and aryl, which may be substituted with 1 to 3 $R^{12}$;

$R^{12}$ independently of the occurrence of further $R^{12}$ residues is selected from H, hydroxy, halogen, —CN, —COOH, —CHO, nitro, amino, mono- and bis(lower alkyl)amino, lower alkyl, lower alkoxy, lower alkylcarbonyl, lower alkylcabonyloxy, lower alkylcarbonylamino, lower alkylthio, lower alkylsulfinyl, lower alkylsulfonyl, hydroxy(lower alkyl), hydroxy(lower alkoxy), hydroxy(lower alkyl)-carbonyl, hydroxy(lower alkyl)carbonyloxy, hydroxy(lower alkyl) carbonylamino, hydroxy(lower alkyl)thio, hydroxy(lower alkyl)sulfinyl, hydroxy(lower alkyl)-sulfonyl, mono- and bis (hydroxy(lower alkyl))amino and mono- and polyhalogenated lower alkyl (wherein the lower alkyl residues may be straight-chain, branched-chain or cyclic, saturated or unsaturated);

n is an integer of from 0 to 2;

or a pharmaceutically acceptable salt thereof for preparing a medicament for treating hyperaldosteronism, heart failure, myocardial fibrosis, hypercortisolism, diabetes mellitus, depression, age-related cognitive decline and metabolic syndrome;

(2) a pharmaceutical composition containing a compound of formula (I), wherein T, U, V, W, X, Y, $R^1$, $R^2$, $R^3$, $R^4$, $R^5$, $R^6$, $R^7$, $R^8$, $R^9$, $R^{10}$, $R^{11}$ and $R^{12}$ are as defined in (1), or a pharmaceutically acceptable salt thereof, with the proviso that:

(a) if T, U, V, W and X are carbon atoms, n=1 and Y is selected from O, CH$_2$ and —CH═, then $R^3$ is not 1-imidazolyl;

(b) if T, U, V, W, X and Y are carbon atoms, n=1, $R^1$, $R^2$, $R^4$, $R^5$, $R^7$, $R^8$ and $R^9$ are hydrogen atoms and $R^6$ is H or C$_{1-4}$ alkyl, then $R^3$ is not 3- or 4-pyridyl;

(c) if T, U, V, W, X and Y are carbon atoms, n=1, $R^2$, $R^4$, $R^5$, $R^6$, $R^7$, $R^8$ and $R^9$ are hydrogen atoms and $R^1$ is COOH, then $R^3$ is not 4-pyridyl;

(d) if T, U, V, W and Y are carbon atoms, X═N, n=1, $R^1$, $R^2$, $R^4$, $R^5$ and $R^7$ are hydrogen atoms, $R^9$═H or methyl, and $R^8$ with Y forms a double bond, then $R^3$ is not pyridyl;

(e) if T, U, V, W and X are carbon atoms, Y═N, n=1, $R^1$, $R^2$, $R^4$, $R^5$, $R^6$ and $R^7$ are hydrogen atoms and $R^8$ with Y forms a double bond, then $R^3$ is not 4-carboxy-2-pyridyl; and (f) if T, U, V, W and X are carbon atoms, Y is (R$^9$)$_2$, n=0, $R^1$, $R^4$ and $R^5$ are hydrogen atoms, $R^2$ is a halogen atom, $R^6$ is H, methyl, ethyl, n-propyl or i-propyl, one of $R^9$ is H and the other is H, methyl or ethyl, then $R^3$ is not 3- or 4-pyridyl;

(3) a compound of formula (I), wherein T, U, V, W, X, Y, $R^1$, $R^2$, $R^3$, $R^4$, $R^5$, $R^6$, $R^7$, $R^8$, $R^9$, $R^{10}$, $R^{11}$ and $R^{11}$ are as defined in (1), or a pharmaceutically acceptable salt thereof, with the proviso that:

(a) if T, U, V, W and X are carbon atoms, n=1 and Y is selected from O, N, CH$_2$ and —CH═, then $R^3$ is not 1-imidazolyl;

(b) if T, U, V, W, X and Y are carbon atoms, n=1, $R^1$, $R^4$, $R^5$, $R^7$, $R^8$ and $R^9$ are hydrogen atoms, $R^2$ is H or methoxy and $R^6$ is H or methyl, then $R^3$ is not pyridyl, imidazolyl or oxazolyl;

(c) if T, U, V, W, X and Y are carbon atoms, n=1, $R^2$, $R^4$, $R^5$, $R^6$, $R^7$, $R^8$ and $R^9$ are hydrogen atoms and $R^1$ is COOH, then $R^3$ is not 4-pyridyl;

(d) if T, U, V, W and Y are carbon atoms, X═N, n=1, $R^1$, $R^2$, $R^4$, $R^5$ and $R^7$ are hydrogen atoms, $R^9$═H or methyl, and $R^8$ with Y forms a double bond, then $R^3$ is not pyridyl or quinolyl;

(e) if T, U, V, W and X are carbon atoms, Y═N, n=1, $R^1$, $R^2$, $R^4$, $R^5$, $R^6$ and $R^7$ are hydrogen atoms and $R^8$ with Y forms a double bond, then $R^3$ is not 4-carboxy-2-pyridyl, 5-bromo-2-pyridyl, 6-bromo-2-pyridyl, 5-bromo-3-pyridyl, 2-pyridyl, 3-pyridyl, 2-pyridazinyl, 2-pyrimidinyl or quinolyl;

(f) if T, U, V and W are carbon atoms, X and Y are N atoms, n=1, $R^1$, $R^2$, $R^4$, $R^5$ and $R^7$ are H atoms and $R^8$ with Y forms a double bond, then $R^3$ is not pyridyl or 2-quinolyl;

(g) if T, U, V, W and X are carbon atoms, Y is (R$^9$)$_2$, n=0, $R^1$, $R^4$ and $R^5$ are H atoms, $R^2$ is a halogen atom, $R^6$ is H, methyl, ethyl, n-propyl or i-propyl, one of $R^9$ is H and the other is H, methyl or ethyl, then $R^3$ is not 3- or 4-pyridyl; and (h) if T, U, V, W, X and Y are carbon atoms, n=1, $R^1$, $R^2$, $R^4$, $R^5$, $R^7$, $R^8$ and $R^9$ are H atoms and $R^6$ is H or C$_{1-4}$ alkyl, then $R^3$ is not 3- or 4-pyridyl;

(4) a process for the synthesis of the compounds according to (3), comprising (i) the Suzuki coupling of compound (III)

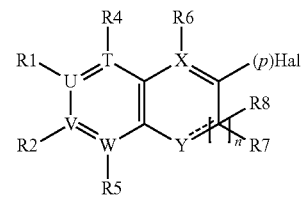

wherein (p)Hal is a halogen atom or pseudohalide, preferably Br or OTf, with compound (II)

R³—B(OH)₂

II; and/or (ii) the bromination of compound (VI)

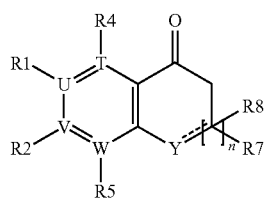

VI to form the corresponding α-bromoketone, followed by reduction to the corresponding alcohol, dehydrogenation and subsequent coupling with compound (II), wherein the variables have the meaning as stated under (3), and functional groups in $R^1$-$R^{10}$ may optionally be provided with appropriate protecting groups;

(5) the use of the compounds as defined under (1) for the preparation of a medicament for the selective inhibition of mammal P450 oxygenases, for the inhibition of human or mammal aldosterone synthase or steroid 11-hydroxylase, especially for the inhibition of the human steroid 11β-hydroxylase CYP11B1 or the aldosterone synthase CYP11B2, especially for the selective inhibition of CYP11B2 while human CYP11B1 is little affected; and (6) a process for the prophylaxis, slowing of progression or therapy of hyperaldosteronism, heart failure, myocardial fibrosis, hypercortisolism, diabetes mellitus, depression, age-related cognitive decline and metabolic syndrome in a patient, comprising the administering of an effective amount of a compound as defined under (1) to the patient.

DETAILED DESCRIPTION OF THE INVENTION

Figure 1A:
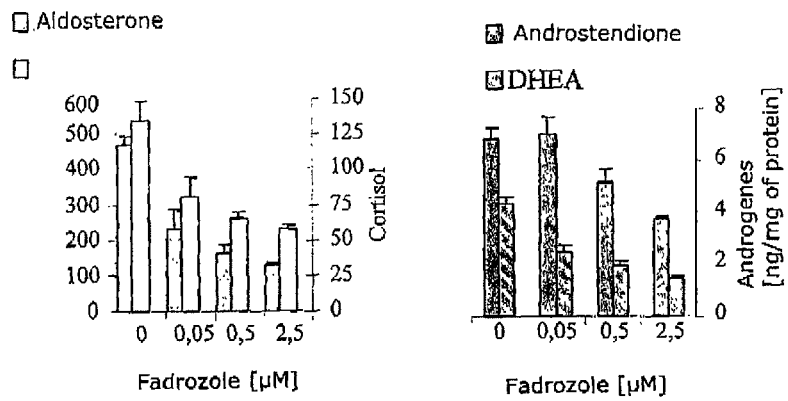
FIG. 1: Steroid secretion of H295R cells upon treatment with inhibitors of steroid biosynthesis as a function of the inhibitor concentration after 6 hours of incubation (Example 9); 1A: fadrozole, 1B: ketoconazole, 1C: compound 2.

In the compounds of formula (I) of the invention, the variables and the terms used for the characterization thereof have the following meanings:

"Alkyl residues" and "alkoxy residues" within the meaning of the invention may be straight-chain, branched-chain or cyclic and saturated or (partially) unsaturated. Preferred alkyl residues and alkoxy residues are saturated or have one or more double and/or triple bonds. For straight-chain or branched-chain alkyl residues, those having from 1 to 10 carbon atoms, especially those having from 1 to 6 carbon atoms, even more preferably those having from 1 to 3 carbon atoms, are preferred. For the cyclic alkyl residues, mono- or bicyclic alkyl residues having from 3 to 15 carbon atoms, especially monocyclic alkyl residues having from 3 to 8 carbon atoms, are especially preferred.

"Lower alkyl residues" and "lower alkoxy residues" within the meaning of the invention are straight-chain, branched-chain or cyclic saturated lower alkyl residues and lower alkoxy residues or those having a double or triple bond. For the straight-chain ones, those having from 1 to 6 carbon atoms, especially those having from 1 to 3 carbon atoms, are especially preferred. For the cyclic ones, those having from 3 to 8 carbon atoms are especially preferred.

"Aryls" within the meaning of the present invention comprise mono-, bi- and tricyclic aryl residues having from 3 to 18 ring atoms which may optionally be anellated with one or more saturated rings. Particularly preferred are anthracenyl, dihydronaphthyl, fluorenyl, hydrindanyl, indanyl, indenyl, naphthyl, naphthenyl, phenanthrenyl, phenyl and tetralinyl.

Unless stated otherwise, "heteroaryl residues" are mono- or bicyclic heteroaryl residues having from 3 to 12 ring atoms preferably comprising from 1 to 5 heteroatoms selected from nitrogen, oxygen and sulfur, optionally anellated with one or more saturated rings. The preferred nitrogen-containing monocyclic and bicyclic heteroaryls comprise benzimidazolyl, benzothiazolyl, benzoxazolyl, quinazolinyl, quinolyl, quinoxalinyl, cinnolinyl, dihydroindolyl, dihydroisoindolyl, dihydropyranyl, dithiazolyl, homopiperidinyl, imidazolidinyl, imidazolinyl, imidazolyl, indazolyl, indolyl, isoquinolyl, isoindolyl, isothiazolidinyl, isothiazolyl, isoxazolidinyl, isoxazolyl, morpholinyl, oxadiazolyl, oxazolidinyl, oxazolyl, phthalazinyl, piperazinyl, piperidyl, pteridinyl, purinyl, pyrazolidinyl, pyrazinyl, pyrazolyl, pyrazolinyl, pyridazinyl, pyridyl, pyrimidyl, pyrrolidinyl, pyrrolidin-2-onyl, pyrrolinyl, pyrrolyl, tetrazinyl, tetrazolyl, tetrahydropyrrolyl, thiadiazolyl, thiazinyl, thiazolidinyl, thiazolyl, triazinyl and triazolyl. Particularly preferred are mono- or bicyclic heteroaryl residues having from 5 to 10 ring atoms preferably comprising from 1 to 3 nitrogen atoms, oxazolyl, imidazolyl, pyridyl and pyrimidyl being particularly preferred. $R^3$ is most preferably 3-pyridyl.

"Anellated aryl or heteroaryl rings" within the meaning of the present invention comprise those monocyclic rings with from 5 to 7 ring atoms which are anellated with the neighboring ring through two neighboring ring atoms. They may be saturated or unsaturated. Said anellated heteroaryl rings comprise from 1 to 3 heteroatoms, preferably nitrogen, sulfur or oxygen atoms, more preferably oxygen atoms. Preferred anellated aryl rings are cyclohexyl, cyclohexenyl, cyclopentyl, cyclopentenyl and benzyl, and preferred heteroaryl rings are furanoyl, dihydropyranyl, pyranyl, pyrrolyl, imidazolyl, pyridyl and pyrimidyl.

"Pharmaceutically acceptable salts" within the meaning of the present invention comprise salts of the compounds with organic acids (such as lactic acid, acetic acid, amino acid, oxalic acid etc.), inorganic acids (such as HCl, HBr, phosphoric acid etc.) and, if the compounds have acid substituents, also with organic or inorganic bases. Preferred are salts with HCl.

Preferred are compounds of formula (I) as defined above under (1), (2) and (3), wherein:

(i) Y is either N or C; and/or (ii) T, U, V and W are carbon atoms; and/or (iii) the alkyl residues and alkoxy residues are saturated or have one or more double and/or triple bonds, the straight-chain or branched-chain alkyl residues preferably have from 1 to 10 carbon atoms, more preferably from 1 to 6 carbon atoms, even more preferably from 1 to 3 carbon atoms, and the cyclic alkyl residues are mono or bicyclic alkyl residues having from 3 to 15 carbon atoms, more preferably monocyclic alkyl residues having from 3 to 8 carbon atoms; and/or (iv) aryl is a mono-, bi- and tricyclic aryl residue having from 3 to 18 ring atoms which may optionally be anellated with one or more saturated rings, especially anthracenyl, dihydronaphthyl, fluorenyl, hydrindanyl, indanyl, indenyl, naphthyl, phenanthrenyl, phenyl, tetralinyl; and/or (v) the heteroaryl residues are mono- or bicyclic heteroaryl residues having from 3 to 5 ring atoms and preferably comprising from 1 to 5 heteroatoms selected from nitrogen, oxygen and sulfur, which may be anellated with one or more saturated rings; and/or (vi) the lower alkyl residues and lower alkoxy residues are saturated or have a double or triple bond, the straight-chain the straight-chain ones especially having from 1 to 6 carbon atoms, more preferably from 1 to 3 carbon atoms, the cyclic ones especially having from 3 to 8 carbon atoms; and/or (vii) the nitrogen-containing monocyclic or bicyclic heteroaryl residues are selected from benzimidazolyl, benzothiazolyl, benzoxazolyl, quinazolinyl, quinolyl, quinoxalinyl, cinnolinyl, dihydroindolyl, dihydroisoindolyl, dihydropyranyl, dithiazolyl, homopiperidinyl, imidazolidinyl, imidazolinyl, imidazolyl, indazolyl, indolyl, isoquinolyl, isoindolyl, isothiazolidinyl, isothiazolyl, isoxazolidinyl, isoxazolyl, morpholinyl, oxadiazolyl, oxazolidinyl, oxazolyl, phthalazinyl, piperazinyl, piperidyl, pteridinyl, purinyl, pyrazolidinyl, pyrazinyl, pyrazolyl, pyrazolinyl, pyridazinyl, pyridyl, pyrimidyl, pyrrolidinyl, pyrrolidin-2-onyl, pyrrolinyl, pyrrolyl, tetrazinyl, tetrazolyl, tetrahydropyrrolyl, thiadiazolyl, thiazinyl, thiazolidinyl, thiazolyl, triazinyl and triazolyl; and/or (viii) anellated aryl or heteroaryl rings are monocyclic rings having from 5 to 7 ring atoms which are anellated with the neighboring ring through two neighboring ring atoms, may be saturated or unsaturated and, as heteroaryl rings, comprise from 1 to 3 heteroatoms, preferably nitrogen, oxygen or sulfur atoms, and are more preferably selected from cyclohexyl, cyclohexenyl, cyclopentyl, cyclopentenyl, benzyl, furanoyl, dihydropyranyl, pyranyl, pyrrolyl, imidazolyl, pyridyl and pyrimidyl.

Particularly preferred are those compounds in which (i) n=0 or 1; and/or (ii) $R^1$ or $R^2$ are independently selected from the group consisting of H, halogen, CN, hydroxy, O-lower alkyl, O-lower alkenyl, O-lower alkinyl, lower alkyl, lower alkenyl, lower alkinyl, —$COOR^{11}$, —$CON(R^{11})_2$ and arylalkyloxy residues, and are more preferably H, O-lower alkyl and arylalkoxy residues; and/or (iii) $R^3$ is selected from nitrogen-containing monocyclic heteroaryl residues with 5-10 ring atoms and from 1 to 3 nitrogen atoms, especially selected from isoquinolyl, imidazolyl, oxazolyl, pyrazinyl, pyrazolyl, pyridyl, pyrimidyl, pyrrolyl, thiazolyl, triazinyl and triazoyl; and/or (iv) $R^4$, $R^5$, $R^6$, $R^7$, $R^8$, $R^9$ are independently selected from H, halogen, CN, hydroxy, heteroaryl and $C_{1-6}$ alkyl and $C_1$-$C_6$ alkoxy residues, which may be substituted with 1 to 3 residues $R^{12}$; and/or (v) $R^{10}$ is selected from H, heteroaryl and $C_{1-6}$ alkyl residues, which may be substituted with 1 to 3 residues $R^{12}$; and/or (vi) $R^{12}$ is selected from H, halogen, hydroxy, CN, $C_{1-3}$ alkyl and $C_{1-3}$ alkoxy.

Among these, particularly preferred are those compounds in which (i) X and Y are carbon atoms; and/or (ii) $R^1$ or $R^2$ is hydrogen and the other of substituents $R^1$ or $R^2$ is selected from H, fluorine, chlorine, bromine, CN, $COOR^{11}$, hydroxy, $C_{1-3}$ alkyl and $C_{1-3}$ alkoxy; and/or (iii) $R^3$ is selected from oxazolyl, pyridyl, imidazolyl and pyrimidyl; and/or (iv) $R^5$ and $R^6$ are independently selected from H, fluorine, chlorine, bromine; and/or (v) $R^7$ is selected from H, $C_{1-3}$ alkyl and $C_{1-3}$ alkoxy; and/or (vi), $R^1$, $R^9$, $R^{10}$ are H; and/or (vii) $R^{11}$ is H or $C_{1-3}$ alkyl.

The compounds of formula (I) may have centers of chirality (e.g., the carbon atoms substituted with $R^9$ and $R^7/R^8$). In this case, both the mixtures of isomers and the isolated individual compounds are included in the invention.

Preferred compounds of embodiments (1), (2) and (3) of the invention are those of formulas (Ia) to (Id);

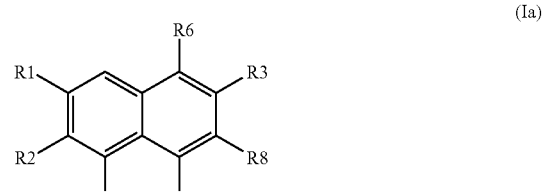

(Ia)

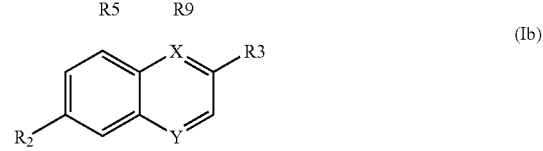

(Ib)

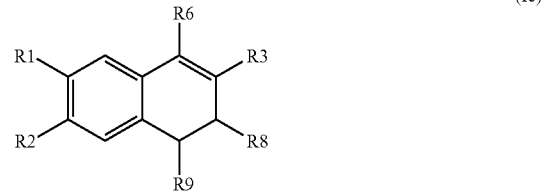

(Ic)

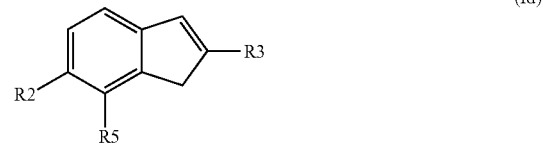

(Id)

wherein $R^3$ is more preferably selected from 3- and 4-pyridyl, 1-imidazolyl, 4-imidazolyl and 5-pyrimidyl, and pharmaceutically acceptable salts thereof.

Preferred embodiments of compound (Ia) are the compounds of the following formulas (Ie) to (Ii):

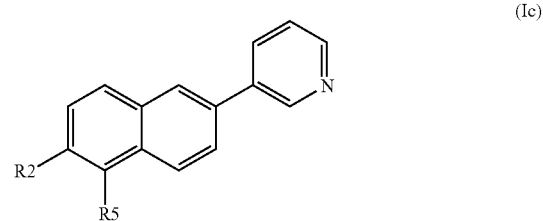

(Ie)

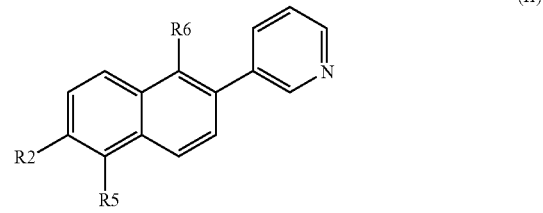

(If)

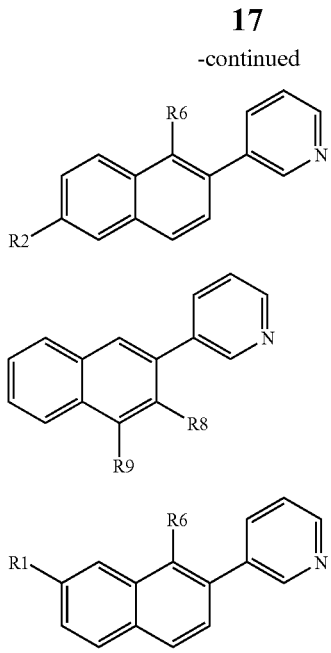

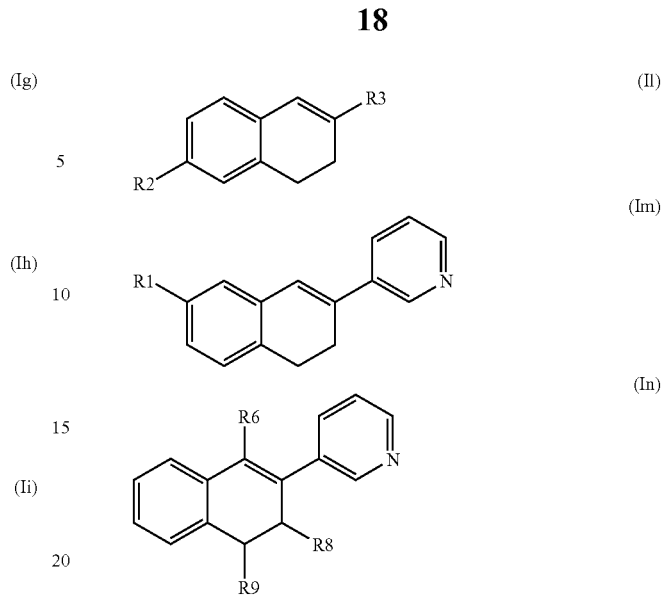

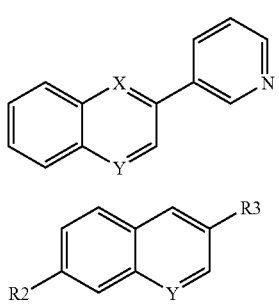

wherein $R^1$ and $R^2$ are preferably independently selected from the group consisting of H, halogen, CN, hydroxy, O-lower alkyl, O-lower alkenyl, O-lower alkinyl, lower alkyl, lower alkenyl, lower alkinyl, —COOR$^{11}$, —CON(R$^{11}$)$_2$ and arylalkyloxy residues, and more preferably are H, O-lower alkyl and arylalkoxy;

$R^5$ is selected from the group consisting of H, halogen, heteroaryl;

$R^6$ is selected from H and halogen;

$R^8$ and $R^9$ are selected from H and alkyloxy, or together form an anellated aryl ring, preferably a benzyl ring;

and pharmaceutically acceptable salts thereof.

Preferred embodiments of compound (Ib) are the compounds of the following formulas (Ij) and (Ik):

wherein X and Y are selected from N and C, but the naphthalene skeleton preferably contains at least one nitrogen atom;

$R^3$ is selected from pyridyl, pyrimidyl, imidazolyl, oxazolyl, preferably pyridyl and imidazolyl;

$R^2$ is selected from H, halogen, CN, O-lower alkyl, O-lower alkenyl, O-lower alkinyl, lower alkyl, lower alkenyl or lower alkinyl, and preferably is H or O-lower alkyl, and pharmaceutically acceptable salts thereof.

Preferred embodiments of compound (Ic) are the compounds of the following formulas (Il) and (In):

wherein $R^1$ and $R^2$ are preferably selected from H and O-lower alkyl;

$R^3$ is pyridyl or imidazolyl;

$R^6$, $R^8$ and $R^9$ are H or lower alkyl, preferably one of these substituents being lower alkyl, more preferably methyl, and the other two being H;

and pharmaceutically acceptable salts thereof.

Preferred embodiments of compound (Id) are the compounds in which $R^2$ and $R^5$ are independently H or O-lower alkyl;

$R^3$ is pyridyl or imidazolyl, preferably 3-pyridyl or 1-imidazolyl; and pharmaceutically acceptable salts thereof.

In all embodiments of the invention, $R^3$ is even more preferably 3-pyridyl. In particular, preferred compounds of formula (I) for embodiments (1), (2) and (3) include the following compounds: 3-(2-naphthyl)pyridine; 3-(1-chloro-7-methoxy-2-naphthyl)pyridine; 3-(1,5-dichloro-6-methoxy-2-naphthyl)pyridine; 3-(3-methoxy-2-naphthyl)pyridine; 3-(5-chloro-6-methoxy-2-naphthyl)pyridine; 3-(5-bromo-6-methoxy-2-naphthyl)pyridine; 3-(6-methoxy-2-naphthyl)pyridine; 3-(6-ethoxy-2-naphthyl)pyridine; 3-(6-bromo-2-naphthyl)pyridine; 3-(7-methoxy-2-naphthyl)pyridine; 5-(6-methoxy-2-naphthyl)pyrimidine; methyl-6-pyridin-3-yl-2-naphthoate; 6-pyridin-3-yl-2-naphthonitrile; 6-pyridin-3-yl-2-naphthol; 2-pyridin-3-yiquinoline; 3-pyridin-3-ylquinoline; 1-(2-naphthyl)-1H-imidazol; 1-(3-methoxy-2-naphthyl)-1H-imidazol; 5-(2-naphthyl)-1H-imidazol; 3-(3,4-dihydronaphthalene-2-yl)pyridine; 3-(1-methyl-3,4-dihydronaphthalene-Z-yl)pyridine; 3-(3-methyl-3,4-dihydronaphthalene-2-yl)pyridine; 3-(4-methyl-3,4-dihydronaphthalene-2-yl)pyridine; 3-(6-methoxy-3,4-dihydronaphthalene-2-yl)pyridine; 3-(7-methoxy-3,4-dihydronaphthalene-2-yl)pyridine; 3-(1H-inden-2-yl)pyridine; 3-(6-methoxy-1H-inden-2-yl)pyridine and 3-(1-ethyl-3,4-dihydronaphthalene-2-yl)pyridine.

Particularly preferred are 3-(2-naphthyl)pyridine; 3-(6-methoxy-2-naphthyl)-pyridine; 3-(6-bromo-2-naphthyl)pyridine; 3-(6-ethoxy-2-naphthyl)pyridine; 6-pyridin-3-yl-2-naphthonitrile; 3-(1,5-dichloro-6-methoxy-2-naphthyl)pyridine; methyl-6-pyridin-3-yl-2-naphthoate; 3-(1H-inden-2-yl)pyridine; 3-(3,4-dihydronaphthalene-2-yl)pyridine; 3-(6-methoxy-1H-inden-2-yl)pyridine; 3-(6-methoxy-3,4-dihydronaphthalene-2-yl)pyridine; 3-(1-methyl-3,4-dihydronaphthalene-2-yl)pyridine; 3-(3-methyl-3,4-dihydronaphthalene-2-yl)pyridine; and 3-(1-ethyl-3,4-dihydronaphthalene-2-yl)pyridine and especially 3-(6-methoxy-2-naphthyl)pyridine; 3-(6-bromo-2-naphthyl) pyridine; 3-(6-ethoxy-2-naphthyl)-pyridine; 6-pyridin-3-yl-2-naphthonitrile; 3-(1H-inden-2-yl)pyridine; 3-(3,4-dihydronaphthalene-2-yl)pyridine; 3-(6-methoxy-1H-inden-2-yl)pyridine; 3-(6-methoxy-3,4-dihydronaphthalene-2-yl) pyridine; 3-(1-methyl-3,4-dihydronaphthalene-2-yl)pyridine and 3-(3-methyl-3,4-dihydronaphthalene-2-yl)pyridine.

Most preferred are 3-(6-methoxy-2-naphthyl)pyridine, 6-pyridin-3-yl-2-naphthonitrile, 3-(6-methoxy-1H-inden-2-yl)pyridine, 3-(6-methoxy-3,4-dihydronaphthalene-2-yl)pyridine, 3-(1-methyl-3,4-dihydronaphthalene-2-yl)pyridine and 3-(3-methyl-3,4-dihydronaphthalene-2-yl)pyridine.

In one aspect of the process according to embodiment (4), the chemical compounds according to the invention, especially the compounds of embodiment (3), can be synthesized by a Suzuki coupling of compound (III) with compound (II) (cf. Examples 1 and 2). The process is preferably effected according to the following general synthesis scheme:

The reaction products can be converted to stable salts thereof, preferably to HCl salts or pharmaceutically acceptable salts.

The synthesis according to the invention can be used for the preparation of the compounds according to the invention and similar compounds. In some cases, the yields are clearly increased by the synthesis according to the invention over that of previously known methods (by up to 40%). Thus, the yield for 4-(6-methoxy-3,4-dihydronaphthalene-2-yl)pyridine 43 is 21% in the literature (Kelley, C. J. et al., J. Het. Chem. 38(1): 11-23 (2001)), while it is 61% when the synthesis according to the invention is applied.

For synthesis (4) for the preparation of compounds with substituents or functional groups of the heterocyclic compounds that can be deprotonated, it is required to provide them with appropriate protecting groups. Suitable protecting groups and their removal are available to the skilled person, for example, from T. W. Green, Protective Groups in Organic Synthesis, Harvard University, John Wiley & Sons (1981).

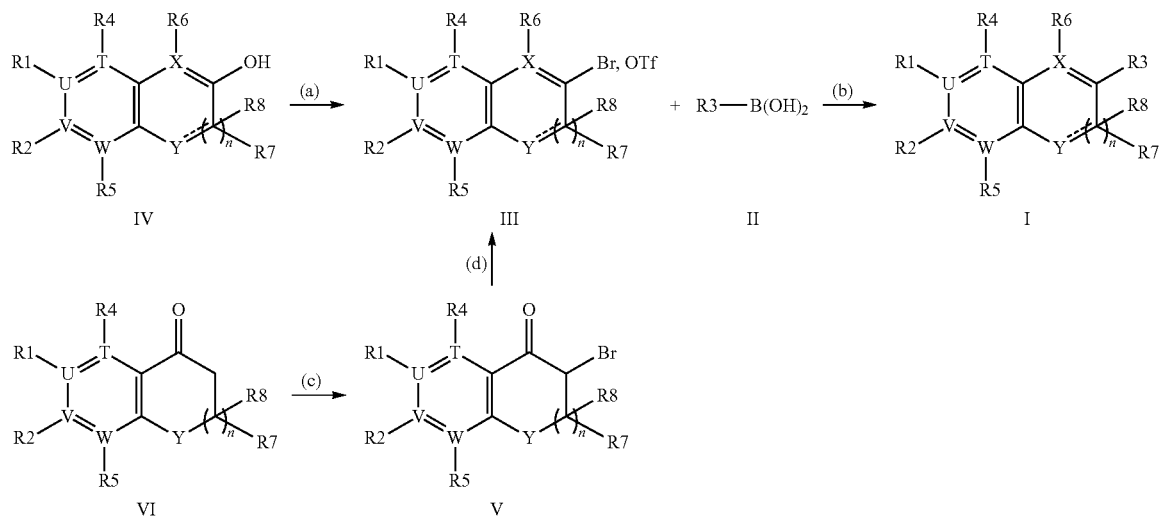

Reaction conditions: (a) (CF$_3$SO$_2$)$_2$O, pyridine, 30 min at 0° C. and over night at RT;
(b) Pd(PPh$_3$)$_4$, Na$_2$CO$_3$, toluene or DME, 80° C.;
(c) TBABr$_3$, CH$_2$Cl$_2$, RT;
(d) 1) NaBH$_4$, MeOH, 0° C.; 2) pTSA, toluene, reflux.

The key step of this synthesis is the Suzuki coupling of different heterocyclic boronic acids with bromo- or triflate-substituted bicyclic compounds. In a first step, the triflates (III) are synthesized from the corresponding alcohols (IV) by a reaction with trifluoromethanesulfonic anhydride and pyridine. In the second step, the bromine or triflate compounds (III) and the heterocyclic boronic acids (II) are coupled by a Suzuki reaction with Pd(PPh$_3$)$_4$ as a catalyst, Na$_2$CO$_3$ as a base and toluene or DME as a solvent. After processing, the products are purified by column chromatography and characterized by NMR.

In another aspect of the process according to embodiment (4), the compounds (III) which are necessary for the synthesis of the chemical compounds according to the invention can be prepared by a TBABr$_3$ treatment of ketones (VI), by which they are converted to the corresponding α-bromoketones (V) (Example 2). After reduction with NaBH$_4$, the resulting alcohols are refluxed in toluene with addition of a catalytic amount of pTSA to form the dehydratized bromine compounds (III). The final step is the above described Suzuki coupling of bromine compounds (III) with compounds (II).

This means of course that a downstream deprotection step is necessary if such protecting groups are used in the process (4) according to the invention.

The testing of the compounds according to the invention for usefulness according to embodiments (1) and (5) is effected on in vitro test systems, preferably on more than one in vitro test system. The first step comprises the testing with human CYP11B enzymes, preferably human CYP11B1 and CYP11B2. These human enzymes can be either expressed recombinantly, especially in Schizosaccharomyces pombe or V79 cells, or be contained in a tested human cell line, especially the adrenocortical tumor cell line NCI-H295R (cf. Examples 4 and 8). More preferably, substances that show activity on human CYP11B enzymes are employed for the inventive use according to (1) or (5). For the identification of novel therapeutically active compounds according to embodiment (1) for humans, fission yeast and V79MZh cells that express CYP11B1 and CYP11B2 recombinantly and NCI-H295R cells are suitable, in particular.

For the inhibition of human CYP11B2 according to the inventions those com-pounds whose selectivity factor (IC$_{50}$ CYP11B1/IC$_{50}$ CYP11B2) is higher than 50 are particularly suitable, more particularly those whose IC$_{50}$ CYP11B2 is smaller than 20 nM.

Especially the 3-pyridyl-substituted naphthalene derivatives and 3,4-dihydronaphthalenes according to embodiment (1) are suitable for use according to (1) and (5). For the selective inhibition of CYP11B2 according to embodiment (5), these are, in particular, the naphthalene derivatives 2, 4, 5 and 10 and the dihydronaphthalene derivatives 24, 33, 1 35 and 38 (cf. Examples 6-7) of the present invention. Even more preferred are 3-(6-methoxy-2-naphthyl)pyridine 2 and 3-(6-methoxy-3,4-dihydronaphthalene-2-yl)pyridine 35 (Example 6); the latter is a highly potent CYP11B2 inhibitor (IC$_{50}$: 2 nM) that has a 100 fold selectivity as compared to CYP11B1 (IC$_{50}$: 213 nM). In addition, this compound is a promising lead structure for further therapeutic agents.

For the selective inhibition of CYP11B1 according to embodiment (5), the compounds 27, 29, 45 and 46 are particularly suitable (cf. Examples 5-6). These compounds exhibit a very low CYP11B2 inhibition in *S. pombe* (Example 4A) (cf. Examples 5-6). With IC50 values of from 206 to 805 nM in V79MZh 11B1 cells, they exhibit good inhibitor properties. Even more preferred is 4(5)-(2-naphthyl)-1-H-imidazole 27. With an IC50 value of 206 nM, it has the strongest CYP11B1 inhibition while the CYP11B2 inhibition is moderate (41%).

To determine the inhibition of human CYP11B2 by the test compounds, a screening test in recombinant *S. pombe*, especially CYP11B2-expressing *S. pombe* P1, can be used (Example 4A). For a further testing for usefulness according to use (5), especially those compounds are selected thereafter that exhibit a higher inhibitory effect than that of the reference fadrozole.

In the second step, compounds can be tested for usefulness according to (5) in V79 MZh cells (hamster lung fibroblasts) that express either CYP11B1 or CYP11B2 for their activity and selectivity (Example 4B). Different inhibition profiles are found: Inhibitors that are selective for either CYP11B1 or CYP11B2, and inhibitors that can inhibit both CYP11B enzymes.

The inhibition of CYP19 by the test compounds can be performed in vitro using human placental microsomes and [1β,2β-³H]testosterone as the substrate (modified from: Thompson, E. A. Jr. & Siteril, P. K., J. Biol. Chem. 249: 5364-5372 (1974)) (Example 3).

The inhibition of CYP17 by the test substances can be determined in vitro by means of a CYP17-containing membrane fraction from *E. Coli* that recombinantly expresses CYP17 and progesterone as the substrate (Example 3).

The NCI H295R cell line is commercially available and is frequently used as a model for the human adrenal cortex. The cells were isolated for the first time in 1980 (Gazdar, A. F. et al., Cancer Res. 50: 5488-5496 (1990)) and contain 5 steroidogenic CYP450 enzymes including 17-alpha-hydroxylase, CYP1151 and CYP11B2. Since all the steroidogenic CYP enzymes occurring in the adrenal cortex are expressed in this cell line, it is an important instrument in the estimation of the selectivity of inhibitors in vitro. Consequently, an essential difference to the V79 cells is not only the fact that NCI-H295R are human cells, but also the fact that only one target enzyme each is present in V79MZh11B1 and V79MZh11B2, recombinantly expressed in a system that is otherwise completely free of CYP enzymes, while NCI-H295R is a substantially more complex model. By means of this new model, the prediction of effects and side effects of compounds on the complex enzymes of the adrenal cortex can become clearly more precise.

The influence of the substances found in the present invention on human CYP11B1 and CYP11B2 in NCI-H295R cells was tested for the first time by using just a few compounds in an exemplary manner (Example 8).

Using the NCI-H295R cell line, another test system has been established for evaluating the substances according to the invention (Example 9). The background of this test system is the fact that H295R expresses within the cell all the steroidogenic CYP enzymes necessary for the synthesis of the adrenal steroids. In contrast, in the intact human adrenal cortex, the production of the mineral corticoids is effected in the zona glomerulosa, that of the glucocorticoids is effected in the zona fasciculata, and that of the adrenal androgens is effected in the zona reticularis. In H295R, there are no such zones, but nevertheless the concentrations of steroids secreted by H295R are comparable qualitatively and quantitatively with the concentrations released by the intact human adrenal cortex.

In this model, the cortisol production is inhibited more strongly than the aldosterone production if compound 2 is employed as the test substance (Example 9, Table 5). This circumstance can be used for also using indirect inhibitors of CYP11B1 according to embodiment (5) for the preparation of medicaments according to embodiment (2) for the therapy of hypercortisolism and diabetes mellitus. A reason for the indirect inhibition by compound 2, which is very selective for CYP11B2 in the V79MZ system, may be the affinity of this compound for CYP17, which is highly active in H295R. Possibly, the inhibition of CYP17 results in an accumulatin of its substrates progesterone and pregnenolone. Consequently, the degradation of these steroids can go via the CYP21 and CYP11B2 pathways, which in turn results in increased concentrations of the CYP11B2 substrate DOC. Then, CYP11B2 inhibitors compete with these increased concentrations of DOC for the binding sites on the active site of the protein, which results in higher IC$_{50}$ values. In addition, inhibition of CYP17 additionally leads to a lowering of the CYP11B1 substrate RSS and to reduced IC$_{50}$ values of this enzyme. Consequently, this cascade can mask a selective CYP11B2 inhibition in this test system. Thus, from a systemic point of view, the compounds according to the invention can significantly influence steroidogenesis beyond the direct effect on individual enzymes.

In first experiments, the in vivo activity of the compounds presented here could be shown on a rat model. Fadrozole lowers the aldosterone and corticosterone concentrations in ACTH-stimulated rats (Häusler et al., J. Steroid Biochem. 34: 567-570 (1989)). Some of the compounds presented here showed a behavior in vivo that was similar to that of fadrozole.

The substances of formula (I) that are suitable for use according to embodiment (5) can serve for the development of a medicament containing a pharmaceutical formulation according to embodiment (2) which improves the quality of life of patients with heart failure or myocardial fibrosis and can critically reduce mortality. The results of the present invention clearly show that it is possible to develop inhibitors for the target enzyme CYP11B2 that are highly active, but only have a little influence on CYP11B1, which has a high structural and functional homology with CYP11B2, and vice versa.

The pharmaceutical composition according to embodiment (2) preferably contains one of those compounds of formula (I) that are preferably employed for the use according to embodiment (1). It is suitable for the therapy of hyperaldosteronism, heart failure or myocardial fibrosis, hypercortisolism, diabetes mellitus, depression, age-related cognitive decline and metabolic syndrome in mammals and especially in humans.

As single compounds and in combination with other active substances and auxiliary agents, the compounds according to the invention are suitable, for example, for the inhibition of human and mammal P450 oxygenases, especially for the inhibition of human or mammal aldosterone synthase, more particularly for the inhibition of the human aldosterone synthase CYP11B2 while human CYP11B1 is little affected, and conversely for the inhibition of CYP11B1 while CYP11B2 is little affected, in vitro and in vivo. The compounds selective for CYP11B2 can be employed for the preparation of medicaments for the therapy of heart failure (myo)cardial fibrosis, (congestive) heart failure, hypertension and primary hyperaldosteronism in humans and mammals. The compounds selective for CYP11B1 are steroid hydroxylase inhibitors, especially steroid 11β-hydroxylase inhibitors, that can be employed for the preparation of medicaments for the therapy of hypercortisolism, diabetes mellitus, especially diabetes mellitus type II, depression, age-related cognitive decline and metabolic syndrome.

In addition to the compounds according to the invention, these medicaments or pharmaceutical compositions according to embodiment (2) of the invention may contain other active substances as well as appropriate auxiliary agents and carriers. Appropriate auxiliary agents and carriers are determined by the skilled person as a function of the field of application and dosage form.

In addition, the invention includes a process and the use of the compound according to the invention for the prevention, slowing of the progress or therapy of one of the following diseases or clinical pictures: diabetes mellitus, hyperaldosteronism, hypercortisolism, hypertension, congestive heart failure, kidney failure, especially chronic kidney failure, restenosis, atherosclerosis, nephropathy, coronary heart diseases, increased formation of collagen, fibrosis, depression, age-related cognitive decline and metabolic syndrome, respectively associated or not with occurrence of hypertension, by administering a pharmaceutical formulation according to the invention.

In a preferred embodiment, this process is suitable for the prevention, slowing of the progress or therapy of hyperaldosteronism, myocardial fibrosis, congestive heart failure or congestive heart insufficiency and comprises the administration of an effective dose of an aldosterone synthase inhibitor according to the invention or a pharmaceutically acceptable salt thereof to the afflicted human or mammal.

In a further preferred embodiment, this process is suitable for the prevention, slowing of the progress or therapy of stress-dependent therapy-resistant diabetes mellitus, especially of type II, hypercortisolism, depression, age-related cognitive decline or metabolic syndrome and comprises the administration of an effective dose of a steroid hydroxylase inhibitor according to the invention, especially steroid 11β-hydroxylase inhibitor, or a pharmaceutically acceptable salt thereof to the afflicted human or mammal.

The compounds of the present invention can be administered in any dosage form familiar to the skilled person, oral administration being the preferred form of administration.

The amount of active substance administered, i.e., the dose employed, depends on the kind and severeness of the disease to be treated, the dosage form and form of therapy, the age and constitution of the patient and is adapted individually to the prevailing situation by the attending physician on the basis of their general technical knowledge.

The invention is further illustrated by means of the following Examples which do not limit the invention, however.

EXAMPLES

Material and Analytical Methods

IR spectra were recorded on a Bruker Vector 33 Fr-infrared spectrometer. $^1$H NMR spectra were recorded on a Bruker DRX-500 (500 MHz) instrument. Chemical shifts are stated in parts per million (ppm). All coupling constants (3) are stated in Hz. The reagents and solvents were derived from commercial sources and used without further purification. Column chromatography (CC) was performed over silica gel (70-200 μm), the course of the reaction was monitored by means of thin-layer chromatography over ALUGRAM SIL G/UV$_{254}$ plates (Macherey-Nagel, Düren, Germany).

Example 1

Synthesis of Compounds 1 to 31

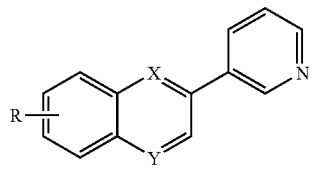

1-21

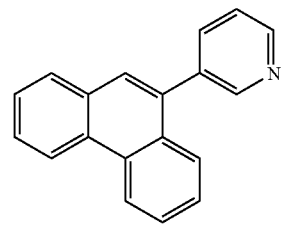 [SMILES: c1cncc(-c2cc3ccccc3c3ccccc23)c1]

22

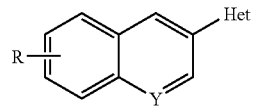

23-31

| No. | R | X/Y |
|---|---|---|
| 1 | H | CH |
| 2 | 6-OMe | CH |
| 3 | 6-OH | CH |
| 4 | 6-Br | CH |
| 5 | 6-OEt | CH |
| 6 | 6-OPr | CH |
| 7 | 6-OBn | CH |
| 8 | 6-CN | CH |
| 9 | 5-Cl-6-OMe | CH |
| 10 | 5-Br-6-OMe | CH |
| 11 | 5-Pyr-6-OMe | CH |
| 12 | 1,5-Cl, 6-OMe | CH |
| 13 | 7-OMe | CH |
| 14 | 1-Cl-7-OMe | CH |
| 15 | 3-OMe | CH |
| 16 | 6-COOMe | CH |
| 17 | 6-CONH$_2$ | CH |
| 18 | 6-CONHMe | CH |

-continued

| no | R | X | Y |
|---|---|---|---|
| 19 | H | CH | N |
| 20 | H | N | CH |
| 21 | H | N | N |

| No. | R | Y | Het |
|---|---|---|---|
| 23 | H | CH | 1-imidazolyl |
| 24 | 3-OMe | CH | 1-imidazolyl |
| 25 | 6-OMe | CH | 1-imidazolyl |
| 26 | H | N | 1-imidazolyl |
| 27 | H | CH | 4(5)-imidazolyl |
| 28 | H | CH | 5-(N-methyl)imidazolyl |
| 29 | H | CH | 5-oxazolyl |
| 30 | 6-OMe | CH | 5-pyrimidyl |
| 31 | 6-OMe | CH | 4-pyridyl |

The synthesis was effected according to the general synthesis scheme.

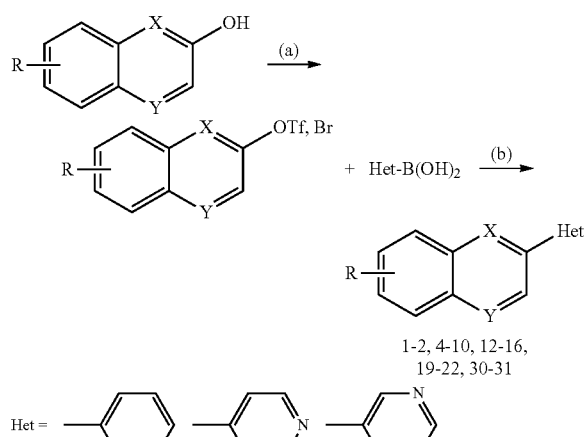

Reaction conditions: (a) (CF$_3$SO)$_2$O, pyridine, 30 min at 0° C., over night at RT; (b) Pd(PPh$_3$)$_4$, Na$_2$CO$_3$, toluene or DME, 80° C.

The key step of the synthesis was the Suzuki coupling of different heterocyclic boronic acids with bromine or triflate compounds. In a first step, the triflates (III) were synthesized from the corresponding alcohols (IV) by a reaction with trifluoromethanesulfonic anhydride and pyridine. The bromine compounds were commercially available are were prepared as described under (A). In the second step, the bromine or triflate compounds (III) and the heterocyclic boronic acids (II) were coupled by a Suzuki reaction with Pd(PPh$_3$)$_4$ as a catalyst, Na$_2$CO$_3$ as a base and toluene or DME as a solvent. The mixture obtained after the reaction was purified by column chromatography. The products were characterized by NMR.

A) Synthesis of the Non-Commercially Available Precursors:

The following compounds were prepared by new or known synthetic methods:

2-Bromo-6-ethoxynaphthalene 5i, 2-bromo-6-propoxynaphthalene 6i and 2-bromo-6-phenoxynaphthalene 7l were prepared by analogy with Huisgen et al. (slightly modified) (Huisgen, R. and Sorge, G., Liebigs Ann. Chem. 566: 162-184 (1950)):

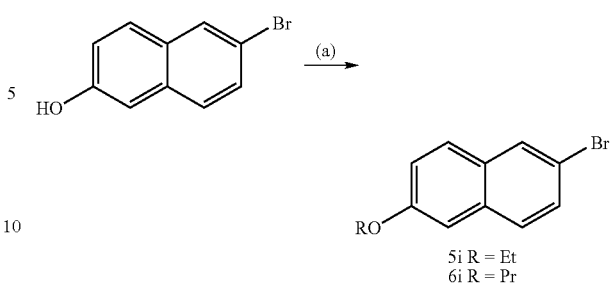

Reaction conditions: (a) RBr, K$_2$CO$_3$, DMF, 3 h, reflux

6-Bromo-1-chloro-2-methoxynaphthalene 9i and 1,6-dibromo-2-methoxynaphthalene 10i (new synthetic method):

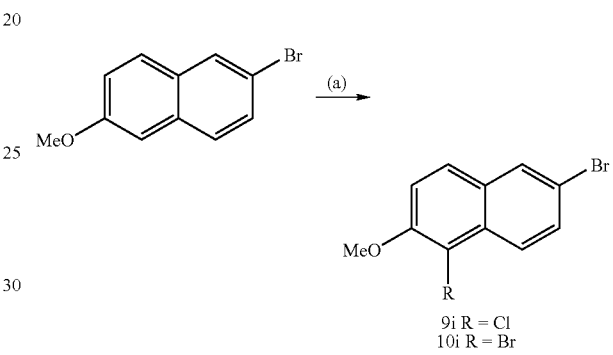

Reaction conditions: (a) NBS or NCS, THF, 3 h reflux, over night at RT 1,5-Dichloro-6-methoxy-2-naphthol 12ii was prepared by analogy with WO 03/051805:

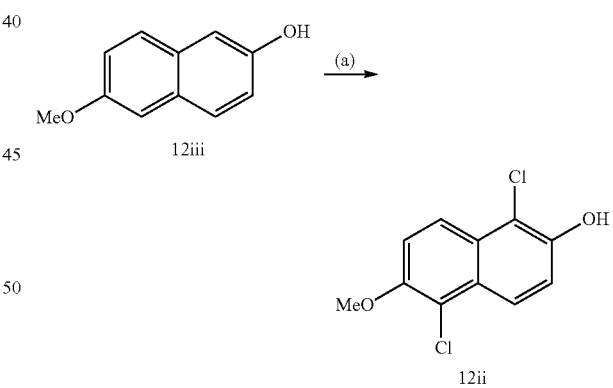

Reaction conditions: (a) NCS, ACN, over night at RT

1-Chloro-7-methoxy-2-naphthol 14ii was synthesized in one step (new synthetic method):

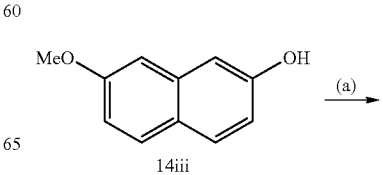

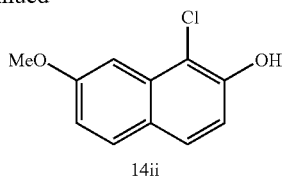

14ii

Reaction conditions: (a) NCS, ACN, over night at RT

6-Cyano-2-naphthyltrifluoromethanesulfonate 8i, 1,5-dichloro-6-methoxy-2-naphthyltrifluoromethanesulfonate 12i (WO 03/051805), 7-methoxy-2-naphthyltrifluoromethanesulfonate 13i (WO 03/051805) and 1-chloro-7-methoxy-2-naphthyltrifluoromethanesulfonate 14i:

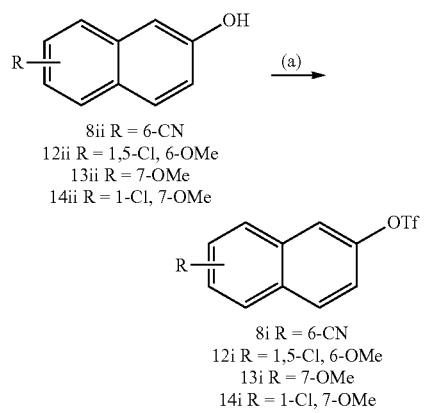

8ii R = 6-CN
12ii R = 1,5-Cl, 6-OMe
13ii R = 7-OMe
14ii R = 1-Cl, 7-OMe

8i R = 6-CN
12i R = 1,5-Cl, 6-OMe
13i R = 7-OMe
14i R = 1-Cl, 7-OMe

Reaction conditions: (a) Trifluoromethanesulfonic anhydride, pyridine, 30 min at 0-5° C., over night at RT 2-Bromoquinoline 20i (Young, T. E. and Amstutz, E. D., JACS, 4773-5 (1951)) and 2-bromoquinoxaline 21i were prepared by reacting the corresponding alcohol with POBr$_3$:

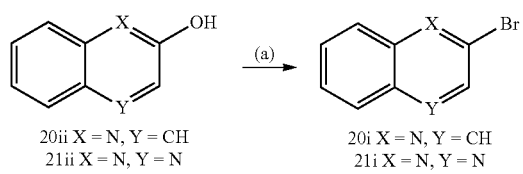

20ii X = N, Y = CH
21ii X = N, Y = N

20i X = N, Y = CH
21i X = N, Y = N

Reaction conditions: (a) POBr$_3$, 4 h, 150° C.

O-Methoxynaphthylboronic acid 24i was prepared by a known synthetic method (Chowdhury, S. et al., Tet. Lett. 40(43); 7599-7603 (1999)):

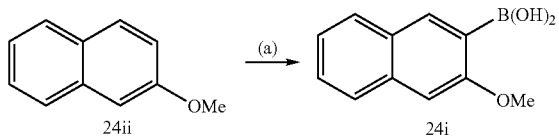

24ii

24i

Reaction conditions: (a) 1) nBuLi, THF, -20° C.; 2) B(OMe)$_3$, THF, -78° C.

N-Benzylidenemethylamine 28i was prepared as described (H. Dahn and P. Zoller, Helv. Chim. Acta 35: 1348-1351 (1952)):

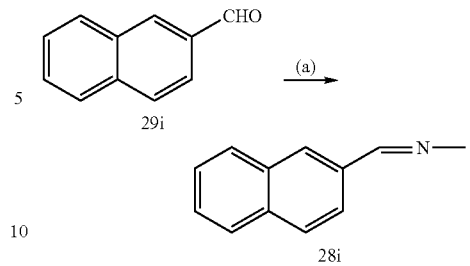

28i

Reaction conditions: (a) MeNH$_2$, EtOH, reflux, 1 h.

B) Synthesis of Compounds 1-31:

General Synthesis of Compounds 1-2, 4-10, 12-16, 19-22, 30-31:

A mixture of substituted 2-bromonaphthalene or 2-trifluoromethanesulfonate (1 eq), heterocyclic boronic acid (1.3 eq), sodium carbonate (2.1 eq) and tetrakis(triphenylphosphin) palladium (0.02 eq) in ethylene glycol dimethyl ether or toluene was stirred over night at 80° C. under a nitrogen atmosphere. After cooling to room temperature (RT), water was added. The mixture was extracted with ethyl acetate, dried over MgSO$_4$, filtered, and the solvent was removed under vacuum. After purification by column chromatography, the yields were up to 940%.

Synthesis of 6-pyridin-3-yl-2-naphthol 3

Demethylation of compound 2 by BBr$_3$ in dichloromethane at -78° C. yielded the hydroxylated compound 3:

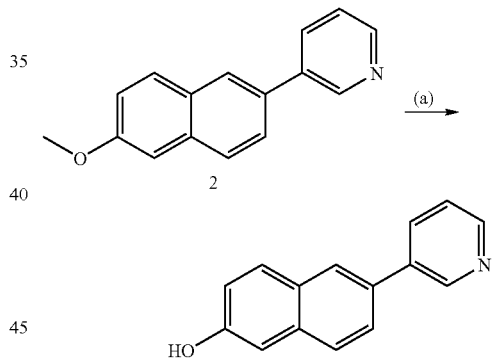

Reaction conditions: (a) BBr$_3$, CH$_2$Cl$_2$, -78° C.

At -78° C. under a nitrogen atmosphere, BBr$_3$ (0.85 ml, 0.85 mmol) was added slowly to compound 2 (50 mg, 0.21 mmol) in 6 ml of dry CH$_2$Cl$_2$. After stirring for 30 min, the cooling was discontinued, and the mixture was stirred over night at RT. Then, the reaction was quenched by slowly adding methanol. The mixture was washed with a saturated sodium bicarbonate solution, the organic phase was dried over MgSO$_4$, filtered off, and the solvent was removed under vacuum.

Synthesis of 3-(5-bromo-6-methoxy-2-naphthyl) pyridine 10 and 3,3'-(2-methoxynaphthalene-1,6-diyl)dipyridine 11

The Suzuki coupling of 10i with two equivalents (eq) of 3-pyridylboronic acid (catalyst: Pd(PPh$_3$)$_4$; base: Na$_2$CO$_3$) yielded a mixture of mono(10)- and di(11)pyridyl-substituted naphthalenes:

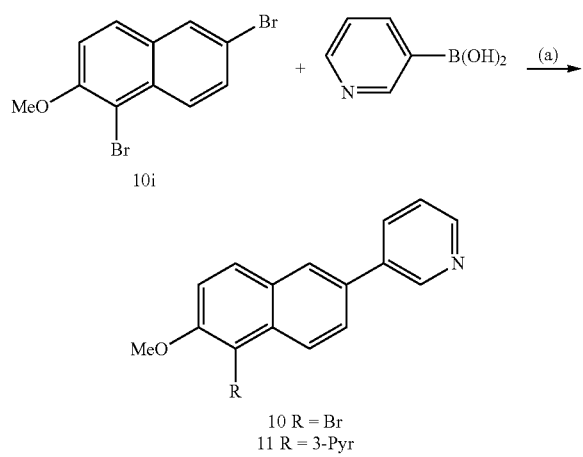

10 R = Br
11 R = 3-Pyr

Reaction conditions: (a) PdP(Ph₃)₄, Na₂CO₃, DME, 80° C.

A mixture of 1,6-dibromo-2-methoxynaphthalene 10i (223 mg, 0.71 mmol), 3-pyridineboronic acid (260 mg, 2.12 mmol), sodium carbonate (299 mg, 2.82 mmol) and tetrakis (triphenylphosphine)palladium (16 mg) in ethylene glycol dimethyl ether was stirred in a nitrogen atmosphere at 80° C. over night. The mixture was cooled down to RT, and water was added. After extraction with ethyl acetate, the organic phase was dried over MgSO₄, filtered, and the solvent was removed under vacuum. The product was purified by column chromatography, CH₂Cl₂/MeOH (98:2) serving as the eluent.

Synthesis of Compounds 17, 18:

According to a literature method (Iagdmann, G. E. et al., Synth. Comm. 20(8): 1203-1208 (1990)), the carboxylate ester 16 was converted to primary or secondary amines with the corresponding formamides and NaOMe as the base in anhydrous DMF:

17 R = H
18 R = Me

Reaction conditions: (a) RNHCHO, NaOMe, DMF, 100° C.

With stirring, a mixture of methyl-6-bromo-2-naphthoate 16 (1 eq) and formamide (3.3 eq) under nitrogen was admixed with anhydrous DMF (2 ml) and heated at 100° C. Methanolic sodium methanolate (0.7 eq) was added, and stirring of the mixture was continued for 1 h. After cooling and adding water (2 ml), the mixture was extracted with ethyl acetate, the organic phase was dried over MgSO₄, filtered, and the solvent was removed under vacuum.

Synthesis of Compounds 23-25:

The 1-imidazolyl-substituted naphthalenes 23-25 were prepared by coupling naphthylboronic acid with imidazole in the presence of a catalytic amount of a copper salt (Lam, P. Y. S. et al., Tet. Lett. 39: 2941-4 (1998); Lan, J.-B. et al., Chem, Commun., 188-9 (2004)):

23i-25i 23-25

Reaction conditions: (a) Imidazole, Cu(OAc)₂, pyridine, CH₂Cl₂, RT; or Imidazole, CuI, 2 h, reflux A mixture of naphthaleneboronic acid 23i or 25i (2 eq), imidazole (1 eq), copper(II) acetate (1.5 eq), pyridine (2 eq) and a 4 Å molecular sieve in anhydrous dichloromethane was stirred at RT for two days. The mixture was filtered off, and the solvent was removed under vacuum. The product was purified by column chromatography. A mixture of naphthaleneboronic acid 24i (1 eq), imidazole (1.2 eq) and copper iodide (5 mole percent) in anhydrous methanol was refluxed in air for 2H. The solvent was removed under vacuum. The product was purified by column chromatography.

Synthesis of Compound 26:

3-(1H-Imidazol-1-yl)quinoline 26 was prepared as described by Kauffmann et al. (Kauffmann, T. et al., Chem. Ber. 115: 452-8 (1982)):

19i    26

Reaction conditions: (a) Imidazole, CuO, K₂CO₃, nitrobenzene, 24 h, reflux

Synthesis of Compound 27:

Treatment of the c-bromoketone 27i with formamide at a high temperature yielded 4(5)-(2-naphthyl)-1H-imidazole 27 according to a method of Bredereck and Theilig (Bredereck, H. and Theilig, G., Chem. Ber. 86: 88-96 (1953)):

27i

-continued

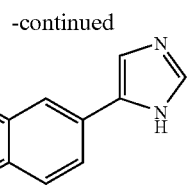

27

Reaction conditions: (a) NH₂CHO, 185° C., 2 h

Synthesis of Compounds 28, 29:

Reaction of N-benzylidenemethylamine 28i or 2-naphthaldehyde 29i and tosylmethylisocyanide (Tosmic) with $K_2CO_3$ as the base yielded 1-methyl-5-(2-naphthyl)-1H-imidazole 28 or 5-(2-naphthyl)-1,3-oxazole 29, respectively:

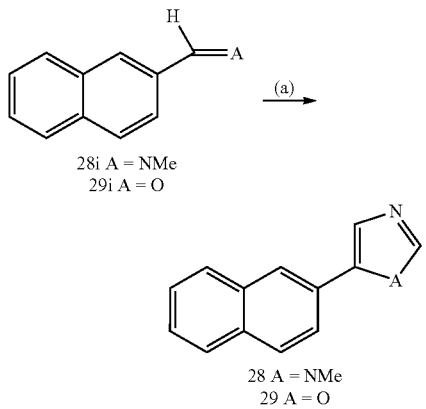

28i A = NMe
29i A = O

28 A = NMe
29 A = O

Reaction conditions: (a) Tosmic, $K_2CO_3$, RT

A mixture of N-benzylidenemethylamine 28i or 2-naphthaldehyde 29i (1 eq), tosylmethylisocyanide (1.7 eq) and potassium carbonate (2 eq) in absolute methanol was stirred at RT over night. Methanol was removed under vacuum, and dichloromethane was added to the raw product. After washing with water, the organic phase was dried over $MgSO_4$, filtered, and the solvent was removed under vacuum. The product was purified by column chromatography.

C) Purification Conditions, Yield and Characterization of the Title Compounds:

3-(2-Naphthyl)pyridine (1). Purification: Column chromatography (CC) ($CH_2Cl_2$/MeOH, 97:3) yield 16%. $^1$H NMR (500 MHz, CDCl$_3$): δ 7.44 (dd, 1H, $^3$J=8.2 Hz, $^4$J=Hz, Pyr. H-5), 7.51-7.56 (m, 2H, Ar H), 7.71 (dd, 1H, $^3$J=8.5 Hz, $^4$J=1.6 Hz, Ar H), 7.88-7.90 (m, 2H, Ar H), 7.96 (d, 1H, $^3$J=8.5 Hz, Ar H), 8.03-8.05 (m, 2H, Ar H, Pyr. H-4), 8.63 (dd, 1H, $^3$J=4.7 Hz, $^4$J=1.6 Hz, Pyr. H-6), 8.99 (dd, 1H, $^4$J=1.6 Hz, Pyr.H-2). IR cm$^{-1}$: ν$_{max}$3392, 3051, 3029, 1599, 1484. MS m/z 206 (MH$^+$), 178, 151, 77, 51.

3-(6-Methoxy-2-naphthyl)pyridine (2). Purification: CC($CH_2Cl_2$/MeOH, 97:3) yield 77%. $^1$H NMR (500 MHz, CDCl$_3$): δ 3.95 (s, 1H, OCH$_3$), 7.17 (d, 1H, $^4$J=2.5 Hz, Ar H), 7.22 (dd, 1H, $^3$J=8.8 Hz, $^4$J=2.2 Hz, Ar H), 7.45-7.47 (m, 1H, Pyr. H-5), 7.67 (dd, 1H, $^3$J=8.5 Hz, $^4$J=1.8 Hz, Ar H), 7.81 (d, 1H, $^3$J=8.5 Hz, Ar H), 7.85 (d, 1H, $^3$J=8.5 Hz, Ar H), 7.98 (s, 1H, Ar H), 8.04-8.06 (m, 1H, Pyr. H-4), 8.61 (dd, 1H, $^3$J=4.7 Hz, $^4$J=1.3 Hz, Pyr. H-6), 8.97 (s, 1H, Pyr. H-2). IR cm$^{-1}$: ν$_{max}$ 3058, 2938, 1605, 1489. MS m/z 236 (MH$^+$).

6-Pyridin-3-yl-2-naphthol (3). Purification: CC($CH_2Cl_2$/ MeOH, 98:2) yield 65%. $^1$H NMR (500 MHz, CDCl$_3$): δ 7.20 (dd, 1H, $^3$J=8.8 Hz, $^4$J=2.2 Hz, Ar H), 7.23 (d, 1H, $^4$J=1.9 Hz, Ar H), 7.62 (m, 1H, Pyr. H-5), 7.83 (dd, 1H, $^3$J=8.5 Hz, $^4$J=1.6 Hz, Ar H), 7.87 (d, 1H, $^3$J=8.8 Hz, Ar H), 7.92 (d, 1H, $^3$J=8.8 Hz, Ar H), 8.24 (s, 1H, Ar H), 8.29 (dt, 1H, $^3$J=7.9 Hz, $^4$J=1.9 Hz, Pyr. H-4), 8.65 (d, 1H, $^3$J=4.7 Hz, Pyr. H-6), 9.08 (d, 1H, $^4$J=1.6 Hz, Pyr. H-2), 9.95 (s, 1H, OH). IR cm$^{-1}$: ν$_{max}$ 3634, 3021, 1594, 1509, 1489, 793. MS m/z 222 (MH$^+$).

3-(6-Bromo-2-naphthyl)pyridine (4). Purification: CC($CH_2Cl_2$/MeOH, 98:2) yield 21%. $^1$H NMR (500 MHz, CDCl$_3$): δ 7.53 (m, 1H, Pyr. H-5), 7.62 (dd, 1H, $^3$J=8.5 Hz, $^4$J=1.6 Hz, Ar H), 7.73 (dd, 1H, $^3$J=8.5 Hz, $^4$J=1.6 Hz, Ar H), 7.79 (d, 1H, $^3$J=8.5 Hz, Ar H), 7.89 (d, 1H, $^3$J=8.5 Hz, Ar H), 8.02 (d, 1H, $^4$J=1.5 Hz, Ar H), 8.06 (d, 1H, $^4$J=1.5 Hz, Ar H), 8.11 (dt, 1H, $^3$J=7.9 Hz, $^4$J=1.6 Hz, Pyr. H-4), 8.65 (dd, 1H, $^3$J=5.0 Hz, $^4$J=1.6 Hz, Pyr. H-6), 8.99 (d, 1H, $^4$J=1.6 Hz, Pyr. H-2). IR cm$^{-1}$: ν$_{max}$3032, 2963, 1482. MS m/z 286 (M+2H$^+$) 284 (MH$^+$).

3-(6-Ethoxy-2-naphthyl)pyridine (5). Purification: CC($CH_2Cl_2$/MeOH, 98:2) yield 4%. $^1$H NMR (500 MHz, CDCl$_3$): δ 1.51 (t, 3H, $^3$J=6.9 Hz, CH$_3$), 4.18 (q, 2H, $^3$J=6.9 Hz, CH$_2$), 7.17 (d, 1H, $^4$J=2.5 Hz, Ar H), 7.21 (dd, 1H, $^3$J=8.8 Hz, $^4$J=2.5 Hz, Ar H), 7.55 (m, 1H, Pyr. H-5), 7.66 (dd, 1H, $^3$J=8.5 HZ, $^4$J=1.9 Hz, Ar H), 7.82 (d, 1H, $^3$J=8.8 Hz, Ar H), 7.85 (d, 1H, $^3$J=8.8 Hz, Ar H), 7.98 (d, 1H, $^4$J=1.9 Hz, Ar H), 8.16 (dt, 1H, $^3$J=7.9 Hz, $^4$J=1.6 Hz, Pyr. 11-4), 8.61 (dd, 1H, $^3$J=5.0 Hz, $^4$J=1.6 Hz, Pyr. H-6), 8.99 (d, 1H, $^4$J=2.5 Hz, Pyr. H-2). IR cm$^{-1}$: ν$_{max}$ 3021, 2995, 1601, 1489, 1252, 821. MS m/z 250 (MHz), 221, 3-(6-Propoxy-2-naphthyl)pyridine (6). Purification: CC($CH_2Cl_2$/MeOH, 98:2) yield 84%. $^1$H NMR (500 MHz, CDCl$_3$): δ 1.10 (t, 3H, $^3$J=7.2 Hz, CH$_3$), 1.89 (q, 2H, $^3$J=6.6 Hz, CH$_2$), 4.07 (t, 2H, $^3$J=6.6 Hz, CH$_2$), 7.17 (d, 1H, $^4$J=2.5 Hz, Ar H), 7.21 (dd, 1H, $^3$J=8.8 Hz, $^4$J=2.5 Hz, Ar H), 7.39 (m, 1H, Pyr. H-5), 7.67 (dd, 1H, $^3$J=8.5 Hz, $^4$J=1.9 Hz, Ar H), 7.82 (d, 1H, $^3$J=8.5 Hz, Ar H), 7.83 (d, 1H, $^3$J=8.8 Hz, Ar H), 7.97 (d, 1H, $^4$J=1.9 Hz, Ar H), 7.98 (dt, 1H, $^3$J=7.9 Hz, $^4$J=1.6 Hz, Pyr. H-4), 8.60 (dd, 1H, $^3$J=4.7 Hz, $^4$J=1.6 Hz, Pyr. H-6), 8.96 (d, 1H, $^4$J=2.5 Hz, Pyr. H-2). IR cm$^{-1}$. ν$_{max}$ 2967, 2934, 2878, 1629, 1604, 1491, 1389, 1254. MS m/z 264 (MH$^+$).

3-(6-Benzyloxy-2-naphthyl)pyridine (7). Purification: CC($CH_2Cl_2$/MeOH, 97:3) yield 76%. $^1$H NMR (500 MHz, CDCl$_3$): δ 5.22 (s, 2H, CH$_2$), 7.26 (d, 1H, $^4$J=2.5 Hz, Ar H), 7.30 (dd, 1H, $^3$J=8. Hz, $^4$J=2.5 Hz, Ar H), 7.36 (t, 1H, $^3$J=7.2 Hz, Ar H), 7.42 (t, 2H, $^3$J=7.6 Hz, Ar H), 7.48-7.51 (m, 1H, Pyr. H-5, Ar H), 7.67 (dd, 1H, $^3$J=8.5 Hz, $^4$J=1.9 Hz, Ar H), 7.84 (d, 1H, $^3$J=8.2 Hz, Ar H), 7.85 (d, 1H, $^3$J=8.5 Hz, Ar H), 7.99 (s, 1H, Ar H), 8.10 (dt, 1H, $^3$J=7.8 Hz, $^4$J=1.6 Hz, Pyr. H-4), 8.62 (dd, 1H, $^3$J=5.0 Hz, $^4$J=1.3 Hz, Pyr. H-6), 8.98 (d, 1H, $^4$J=2.2 Hz, Pyr. H-2). IR cm$^{-1}$: ν$_{max}$ 3040, 1604, 1490. MS m/z 312 (MH$^+$), 221.

6-Pyridin-3-yl-2-naphthonitrile (8). Duration of reaction only 2.5 h. Purification: CC($CH_2Cl_2$/MeOH, 98:2) yield 71%. $^1$H NMR (500 MHz, CDCl$_3$): δ 7.55 (m, 1H, Pyr. H-5), 7.68 (dd, 1H, $^3$J=8.5 Hz, $^4$J=1.5 Hz, Ar H), 7.84 (dd, 1H, $^3$J=8.5 Hz, $^4$J=1.8 Hz, Ar H), 8.01 (d, 1H, $^3$J=8.5 Hz, Ar H), 8.04 (d, 1H, $^3$J=8.5 Hz, Ar H), 8.10 (d, 1H, $^4$J=1.2 Hz, Ar H), 8.12 (dt, 1H, $^3$J=7.9 Hz, $^4$J=1.5 Hz, Pyr. H-4), 8.28 (s, 1H, Ar H), 8.70 (dd, 1H, $^3$J=4.9 Hz, $^4$J=1.5 Hz, Pyr, H-6), 9.01 (d, 1H, $^4$J=2.4 Hz, Pyr. H-2). IR cm$^{-1}$: ν$_{max}$ 3032, 2224 (CN), 1629, 1469, 1424. MS m/z 231 (MH$^+$).

3-(5-Chloro-6-methoxy-2-naphthyl)pyridine (9). Purification: CC($CH_2Cl_2$/MeOH, 97:3) yield 93%. $^1$H NMR (500 MHz, CDCl$_3$): δ 4.07 (s, 3H, OCH$_3$), 7.39 (d, 1H, $^3$J=9.1 Hz, Ar H), 7.64 (m, 1H, Pyr. H-5), 7.79 (dd, 1H, $^3$J=9.1 Hz, $^4$J=2.2 Hz, Ar H), 7.89 (d, 1H, $^3$J=8.8 Hz, Ar H), 8.04 (d, 1H, $^4$J=1.9 Hz, Ar H), 8.26 (dt, 1H, $^3$J=8.1 Hz, $^4$J=1.6 Hz, Pyr. H-4), 8.36 (d, 1H, $^3$J=8.8 Hz, Ar H), 8.65 (dd, 1H, $^3$J=5.0 Hz, $^4$J=1.6 Hz, Pyr. H-6), 9.02 (d, 1H, $^4J$=2.2 Hz, Pyr. H-2). IR cm$^{-1}$: ν$_{max}$ 3033, 2955, 2844, 1602, 1490, 1275. MS m/z 272 (M+2H$^+$), 270 (MH$^+$), 255, 227, 192.

3-(5-Bromo-6-methoxy-2-naphthyl)pyridine (10). Purification: CC(CH$_2$Cl$_2$/MeOH, 97:3) yield 66%. $^1$H NMR (500 MHz, CDCl$_3$); δ 4.07 (s, 3H, OCH$_3$), 7.36 (d, 1H, $^3J$=8.8 Hz, Ar H), 7.61 (m, 1H, Pyr. H-5), 7.79 (dd, 1H, $^3J$=9.1 Hz, $^4J$=2.2 Hz, Ar H), 7.92 (d, 1H, $^3J$=8.8 Hz, Ar H), 8.02 (d, 1H, $^4J$=1.9 Hz, Ar H), 8.22 (dt, 1H, $^3J$=7.9 Hz, $^4J$=2.2 Hz, Pyr. H-4), 8.36 (d, 1H, $^3J$=8.8 Hz, Ar H), 8.65 (dd, 1H, $^3J$=5.0 Hz, $^4J$=1.6 Hz, Pyr. H-6), 9.01 (d, 1H, $^4J$=2.2 Hz, Pyr. H-2). IR cm$^{-1}$: ν$_{max}$ 3045, 2955, 2832, 1601, 1488, 1272. MS m/z 317, 316, 315, 314, 270, 227, 191, 163.

3,3'-(2-Methoxynaphthalene-1,6-diyl)dipyridine (11). Purification: CC(CH$_2$Cl$_2$/MeOH, 97:3) yield 5%. $^1$H NMR (500 MHz, CDCl$_3$): δ 3.89 (s, 3H, OCH$_3$), 7.43-7.46 (m, 2H, Ar H, Pyr. H-5), 7.54-7.56 (m, 2H, Ar H, Pyr. H-5), 7.62 (dd, 1H, $^3J$=8.8 Hz, $^4J$=1.9 Hz, Ar H), 7.86 (dt, 1H, $^3J$=7.9 Hz, $^4J$=1.9 Hz, Pyr. H-4), 8.01-8.04 (m, 2H, Ar H, Pyr.H-4), 8.07 (d, 1H, $^4J$=1.6 Hz, Ar H), 8.62 (d, 1H, $^3J$=5.0 Hz, Pyr. H-6), 8.68 (s, 1H, Pyr. H-2), 8.70 (d, 1H, $^3J$=5.0 Hz, Pyr. H-6), 8.97 (s, 1H, Pyr. H-2). IR cm$^{-1}$: ν$_{max}$ 3031, 2950, 2842, 1599, 1488, 1258. MS m/z 313 (MH$^+$), 3-(1,5-Dichloro-6-methoxy-2-naphthyl)pyridine (12). Purification, CC(CH$_2$Cl$_2$, MeOH, 98:2) yield 41%. $^1$H NMR (500 MHz, CDCl$_3$): δ 4.10 (s, 3H, OCH$_3$), 7.48 (d, 1H, $^3J$=9.1 Hz, Ar H), 7.50 (d, 1H, $^3J$=8.8 Hz, Ar H), 7.70 (m, 1H, Pyr. H-5), 8.18 (dt, 1H, $^3J$=7.9 Hz, $^4J$=1.6 Hz, Pyr. H-4), 8.30 (d, 1H, $^3J$=8.8 Hz, Ar H), 8.37 (d, 1H, $^3J$=9.1 Hz, Ar H), 8.73 (dd, 1H, $^3J$=5.3 Hz, $^4J$=1.6 Hz, Pyr. H-6), 8.85 (d, 1H, $^4J$=1.6 Hz, Pyr. H-2). IR cm$^{-1}$: ν$_{max}$ 3060, 2940, 2830, 1617, 1487. MS m/z 307, 306, 305, 304, 270, 227, 191, 163.

3-(7-Methoxy-2-naphthyl)pyridine (13). Reaction time: 8 h. Purification; CC (CH$_2$Cl$_2$/MeOH, 97:3) yield 310%. $^1$H NMR (500 MHz, CDCl$_3$): δ 3.95 (s, 3H, OCH$_3$), 7.18-7.21 (m, 2H, Ar H), 7.48 (m, 1H, Pyr. H-5), 7.54 (dd, 1H, $^3J$=8.2 Hz, $^4J$=1.6 Hz, Ar H), 7.78 (d, 1H, $^3J$=8.5 Hz, Ar H), 7.88 (d, 1H, $^3J$=8.2 Hz, Ar H), 7.95 (d, 1H, $^4J$=1.8 Hz, Ar H), 8.08 (dt, 1H, $^3J$=7.8 Hz, $^4J$=1.6 Hz, Pyr. H-4), 8.63 (dd, 1H, $^3J$=5.0 Hz, $^4J$=1.6 Hz, Pyr. H-6), 8.99 (d, 1H, $^4J$=2.5 Hz, Pyr. H-2). IR cm$^{-1}$: ν$_{max}$ 3030, 2973, 2835, 1626. MS m/z 236 (MH$^+$), 221.

3-(1-Chloro-7-methoxy-2-naphthyl)pyridine (14). Purification: CC (Hexane/EtOAc, 8:2) yield 18%. $^1$H NMR (500 MHz, CDCl$_3$): δ 4.00 (s, 3H, OCH$_3$), 7.26-7.29 (m, 2H, Ar H), 7.59 (m, 1H, Pyr. H-5), 7.64 (d, 1H, $^4J$=2.5 Hz, Ar H), 7.80 (d, 1H, $^3J$=8.8 Hz, Ar H), 7.82 (d, 1H, $^3J$=8.8 Hz, Ar H), 8.06 (dt, 1H, $^3J$=7.9 Hz, $^4J$=1.6 Hz, Pyr. H-4), 8.70 (d, 1H, $^3J$=5.0 Hz, Pyr. H-6), 8.82 (s, 1H, Pyr. H-2). IR cm$^{-1}$. ν$_{max}$ 3020, 2932, 2878, 1677, 1506, 1225. MS m/z 272 (M+2H$^+$), 270 (MH$^+$), 255, 191.

3-(3-Methoxy-2-naphthyl)pyridine (15). Purification: CC(CH$_2$Cl$_2$/MeOH, 98:2) yield 31%. $^1$H NMR (500 MHz, CDCl$_3$): δ 3.94 (s, 3H, OCH$_3$), 7.25 (s, 1H, Ar H), 7.35-7.40 (m, 2H, Ar H, Pyr. H-5), 7.48 (td, 1H, $^3J$=8.2 Hz, $^4J$=1.3 Hz, Ar H), 7.77 (s, 1H, Ar H), 7.78 (d, 1H, $^3J$=8.2 Hz, Ar H), 7.81 (d, 1H, $^3J$=8.2 Hz, Ar H), 7.93 (dt, 1H, $^3J$=7.9 Hz, $^4J$=1.9 Hz, Pyr. H-4), 8.60 (dd, 1H, $^3J$=4.9 Hz, $^4J$=1.8 Hz, Pyr. H-6), 8.85 (s, 1H, Pyr. H-2). IR cm$^{-1}$: ν$_{max}$ 3054, 2962, 2832, 1631, 1599, 1504, 1466, 1410, 1254. MS m/z 236 (MH$^+$).

Methyl-6-pyridin-3-yl-2-naphthoate (16). Purification: CC(CH$_2$Cl$_2$/MeOH, 98:2) yield 100%. $^1$H NMR (500 MHz, CDCl$_3$): δ 3.93 (s, 3H, OCH$_3$), 7.35-7.37 (m, 1H, Pyr. H-5), 7.71 (dd, 1H, $^3J$=8.5 Hz, $^4J$=1.9 Hz, Ar H), 7.89 (d, 1H, $^3J$=8.5 Hz, Ar H), 7.94 (dt, 1H, $^3J$=7.9 Hz, $^4J$=1.6 Hz, Pyr. H-4), 8.00 (d, 1H, $^3J$=8.5 Hz, Ar H), 8.01 (d, 1H, $^3J$=8.5 Hz, Ar H), 8.05 (dd, 1H, $^3J$=8.5 Hz, $^4J$=1.6 Hz, Ar H), 8.58 (dd, 1H, $^3J$=5.0 Hz, $^4J$=1.6 Hz, Pyr. H-6), 8.92 (d, 1H, $^4J$=2.2 Hz, Pyr. H-2). IR cm$^{-1}$: ν$_{max}$. 3052, 2952, 1718 (CO), 1598, 1499, 1292. MS m/z 264 (MH$^+$).

6-Pyridin-3-yl-2-naphthamide (17). Purification: CC (hexane/ethyl acetate, 84:15) yield 61%. $^1$H NMR (500 MHz, CDCl$_3$): δ 7.42-7.45 (m, 1H, Pyr. H-5), 7.75 (dd, 1H, $^3J$=8.5 Hz, $^4J$=1.9 Hz, Ar H), 7.90 (dd, 1H, $^3J$=8.5 Hz, $^4J$=1.9 Hz, Ar H), 7.96 (d, 1H, $^3J$=8.8 Hz, Ar H), 8.01-8.04 (m, 2H, Ar H, Pyr. H-4), 8.06 (d, 1H, $^4J$=1.3 Hz, Ar H), 8.38 (d, 1H, $^4J$=1.3 Hz, Ar H), 8.59 (dd, 1H, $^3J$=4.7 Hz, $^4J$=1.6 Hz, Pyr. H-6), 8.92 (d, 1H, $^4J$=1.9 Hz, Pyr. H-2). IR cm$^{-1}$: ν$_{max}$. MS m/z 249 (MH$^+$).

N-Methyl-6-pyridin-3-yl-2-naphthamides (18). N-Methylformamide was used. Purification: CC(CH$_2$Cl$_2$/MeOH, 95:5) yield 83%. $^1$H NMR (500 MHz, CDCl$_3$): δ 3.10 (s, 3H, OCH$_3$), 6.33 (s, 1H, NH), 7.42-7.44 (m, 1H, Pyr. H-5), 7.77 (dd, 1H, $^3J$=8.5 Hz, $^4J$=1.8 Hz, Ar H), 7.87 (dd, 1H, $^3J$=8.5 Hz, $^4J$=1.5 Hz, Ar H), 7.96-8.07 (m, 4H, 3×Ar H, Pyr. H-4), 8.33 (s, 1H, Ar H), 8.65 (dd, 1H, $^3J$=4.6 Hz, $^4J$=1.5 Hz, Pyr. H-6), 8.98 (d, 1H, $^4J$=1.5 Hz, Pyr. H-2). IR cm$^{-1}$: ν$_{max}$ 3316, 3059, 2929, 1644, 1549, 1313. MS m/z 263 (MH$^+$).

3-Pyridin-3-ylquinoline (19). Purification: CC(CH$_2$Cl$_2$/MeOH, 97:3) yield 30%. $^1$H NMR (500 MHz, CDCl$_3$): δ 7.46 (m, 1H, Pyr. H-5), 7.62 (td, 1H, $^3J$=8.2 Hz, $^4J$=1.3 Hz, Ar H), 7.77 (td, 1H, $^3J$=8.5 Hz, $^4J$=1.6 Hz, Ar H), 7.91 (d, 1H, $^3J$=7.6 Hz, Ar H), 8.02 (dt, 1H, $^3J$=7.9 Hz, $^4J$=2.2 Hz, Pyr. H-4), 8.16 (d, 1H, $^3J$=8.2 Hz, Ar H), 8.33 (d, 1H, $^4J$=2.2 Hz, Ar H), 8.69 (dd, 1H, $^3J$=4.7 Hz, $^4J$=1.3 Hz, Pyr. H-6), 8.98 (d, 1H, $^4J$=2.5 Hz, Pyr. H-2), 9.16 (d, 1H, $^4J$=2.2 Hz, Ar H). IR cm$^{-1}$: ν$_{max}$. 3055, 2930, 1494. MS m/z 207 (MH$^+$).

2-Pyridin-3-ylquinoline (20). Purification: CC(CH$_2$Cl$_2$/MeOH, 99:1). The product was taken up in 4 ml of diethyl ether and admixed with one equivalent of HCl in diethyl ether (1 M). The precipitate was filtered off and thoroughly washed with diethyl ether. Yield 43%. $^1$H NMR (500 MHz, CDCl$_3$): δ 7.68 (td, 1H, $^3J$=7.9 Hz, $^4J$=0.9 Hz, Ar H), 7.86 (td, 1H, $^3J$=8.5 Hz, $^4J$=1.6 Hz, Ar H), 7.95 (dd, 1H, $^3J$=8.2 Hz, $^4J$=0.9 Hz, Ar H), 8.12 (m, 1H, Pyr. H-5), 8.17 (d, 1H, $^3J$=8.5 Hz, Ar H), 8.34 (d, 1H, $^3J$=8.5 Hz, Ar H), 8.57 (d, 1H, $^3J$=8.5 Hz, Ar H), 8.87 (d, 1H, $^3J$=5.4 Hz, Pyr. H-4), 9.34 (d, 1H, $^3J$=8.2 Hz, Pyr. H-6), 9.67 (s, 1H, Pyr. H-2). IR cm$^{-1}$: ν$_{max}$ 3053, 2931, 1596, 1548, 1506. MS m/z 207 (MH$^+$).

2-Pyridin-3-ylquinoxaline (21). Purification: CC(CH$_2$Cl$_1$/MeOH, 99:1). The product was taken up in 4 ml of diethyl ether and admixed with one equivalent of HCl in diethyl ether (1 M). The precipitate was filtered off and thoroughly washed with diethyl ether, Yield 44%. $^1$H NMR (500 MHz, CDCl$_3$): δ 7.79-7.82 (m, 2H, Ar H), 8.07-8.12 (m, 2H, Ar H), 8.14-8.17 (m, 1H, Pyr. H-5), 8.92 (d, 1H, $^3J$=5.0 Hz, Pyr. H-4), 9.33 (d, 1H, $^3J$=7.9 Hz, Pyr. H-6), 9.46 (s, 1H, Pyr. H-2), 9.71 (s, 1H, Ar H). IR cm$^{-1}$: ν$_{max}$ 3066, 1604, 1547, 1499, 1313. MS m/z 208 (MH$^+$), 181, 102, 75, 51.

3-(9-Phenanthryl)pyridine (22). Purification: CC(CH$_2$Cl$_2$/MeOH, 98:2) yield 94%. $^1$H NMR (500 MHz, CDCl$_3$): δ 7.56-7.61 (m, 2H, Ar H, Pyr. H-5), 7.66 (td, 1H, $^3J$=8.2 Hz, $^4J$=1.3 Hz, Ar H), 7.70-7.74 (m, 3H, Ar H), 7.77 (dd, 1H, $^3J$=8.2 Hz, $^4J$=0.9 Hz, Ar H), 7.92 (dd, 1H, $^3J$=7.9 Hz, $^4J$=1.6 Hz, Ar H), 8.03 (dt, 1H, $^3J$=7.9 Hz, $^4J$=1.9 Hz, Pyr. H-4), 8.73-8.76 (m, 2H, Ar H, Pyr. H-6), 8.81 (d, 1H, $^3J$=8.5 Hz, Ar H), 8.85 (d, 1H, $^4J$=2.2 Hz, Pyr. H-2). IR cm$^{-1}$; ν$_{max}$ 3055, 1659, 1535, 1456, 1247. MS m/z 256 (MH$^+$).

1-(2-Naphthyl)-1H-imidazole (23). Purification; CC(CH$_2$Cl$_2$/MeOH, 95:5) yield 340%. $^1$H NMR (500 MHz, CDCl$_3$): δ 7.26 (s, 1H, Im. H-4), 7.40 (s, 1H, Im. H-5), 7.51-7.58 (m, 3H, Ar H), 7.82 (d, 1H $^4J$=1.5 Hz, Ar H), 7.88 (t, 2H, $^3J$=7.6 Hz, Ar H), 7.96 (d, 1H, $^3J$=7.6 Hz, Ar H), 8.05 (s, 1H, Im. H-2). IR cm$^{-1}$: $\nu_{max}$ 3116, 3058, 1688, 1602, 1493. MS m/z 195 (MH$^+$), 167, 139, 115, 77, 51.

1-(3-Methoxy-2-naphthyl)-1H-imidazole (24). Purification: CC(CH$_2$Cl$_2$/MeOH, 97:3) yield 13%. $^1$H NMR (500 MHz, CDCl$_3$): δ 3.97 (s, 3H, OCH$_3$), 7.21 (s, 1H, Im. H-4), 7.30 (s, 2H, Ar H, Im. H-5), 7.24 (td, 1H, $^3$J=8.2 Hz, $^4$J=1.3 Hz, Ar H), 7.51 (td, 1H, $^3$J=8.2 Hz, 4J=1.3 Hz, Ar H), 7.74 (s, 1H, Ar H), 7.79 (d, 2H, $^3$J=8.5 Hz, Ar H), 7.87 (s, 1H, Im. H-2). IR cm$^{-1}$: $\nu_{max}$ 3059, 2940, 2839, 1506. MS m/z 225 (MH$^+$).

1-(6-Methoxy-2-naphthyl)-1H-imidazole (25). Purification: CC(CH$_2$Cl$_2$/MeOH, 97:3) yield 13%. $^1$H NMR (500 MHz, CDCl$_3$): δ 3.95 (s, 3H, OCH$_3$), 7.18 (d, 1H, $^4$J=2.5 Hz, Ar H), 7.24 (dd, 1H, $^3$J=8.5 Hz, $^4$J=2.5 Hz, Ar H), 7.28 (s, 1H, Im. H-4), 7.38 (s, 1H, Im. H-5), 7.48 (dd, 1H, $^3$J=8.5 Hz, $^4$J=2.5 Hz, Ar H), 7.76 (s, 1H, Ar H), 7.77 (d, 1H, $^3$J=8.5 Hz, Ar H), 7.85 (d, 1H, $^3$J=8.5 Hz, Ar H), 8.07 (s, 1H, Im. H-2). IR cm$^{-1}$: $\nu_{max}$ 3113, 3003, 2962, 2842, 1607. MS m/z 225 (MH$^+$), 210, 126.

3-(1H-Imidazol-1-yl)quinoline (26). Purification: CC(CH$_2$Cl$_2$/MeOH, 97:3) yield 18%. $^1$H NMR (500 MHz, CDCl$_3$): δ 7.34 (t, 1H, $^4$J=1.3 Hz, Im. H-4), 7.44 (t, 1H, $^4$J=1.5 Hz, Im. H-5), 7.66 (td, 1H, $^3$J=8.2 Hz, $^4$J=1.3 Hz, Ar H), 7.79 (td, 1H, $^3$J=8.2 Hz, $^4$J=1.5 Hz, Ar H), 7.90 (dd, 1H, $^3$J=8.2 Hz, $^4$J=1.6 Hz, Ar H), 8.17 (s, 1H, Im. H-2), 8.18-8.19 (m, 2H, Ar H), 9.04 (d, 1H, $^4$J=1.8 Hz, Ar H). IR cm$^{-1}$: $\nu_{max}$ 3102, 2962, 1608, 1497. MS m/z 196 (MH$^+$), 169, 77, 51.

4(5)-(2-Naphthyl)-1H-imidazole (27). Purification: CC(CH$_2$Cl$_2$) yield 9%. $^1$H NMR (500 MHz, CDCl$_3$): δ 7.38 (s, 1H, Im. H-4), 7.39-7.45 (m, 2H, Ar H), 7.73 (dd, 1H, $^3$J=8.5 Hz, $^4$J=1.9 Hz, Ar H), 7.74-7.81 (m, 4H, Ar H+Im. H-2), 8.13 (s, 1H, Ar H). IR cm$^{-1}$: $\nu_{max}$ 3125, 3044, 2852. MS m/z 195 (MH$^+$), 168, 141.

1-Methyl-5-(2-naphthyl)-1H-imidazole (28). Purification: CC(CH$_2$Cl$_2$/MeOH, 97:3) yield 18%. $^1$H NMR (500 MHz, CDCl$_3$): δ 3.75 (s, 3H, CH$_3$), 7.22 (s, 1H, Im. H-4), 7.49-7.53 (m, 3H, Ar H), 7.68 (s, 1H, Im. H-2), 7.85-7.87 (m, 3H, Ar H), 7.91 (d, 1H, $^3$j=8.5 Hz, Ar H). IR cm$^{-1}$: $\nu_{max}$ 3083, 3053, 2952, 1600, 1490. MS m/z 209 (MH$^+$), 167, 139, 115.

5-(2-Naphthyl)-1,3-oxazole (29). Purification: CC(CH$_2$Cl$_2$MeOH, 97:3). yield 2-8%. $^1$H NMR (500 MHz, CDCl$_3$): δ 7.47 (s, 1H, Im. H-4), 7.49-7.54 (m, 2H, Ar H), 7.73 (dd, 1H, $^3$J=8.5 Hz, $^4$J=1.6 Hz, Ar H), 7.83-7.90 (m, 3H, Ar H), 7.97 (s, 1H, Im. H-2), 8.14 (s, 1H, Ar H). IR cm$^{-1}$: $\nu_{max}$ 3128, 3055, 2952, 1630, 1497. MS m/z 196 (MH$^+$), 167, 139, 115.

5-(6-Methoxy-2-naphthyl)pyrimidine (30). Purification: CC(CH$_2$Cl$_2$/MeOH, 97:3) yield 240%. $^1$H NMR (500 MHz, CDCl$_3$) δ 3.96 (s, 3H, OCH$_3$), 7.19 (d, 1H, $^4$J=2.5 Hz, Ar H), 7.24 (dd, 1H, $^3$J=8.8 Hz, $^4$J=2.5 Hz, Ar H), 7.67 (dd, 1H, $^3$J=8.5 Hz, $^4$J=1.9 Hz, Ar H), 7.84 (d, 1H, $^3$J=8.5 Hz, Ar H), 7.90 (d, 1H, $^4$J=1.9 Hz, Ar H), 8.02 (d, 1H, $^4$J=1.9 Hz, Ar H), 9.15 (s, 2H, Pyr. H-4, Pyr. H-6), 9.26 (s, 1H, Pyr. H-2). IR cm$^{-1}$: $\nu_{max}$ 3034, 2940, 1694, 1626, 1606, 1487, 1210. MS m/z 237 (MH$^+$).

4-(6-Methoxy-2-naphthyl)pyridine (31). Purification: CC(CH$_2$Cl$_2$/MeOH, 97:3) yield 60%. $^1$H NMR (500 MHz, CDCl$_3$): δ 3.97 (s, 3H, OCH$_3$), 7.19 (d, 1H, $^4$J=2.5 Hz, Ar H), 7.25 (dd, 1H, $^3$J=8.8 Hz, $^4$J=2.5 Hz, Ar H), 7.76 (dd, 1H, $^3$J=8.5 Hz, $^4$J=1.9 Hz, Ar H), 7.86 (d, 1H, $^3$J=8.5 Hz, Ar H), 7.90 (d, 1H, $^3$J=8.5 Hz, Ar H), 7.94 (dd, 1H, $^3$J=6.6 Hz, 4-1.6 Hz, Pyr. H-3, Pyr. H-5), 8.15 (d, 1H, $^4$J=1.9 Hz, Ar H), 8.75 (dd, 1H, $^3$J=6.3 Hz, $^4$J=1.3 Hz, Pyr. H-2, Pyr. H-6). IR cm$^{-1}$: $\nu_{max}$ 3040, 2938, 2840, 1699, 1621, 1488, 1210. MS m/z 236 (MH$^+$).

Example 2

Synthesis of indanes and 3,4-dihydronaphthalenes 32 to 46

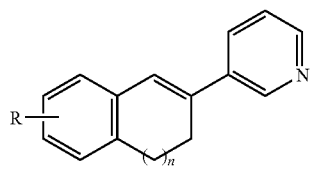
32-37

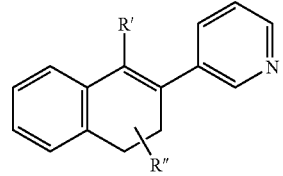
38-42

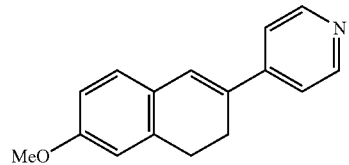 [SMILES: COc1ccc2c(c1)CCC(c1ccncc1)=C2]
43

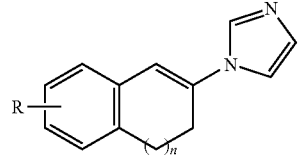
44-48

| No. | n | R |
|-----|---|---|
| 32 | 0 | H |
| 33 | 1 | H |
| 34 | 0 | 6-OMe |
| 35 | 1 | 6-OMe |
| 36 | 0 | 7-OMe |
| 37 | 1 | 7-OMe |

| Nr. | R' | R" |
|-----|----|----|
| 38 | Me | H |

| No. | R' | R" |
|-----|----|----|
| 39 | Et | H |
| 40 | H | 3-Me |
| 41 | H | 4-Me |
| 42 | H | 4-Et |

| Nr. | n | R |
|-----|---|---|
| 44 | 0 | H |
| 45 | 1 | H |
| 46 | 1 | 6-OMe |

A) Synthesis of Compounds 32 to 46:

General synthesis of compounds 32-33, 35, 37, 43: The general procedure for the synthesis of the pyridyl-substituted compounds 32-33, 35, 37, 43 was as represented in the following scheme:

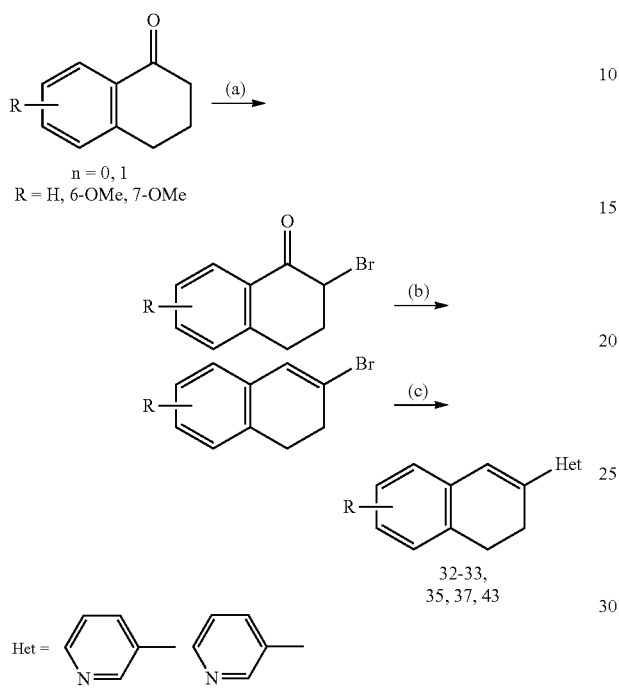

Reaction conditions: (a) TBABr₃, CH₂Cl₂, RT; (b) 1) NaBH₄, MeOH, 0° C. 2) pTSA, toluene, reflux; (c) 3- or 4-pyridylboronic acid, PdP(Ph₃)₄, Na₂CO₃, DME, 80° C.

To a solution of the substituted ketone (1 eq) in dichloromethane/methanol (2.5:1) was added TBABr₃ (1.1 eq) at RT. The mixture was stirred until the orange solution become decolored. The solvent was removed under vacuum, and the precipitate was extracted with diethyl ether. The ether phase was dried over MgSO₄, filtered, and the solvent was removed under vacuum.

A solution of the α-bromoketone (1 eq) in anhydrous methanol/tetrahydrofuran (1:1) was stirred in an ice bath under nitrogen atmosphere. NaBH₄ (0.7 eq) was added in portions. After 15 min of stirring at 0° C. and 30 min of stirring at RT, the mixture was poured into water and extracted with diethyl ether. The organic phase was dried over MgSO₄, filtered, and the solvent was removed under vacuum.

A mixture of the resulting alcohol (1 eq) and p-toluenesulfonic acid (0.1 eq) in toluene was refluxed for 2 h (with a Dean-Stark trap) in order to remove all the water. The mixture was washed with saturated sodium bicarbonate solution and water, the organic phase was dried over MgSO₄, filtered, and the solvent was removed under vacuum.

After purification, a mixture of bromine compound (1 eq), 3- or 4-pyridylboronic acid (1.3 eq), sodium carbonate (2.1 eq) and tetrakis(triphenylphosphine)-palladium (0.02 eq) in ethylene glycol dimethyl ether was maintained at 80° C. over night. After cooling down to RT and adding water, the mixture was extracted with dichloromethane, the organic phase was dried over MgSO₄, filtered, and the solvent was removed under vacuum. The final product was purified by column chromatography and characterized.

General Synthesis of Compounds 34, 36, 40-42:

For the synthesis of the 3-pyridyl-substituted compounds 34, 36, 40-42, the following procedure was adopted:

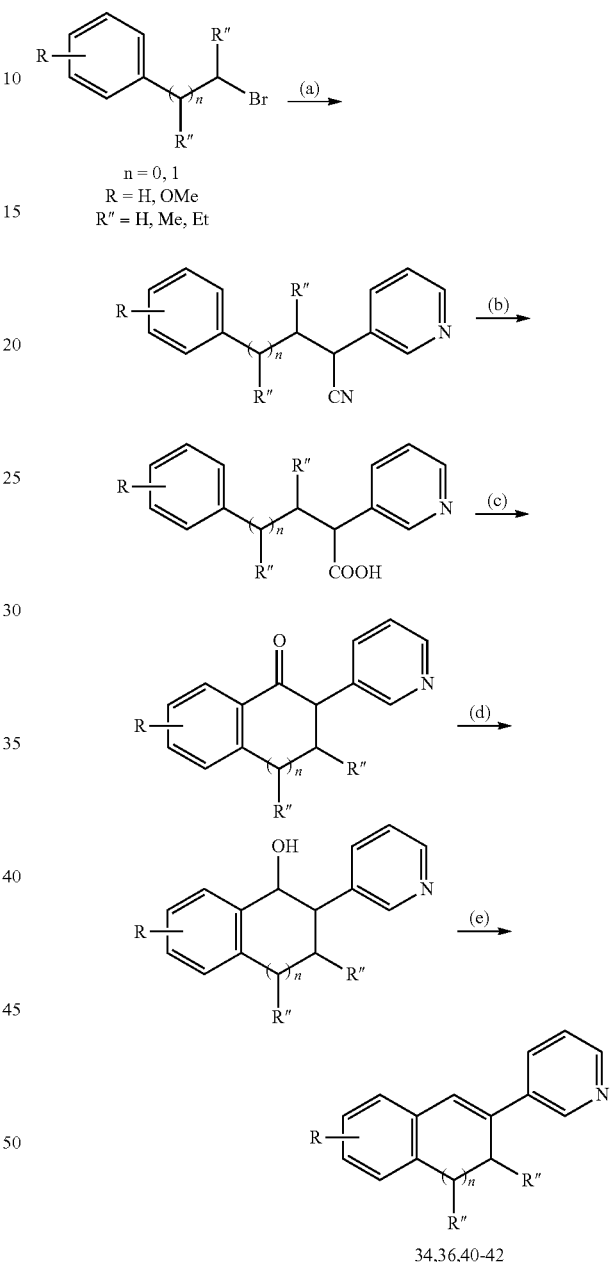

Reaction conditions: (a) 3-Pyridylacetonitrile, NaNH₂, DMF; (b) NaOH, EtOH, reflux; (c) PPA, 110° C.; (d) NaBH₄, MeOH, 0° C.; (e) CH₃COOH/H₂SO₄, 100° C.

This method was described already by Bencze and Barsky for the synthesis of 3 (3,4-dihydronaphthalene-2-yl)pyridine 33 (Bencze, W. L. and Barsky, L. I., J. Med. Pharm. Chem. 5: 1298-1306 (1962)), but not for the novel compounds 34, 36, 40-42.

To a NaNH₂ (1.2 eq) suspension in 20 ml of anhydrous DMF (three-necked flask, reflux condenser, gas inlet and dropping funnel with septum) under a nitrogen atmosphere, 3-pyridylacetonitrile (1.07 eq) was added dropwise with stirring and cooling in an ice bath. After 1 h of stirring at RT and 1 h at 80° C., the mixture was cooled in an ice bath, and the bromine compound (1 eq) was added dropwise. Then, the reaction mixture was stirred at RT for 3 h and at 80° C. for 1 h. After cooling, excess water was added, and the mixture was extracted with diethyl ether. The organic phase was washed with water, dried over MgSO$_4$, filtered, and the solvent was removed under vacuum. The product was purified by column chromatography (elution with CH$_2$Cl$_2$/MeOH (99:1)).

To a solution of the resulting nitrile (1 eq) in a few ml of ethanol, NaOH (11 eq) in water was added. After 24 h of reflux, water was added, and the mixture was adjusted to pH 5 with 2 N HCl and aqueous acetic acid. The mixture was extracted with ethyl acetate, the organic phase was dried over MgSO$_4$, filtered, and the solvent was removed under vacuum. The resulting acid was employed in the next reaction step without further purification.

A mixture of polyphosphoric acid (2.2 g) and the thus prepared acid (0.53 g, 2.05 mmol) was stirred at 110° C. for 20 min. The mixture was poured into ice water and neutralized with 6% NaOH. The solution was adjusted to pH 8 with sodium bicarbonate and extracted with diethyl ether. The organic phase was dried over MgSO$_4$, filtered, and the solvent was removed under vacuum. The product was purified by column chromatography.

A solution of the ketone (1 eq) in anhydrous methanol was stirred in an ice bath under nitrogen atmosphere. NaBH$_4$ (2 eq) was added in portions. After 1 h of stirring at RT, the mixture was poured into water and extracted with dichloromethane. The organic phase was dried over MgSO$_4$, filtered, and the solvent was removed under vacuum. The resulting alcohol was employed in the next reaction step without further purification.

A mixture of 1 ml of acetic acid, 0.14 ml of conc. sulfuric acid and the alcohol (0.30 mmol) was stirred at 100° C. for 1 h. The mixture was poured into ice water and rendered basic with 6% NaOH. After extraction with dichloromethane, the organic phase was dried over MgSO$_4$, filtered, and the solvent was removed under vacuum. The product was purified by column chromatography (elution with CH$_2$Cl$_2$/MeOH (98:2)).

Synthesis of Compounds 38 and 39:

The synthesis of 3-(1-methyl-3,4-dihydronaphthalene-2-yl)pyridine 38 was also described by Bencze and Barsky (Bencze, W. L. and Barsky, L. I., J. Med. Pharm. Chem. 5: 1298-1306 (1962)); 3-(1-ethyl-3,4-dihydronaphthalene-2-yl)pyridine 39 has not been described yet:

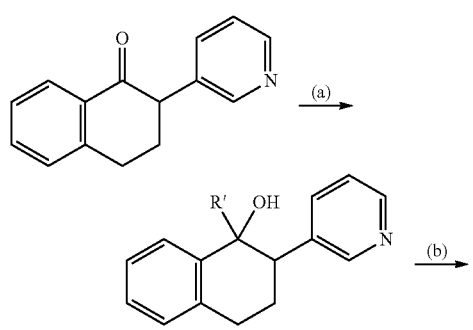

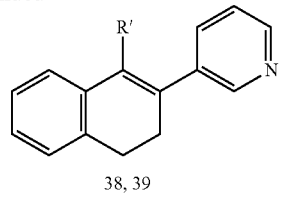

38, 39

38 R' = Me
39 R' = Et

Reaction conditions: (a) R'MgHal, toluene, reflux; (b) HCl, 100° C., 2 h.

General Synthesis of Compounds 44-46:

The procedure for the synthesis of the 1-imidazolyl-substituted compounds 44-46 was as in the following scheme:

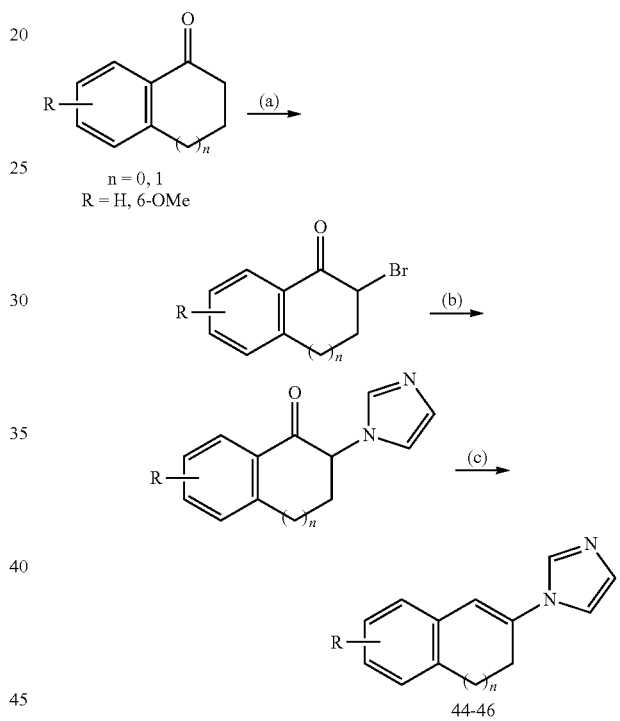

44-46

Reaction conditions: (a) TBABr$_3$, CH$_2$Cl$_2$, RT; (b) imidazole, DMF, RT; (C) 1) NaBH$_4$, MeOH, 0° C.; 2) CH$_3$COOH/H$_2$SO$_4$, 120° C.

This method was already described by Cozzi et al. for the synthesis of 1-(3,4-dihydronaphthalene-2-yl)-1H-imidazole 45 and 1-(6-methoxy-3,4-dihydronaphthalene-2-yl)-1H-imidazole 46 (Cozzi, P. et al., Eur. J. Med. Chem. 26: 423-433 (1991)), but not for compound 44.

To a solution of the substituted ketone (1 eq) in dichlormethane/methanol (2.5:1) was added TBABr$_3$ (1.1 eq) at RT. The mixture was stirred until the orange solution become decolored. The solvent was removed under vacuum, and the precipitate was extracted with diethyl ether. The ether phase was dried over MgSO$_4$, filtered, and the solvent was removed under vacuum.

A solution of the α-bromoketone (1 eq) and imidazole in DMF was stirred at RT over night. The mixture was poured into ice water and extracted with dichloromethane. The organic phase was thoroughly washed with water, dried over MgSO$_4$, filtered, and the solvent was removed under vacuum. The product was purified by column chromatography.

A solution of the 1-imidazolyl-substituted ketone (1 eq) in anhydrous MeOH was stirred in an ice bath under a nitrogen atmosphere, and NaBH$_4$ (2 eq) was added in portions. After 1 h of stirring at RT, the mixture was poured into water and extracted with dichloromethane. The organic phase was dried over MgSO$_4$, filtered, and the solvent was removed under vacuum. The resulting alcohol was employed in the next reaction step without further purification.

The alcohol was dissolved in a mixture of glacial acetic acid and concentrated sulfuric acid and heated at 100° C. for 4 h. After cooling down to RT, the mixture was poured onto ice, neutralized with NaOH and extracted with dichloromethane. The organic phase was dried over MgSO$_{41}$ filtered, and the solvent was removed under vacuum. The final product was purified by column chromatography.

B) Purification Conditions, Yield and Characterization of the Title Compounds:

3-(1H-Inden-2-yl)pyridine (32). Purification: CC(CH$_2$Cl$_2$/MeOH, 99:1) yield 51%. $^1$H NMR (500 MHz, CDCl$_3$): δ=3.81 (s, 2H, H-3), 7.23 (td, 1H, $^3$J=7.2 Hz, 43=0.9 Hz, Ar H), 7.29-7.32 (m, 3H, Ar H, Pyr. H-5), 7.44 (d, 1H, $^3$J=7.2 Hz, Ar H), 7.50 (d, 1H, $^3$J=7.2 Hz, Ar H), 7.89 (dt, 1H, $^3$J=8.1 Hz, 43=1.9 Hz, Pyr. H-4), 8.50 (s, 1H, Pyr. H-6), 8.90 (s, 1H, Pyr. H-2). IR cm$^{-1}$; ν$_{max}$ 3054, 2916, 1533. MS m/z 194 (MH$^+$).

3-(3,4-Dihydronaphthalene-2-yl)pyridine (33). Purification: CC(CH$_2$Cl$_2$/MeOH, 98:2) yield 620%. $^1$H NMR (500 MHz, CDCl$_3$) δ 2.73 (t, 2H, $^3$J=8.3 Hz, H-4), 2.97 (t, 2H, $^3$J=7.8 Hz, H-3), 6.89 (s, 1H, H-1), 7.13-7.19 (m, 4H, Ar H), 7.32-7.34 (m, 1H, Pyr. H-5), 7.85 (td, 1H, $^3$J=8.1 Hz, $^4$J=1.5 Hz, Pyr. H-4), 8.49 (dd, 1H, $^3$J=4.9 Hz, $^4$J=1.5 Hz, Pyr. H-2), 8.79 (d, 1H, $^4$J=1.9 Hz, Pyr. H-6). IR cm$^{-1}$: ν$_{max}$ 3022, 2935, 2885, 2831, 1485, 1421, MS m/z 208 (MH$^+$), 179, 101, 79.

3-(6-Methoxy-1H-inden-2-yl)pyridine (34). Purification: CC(CH$_2$Cl$_2$/MeOH, 98:2) yield 45%. $^1$H NMR (500 MHz, CDCl$_3$) δ 3.77 (s, 2H, H-3), 3.85 (s, 3H, OCH$_3$), 6.86 (dd, 1H, $^3$J=8.2 Hz, $^4$J=2.2 Hz, Ar H), 7.09 (d, 1H, $^4$J=1.5 Hz, Ar H), 7.30 (s, 1H, H-1), 7.34 (d, 1H, $^3$J=8.2 Hz, Ar H), 7.36-7.39 (m, 1H, Pyr. H-5), 7.94 (dt, 1H, $^3$J=7.9 Hz, $^4$J=1.5 Hz, Pyr. H-4), 8.46 (dd, 1H, $^3$J=4.9 Hz, $^4$J=1.5 Hz, Pyr. H-6), 8.85 (d, 1H, $^4$J=1.8 Hz, Pyr. H-2). IR cm$^{-1}$: ν$_{max}$ 3059, 2905, 2836, 1685, 1607, 1493, 1259. MS m/z 224 (MH$^+$).

3-(6-Methoxy-3,4-dihydronaphthalene-2-yl)pyridine (35). Purification: CC (CH$_2$Cl$_2$/MeOH, 98:2) yield 89%. $^1$H NMR (500 MHz, CDCl$_3$). δ 2.73 (t, 2H, $^3$J=8.5 Hz, H-3), 2.96 (t, 2H, $^3$J=8.5 Hz, H-4), 3.82 (s, 3H, OCH$_3$), 6.73-6.75 (m, 2H, Ar H), 6.88 (s, 1H, H-1), 7.10 (d, 1H, $^3$J=8.2 Hz, Ar H), 7.32-7.35 (m, 1H, Pyr. H-5), 7.86 (dt, 1H, $^3$J=8.2 Hz, $^4$J=1.6 Hz, Pyr. H-4), 8.48 (dd, 1H, $^3$J=4.7 Hz, $^4$J=1.6 Hz, Pyr. H-6), 8.79 (d, 1H, $^4$J=2.5 Hz, Pyr. H-2). IR cm$^{-1}$: ν$_{max}$ 3021, 2936, 2834, 1607, 1570, 1499, 1250. MS m/z 238 (MH$^+$), 223, 194.165.

3-(7-Methoxy-1H-inden-2-yl)pyridine (36). Purification: CC(CH$_2$Cl$_2$/MeOH, 99:1) yield 34%, $^1$H NMR (500 MHz, CDCl$_3$): δ 2.73 (t, 2H, $^3$J=8.5 Hz, H-3), 2.96 (t, 2H, $^3$J=8.5 Hz, H-4), 3.82 (s, 3H, OCH$_3$), 6.73-6.75 (m, 2H, Ar H), 6.88 (s, 1H, Ar H), 7.10 (d, 1H, $^3$J=8.2 Hz, Ar H), 7.32-7.35 (m, 1H, Pyr. H-5), 7.86 (dt, 1H, $^3$J=8.2 Hz, $^4$J=1.6 Hz, Pyr. H-4), 8.48 (dd, 1H, $^3$J=4.7 Hz, $^4$J=1.6 Hz, Pyr. H-6), 8.79 (d, 1H, $^4$J=2.5 Hz, Pyr. H-2). IR cm$^{-1}$: ν$_{max}$ 3034, 2938, 2836, 1595, 1483, 1263, 1088. MS m/z 224 (MH$^+$).

3-(7-Methoxy-3,4-dihydronaphthalene-2-yl)pyridine (37). Purification: CC (CH$_2$Cl$_2$/MeOH, 98:2) yield 79%. $^1$H NMR (500 MHz, CDCl$_3$): δ 2.74 (t, 2H, $^3$J=8.2 Hz, H-3), 2.92 (t, 2H, $^3$J=8.2 Hz, H-4), 3.81 (s, 3H, OCH$_3$), 6.73-6.75 (m, 2H, Ar H), 6.87 (s, 1H, H-1), 7.09 (d, 1H, $^3$J=8.2 Hz, Ar H), 7.35-7.38 (m, 1H, Pyr. H-5), 7.88 (dt, 1H, $^3$J=7.8 Hz, $^4$J=1.9 Hz, Pyr. H-4), 8.51 (dd, 1H, $^3$J=5.0 Hz, $^4$J=1.6 Hz, Pyr. H-6), 8.80 (d, 1H, $^4$J=1.6 Hz, Pyr. H-2). IR cm$^{-1}$: ν$_{max}$ 3025, 2934, 2833, 1604, 1571, 1497, 1255, 1040. MS m/z 238 (MH$^+$).

3-(1-Methyl-3,4-dihydronaphthalene-2-yl)pyridine (38). Purification: CC(CH$_2$Cl/MeOH, 97:3) yield 63%. $^1$H NMR (500 MHz, CDCl$_3$): δ 2.05 (s, 3H, CH$_3$), 2.57 (td, 1H, $^3$J=8.2 Hz, $^4$J=1.6 Hz, H-3), 2.92 (t, 1H, $^3$J=8.2 Hz, H-4), 7.19-7.23 (m, 2H, Ar H), 7.27 (t, 1H, $^3$J=7.6 Hz, Ar H), 7.38 (d, 1H, $^3$J=7.6 Hz, Ar H), 7.41-7.45 (m, 1H, Pyr. H-5), 7.72 (td, 1H, $^3$J=7.92 Hz, $^4$J=1.6 Hz, Pyr. H-4), 8.54 (dd, 1H, $^3$J=5.0 Hz, $^4$J=1.6 Hz, Pyr. H-6), 8.57 (s, 1H, Pyr. H-2). IR cm$^{-1}$: ν$_{max}$ 3024, 2937, 2831, 1602, 1487, 1408, 1250. MS m/z 222 (MH$^+$).

3-(1-Ethyl-3,4-dihydronaphthalene-2-yl)pyridine (39). Purification: CC(CH$_2$Cl$_2$/MeOH, 99:1) yield %. $^1$H NMR (500 MHz, CDCl$_3$): δ 1.05 (t, 3H, $^3$J=7.6 Hz, CH$_3$), 2.47-2.54 (m, 4H, CH$_2$, H-3), 2.87 (t, 2H, $^3$J=7.6 Hz, H-4), 7.18-7.20 (m, 2H, Ar H), 7.24-7.27 (m, 1H, Ar H), 7.30-7.33 (m, 1H, Pyr. H-5), 7.38 (d, 1H, $^3$J=7.6 Hz, Ar H), 7.56 (dt, 1H, $^3$J=7.6 Hz, $^4$J=1.8 Hz, Pyr. H-4), 8.51-8.53 (m, 2H, Pyr. H-6, Pyr. H-2). IR cm$^{-1}$: ν$_{max}$. MS m/z (MH$^+$).

3-(3-Methyl-3,4-dihydronaphthalene-2-yl)pyridine (40). Purification: CC(CH$_2$Cl$_2$/MeOH, 98.2) yield 63%. $^1$H NMR (500 MHz, CDCl$_3$) δ 1.03 (d, 3H, $^3$J=6.9 Hz, CH$_3$), 2.76 (dd, 1H, $^2$J=15.4 Hz, $^3$J=2.2 Hz, H-4), 3.00-3.06 (m, 1H, H-3), 3.23 (dd, 1H, $^2$J=15.4 Hz, $^3$J=6.9 Hz, H-4'), 6.86 (s, 1H, H-1), 7.16-7.22 (m, 2H, Ar H), 7.36 (m, 1H, Pyr. H-5), 7.92 (dt, 1H, $^3$J=7.9 Hz, $^4$J=1.6 Hz, Pyr. H-4), 8.52 (dd, 1H, $^3$J=4.7 Hz, $^4$J=1.9 Hz, Pyr. H-6), 8.85 (d, 1H, $^4$J=1.9 Hz, Pyr. H-2). IR cm$^{-1}$: ν$_{max}$ 3020, 2962, 2924, 1564, 1453, 1216. MS m/z 222 (MH$^+$).

3-(4-Methyl-3,4-dihydronaphthalene-2-yl)pyridine (41). Purification: CC(CH$_2$Cl$_2$/MeOH, 99:1) yield 51% $^1$H NMR (500 MHz, CDCl$_3$) δ 1.32 (d, 3H, $^3$J=6.9 Hz, CH$_3$), 2.54 (ddd, 1H, $^2$J=16.1 Hz, $^3$J=7.6 Hz, $^4$J=0.9 Hz, H-3), 2.87 (ddd, 1H, $^2$J=16.1 Hz, $^3$J=6.6 Hz, $^4$J=1.6 Hz, H-3') 3.11-3.17 (m, 1H, H-4), 6.89 (s, 1H, H-1), 7.16-7.24 (m, 4H, Ar H), 7.33-7.35 (m, 1H, Pyr. H-5), 7.86-7.85 (td, 1H, $^3$J=8.1 Hz, $^4$J=1.5 Hz, Pyr. H-4), 8.52 (dd, 1H, $^3$J=4.7H1z, $^4$J=1.6 Hz, Pyr. H-6), 8.82 (d, 1H, $^4$J=2.0 Hz, Pyr. H-2). IR cm$^{-1}$: ν$_{max}$ MS m/z 222 (MH$^+$), 203, 178, 77.

3-(4-Ethyl-3,4-dihydronaphthalene-2-yl)pyridine (42). Purification, yield 55%. $^1$H NMR (CDCl$_3$) δ 0.92 (t, 3H, $^3$J=7.6 Hz, CH$_3$), 1.56-1.69 (m, 2H, CH$_2$), 2.68 (dd, 1H, $^2$J=16.4 Hz, $^3$J=3.8 Hz, H-3), 2.83-2.86 (m, 1H, H-4), 2.93 (dd, 1H, $^2$J=16.4 Hz, $^3$J=2.5 Hz, H-3'), 6.86 (d, 1H, $^4$J=2.5 Hz, H-1), 7.16-7.22 (m, 4H, Ar H), 7.32-7.34 (m, 1H, Pyr. H-5), 7.84 (dt, 1H, $^3$J=7.9 Hz, $^4$J=1.6 Hz, Pyr. H-4), 8.52 (dd, 1H, $^3$J=4.7 Hz, $^4$J=1.6 Hz, Pyr. H-6), 8.82 (d, 1H, $^4$J=1.9 Hz, Pyr H-2). IR cm$^{-1}$: ν$_{max}$ 3035, 2962, 2931, 1682, 1569, 1486, 1456, 1022. MS m/z 236 (MH$^+$).

4-(6-Methoxy-3,4-dihydronaphtaiene-2-yl)pyridine (43). Purification: CC (CH$_2$Cl$_2$/MeOH, 97:3) yield 51%. $^1$H NMR (500 MHz, CDCl$_3$): δ 2.66 (t, 2H, $^3$J=8.5 Hz, H-3), 2.91 (t, 2H, $^3$J=8.5 Hz, H-4), 3.77 (s, 3H, OCH$_3$), 6.69-6.71 (m, 2H, Ar H), 7.09-7.11 (m, 2H, H-1, Ar H), 7.53 (dd, 1H, $^3$J=6.6 Hz, $^4$J=1.6 Hz, Pyr. H-3, Pyr. H-5), 8.49 (dd, 1H, $^3$J=6.6 Hz, $^4$J=1.6 Hz, Pyr. H-2, Pyr. H-6). IR cm$^{-1}$, ν$_{max}$ 3040, 2939, 2835, 1599, 1504, 1209. MS m/z 238 (MH$^+$).

1-(1H-Inden-2-yl)-1H-imidazole (44). Purification: CC(CH$_2$Cl$_2$/MeOH, 97:3) yield 70%. $^1$H NMR (500 MHz, CDCl$_3$): δ 3.87 (s, 2H, H-3), 6.78 (s, 1H, H-1), 7.22-7.24 (m, 2H, Im. H-4, Ar H), 7.30-7.33 (m, 2H, Ar H, Im. H-5), 7.38 (d, 1H, $^3$J=7.6 Hz, Ar H), 7.45 (d, 1H, $^3$J=7.6 Hz, Ar H), 8.09 (s, 1H, Im. H-2). IR cm$^{-1}$: ν$_{max}$ 2940, 1707, 1616, 1498, 1264, 1238. MS m/z 183 (MH$^+$).

1-(3,4-Dihydronaphthalene-2-yl)-1H-imidazole (45). Purification: CC(CH$_2$Cl$_2$/MeOH, 98:2) yield 96%. $^1$H NMR (500 MHz, CDCl$_3$): δ 2.83 (t, 2H, $^3J$=8.2 Hz, H-4), 3.08 (t, 1H, $^3J$=8.2 Hz, H-3), 6.57 (s, 1H, H-1), 7.12 (d, 1H, $^3J$=7.8 Hz, Ar H), 7.18-7.22 (m, 4H, Im. H-4, Ar H), 7.28 (s, 1H, Im. H-5), 7.95 (s, 1H, Im. H-2). IR cm$^{-1}$: ν$_{max}$ 3006, 3990, 1650, 1484, 1295, 1045. MS m/z 197 (MH$^+$).

1-(6-Methoxy-3,4-dihydronaphthalene-2-yl)-1H-imidazole (46). Purification: CC (CH$_2$Cl$_2$/MeOH, 98:2) yield 54%. $^1$H NMR (500 MHz, CDCl$_3$): δ 2.79 (t, 2H, $^3J$=8.2 Hz, H-4), 2.96 (t, 2H, $^3J$=8.2 Hz, H-3), 3.75 (s, 3H, OCH$_3$), 6.76-6.77 (m, 2H, Ar H), 6.82 (s, 1H, H-1), 7.04 (s, 1H, Im. H-4), 7.07 (d, 1H, $^3J$=8.2 Hz, Ar H), 7.64 (s, 1H, Im. H-5), 8.10 (s, 1H, Im. H-2). IR cm$^{-1}$: ν$_{max}$ 2924, 1729, 1646, 1604, 1495, 1459, 1298, 1253. MS m/z 227 (MH$^+$).

Example 3

Enzyme Test Systems for Testing Compounds for Inhibition of CYP Enzymes in vitro The following CYP enzymes were prepared and tested by the methods described: human CYP17 (recombinantly expressed in *E. coli*) (Hutschenreuter, T. U. et al., J. Enzyme Inhib. Med. Chem. 19: 17-32 (2004)) and human placental CYP19 (Hartmann, R. W. & Batzl, C., J. Med. Chem. 29: 1362-1369 (1986)).

A) Isolation of the CYP17-Containing Membrane Fraction from *E. coli* pJL17/OR

The recombinantly altered *E. coli* strain pJL17/OR, in which human CYP17 and rat NADPH-P450-reductase were coexpressed, was grown and stored according to the method of Ehmer et al. (Ehmer, P. B. et al., J. Steroid Biochem. Mol. Biol. 75: 57-63 (2000)). For isolating the membrane fraction, 5 ml of the bacterial cell suspension with an OD$_{578}$ of 50 was washed with phosphate buffer (0.05 M; pH 7.4; 1 mM MgCl$_2$; 0.1 mM EDTA and 0.1 mM DTT). The bacteria were removed by centrifugation and resuspended in 10 ml of ice cold TES buffer (0, 1 M tris-acetate; pH 7.8; 0.5 mM EDTA; 0.5 M sucrose). Four milligrams of lysozyme in 10 ml of ice cold water was added to obtain a final concentration of 0.2 mg/ml. This was followed by incubation for 30 minutes under continued shaking on ice. The spheroblasts were obtained by a renewed centrifugation step at 12,000 g for 10 min and again resuspended in 3 ml of ice cold phosphate buffer (composition see above, additionally 0.5 mM PMSF).

After freezing and thawing, the cells were lysed on ice with an ultrasonic disintegrator. The whole cells and the cell debris were centrifuged off at 3000 g for 7 min. The supernatant was again centrifuged at 50,000 g for 20 min at 4° C. A membrane pellet sedimented and was resuspended in 2 ml of phosphate buffer (composition see above) with 20% glycerol by means of an Ultra-Turrax mixer. The protein concentration was determined by the method of Lowry et al. (Lowry, O. H. et al., J. Biol Chem 193; 265-275 (1951)). Aliquots with an approximate protein concentration of 5 mg/ml were stored at −70° C. until use.

B) Isolation of CYP19 (Aromatase)

The enzyme was obtained from the microsome fraction of fresh human placenta (St. Josephs Krankenhaus, Saarbrucken-Dudweiler, Germany) according to the method of Thompson and Siiteri (Thompson, E. A. & Siiteri, P. K., J. Biol. Chem. 249: 5364-5372 (1974)). The isolated microsomes were suspended in a mini mum volume of phosphate buffer (0.05 M; pH 7.4; 20% glycerol). In addition, DTT (10 mM) and EDTA (1 mM) were added to protect the enzyme from degradation reactions. The protein concentration was determined according to Lowry et al. (Lowry, O. H. et al., J. Biol. Chem. 193: 265-275 (1951)) and should be about 35 mg/ml after the processing.

C) Determination of Percent Inhibition of CYP17

A solution of 6.25 nmol of progesterone (in 5 μl of MeOH) was dissolved in 140 μl of phosphate buffer (0.05 M; pH 7.4; 1 mM MgCl$_2$; 0.1 mM EDTA and 0.1 mM DTT) and preincubated for 5 min at 37° C. together with 50 μl of NADPH-regenerating system (phosphate buffer with 10 mM NADP®, 100 mM glucose-6-phosphate and 2,5 units of glucose-6-phosphate dehydrogenase) and inhibitor (in 5 μl of DMSO). Control incubations were performed in parallel with 5 μl DMSO without inhibitor. The reaction was started by adding 50 μl of a membrane suspension diluted 1 to 5 in phosphate buffer (0.8 to 1 mg of protein per ml). After thoroughly mixing the components, the mixture was incubated at 37° C. for 30 min. The reaction was quenched by adding 50 μl of 1 N HCl.

The steroids were extracted with 1 ml of EtOAc. After a centrifugation step (5 min at 2,500 g), 900 μl of the organic phase was transferred into an Eppendorf vessel with 250 μl of the incubation buffer and 50 μl of 1 N HCl and again shaken. After the centrifugation, 800 μl of the organic phase was removed, placed into a new vessel and evaporated to dryness. The samples were dissolved in 50 μl of a water-methanol mixture (1:1) and analyzed by HPLC. The substrate conversion was calculated from the ratio of the areas of the product peaks (17α-hydroxyprogesterone and 16α-hydroxyprogesterone) to that of the substrate peak. The activity of the inhibitors was calculated from the reduced substrate conversion after the addition of inhibitors in accordance with the following formula:

$$\% \text{ inhibition} = \left[\left[\frac{\Sigma \text{ peak areas (inhibitor incubation)}}{\Sigma \text{ peak areas (control incubation)}}\right] - 1\right] \cdot (-100)$$

D) Determination of the IC$_{50}$ of CYP19

The assay was performed by approximate analogy with the test methods described by Foster et al. and Graves and Salahanick; a detailed description can be found in Hartmann and Batzl 1986 (Foster, A. B. et al., 3 Med Chem 26: 50-54 (1983); Graves, P. E. & Salhanick, H. A., Endocrinology 105: 52-57 (1979); Hartmann, R. W. & Batzl, C., J. Med. Chem. 29: 1362-1369 (1986)). The enzyme activity was monitored by measuring the $^3$H$_2$O formed from [1β-$^3$H]androstenedione during the aromatization. Each reaction vessel contained 15 nM of radioactively labeled [1β-$^3$H]androstenedione (corresponding to 0.08 μCi) and 485 nM of unlabeled androstenedione, 2 mM NADP®, 20 mM glucose-6-phosphate, 0.4 units of glucose-6-phosphate dehydrogenase and inhibitor (0-100 μM) in phosphate buffer (0.05 M; pH 7.4). The compounds to be tested were dissolved in DMSO and diluted with buffer to the desired concentration. The final DMSO concentration of the control and inhibitor incubations was about 2%. Each vessel was preincubated in a water bath at 30° C. for 5 min. The reaction was started by adding the microsomal protein (0.1 mg). The total volume of each mixture was 200 μl. After 14 min, the reaction was quenched by adding 200 μl of ice cold 1 mM HgCl$_2$ solution. Two hundred microliters of a 2% aqueous suspension of dextran-coated charcoal, DCC) was added for absorbing the steroids, and the vessels were shaken for 20 min. Thereafter, the charcoal was centrifuged off at 1500 g for 5 min. The radioactive water present in the supernatant (3H$_2$O) was assayed by scintillation measurement using an LKB-Wallac beta counter. The calculation of the IC$_{50}$ values was effected by a semilogarithmic plot of the percent inhibition against the inhibitor concentration. From this plot, the molar concentration at which 50% inhibition occurred was read.

Example 4

Biological Test Systems for the Testing of Compounds for Selective Inhibition of Human CYP11B1 and CYP11B2 in vitro A) Screening Test in Transgenic Fission Yeast;

A suspension of fission yeast (*S. pombe* PE1) with a cell density of $3 \cdot 10^7$ cells/ml was prepared on a freshly grown culture using fresh EMMG (pH 7.4) as modified according to Ehmer et al. (Ehmer, P. B. et al., 1. Steroid. Biochem. Mol. Biol. 81, 173-179 (2002)). 492.5 µl of this cell suspension was admixed with 5 µl of inhibitor solution (50 µM of the compound to be tested in ethanol or DMSO) and incubated at 32° C. for 15 min. Controls were admixed with 5 µl of ethanol. The enzyme reaction was started by adding 2.5 µl of 11-deoxycorticosterone (20 µM, containing 1.25 nCi of [4-14C]11-deoxycorticosterone in Ethanol), followed by horizontal shaking at 32° C. for 6 h. The test was quenched by extracting the sample with 500 µl of EtOAc. After centrifugation (10,000 g, 2 min), the EtOAc phase was removed and evaporated to dryness. The residue was taken up in 10 µl of chloroform. The reaction of the substrate to form corticosterone was analyzed by HPTLC (see below).

The quantification of the spots for the substrate deoxycorticosterone and the products corticosterone (and, if detectable, 18-hydroxycorticosterone and aldosterone) was effected with the related evaluation program AIDA. For the human aldosterone synthase expressed in *S. pombe*, only corticosterone as a product and the substrate deoxycorticosterone were detected. At an incubation time of 6 hours, 18-hydroxycorticosterone and aldosterone were not formed at any detectable concentrations and therefore were not included in the evaluation. The calculation of the conversion rate was effected according to equation 1.

$$\% P = \frac{[PSL_B] - PSL_{HG}}{[PSL_{DOC} + PSL_B] - 2 \times PSL_{HG}} \times 100 \quad \text{Equation 1}$$

% P conversion rate (percent proportion of the product to the total steroid)

PSL phospho-stimulated luminescence (luminescence value)

$PSL_B$ PSL for corticosterone (B)

$PSL_{DOC}$ PSL for deoxycorticosterone (DOC)

$PSL_{HG}$ PSL of the background

The percent inhibition caused by an inhibitor in the respectively employed concentration was calculated according to equation 2.

$$\% H = \left[1 - \frac{\% P_H}{\% P_K}\right] \times 100 \quad \text{Equation 2}$$

% H percent inhibition

% P percentage of conversion of the substrate to products

% $P_H$ percent conversion in the presence of an inhibitor $P_K$ percent conversion of the control B) Test for Selective CYP11B1 and CYP11B2 Inhibitors:

Maintenance of Cells:

V79 MZh11B1 and V79 MZh11B2, which recombinantly express human aldosterone synthase and steroid-11-β hydroxylase, respectively, and were prepared according to Denner et al. (Denner, K. et al., Pharmacogenetics 5: 89-96 (1995)) were cultured in a $CO_2$ incubator at 37° C. and in a water vapor-saturated atmosphere with 5% $CO_2$ in cell culture dishes of 60 or 90 mm diameter. Both cell lines were cultured in DMEM+ containing 10% FCS and the antibiotics penicillin and streptomycin (1%) for protection from bacterial contamination. The cells were passaged every 2-3 days after treatment with trypsin/EDTA because the doubling rate was 1-2 days depending on the number of cells. The cells were passaged for a maximum of 12-15 times in order to exclude any cell alterations. When there was further need, freshly thawed cells were employed.

| DMEM+ - medium | |
|---|---|
| DMEM powder medium | 13.4 g |
| NaHCO₃ | 3.7 g |
| L-Glutamine (200 mM) | 20.0 ml |
| Penicillin (100 units/ml)/streptomycin (0.1 mg/ml) | 10.0 ml |
| Sodium pyruvate (100 mM) | 10.0 ml |
| Fetal calf serum (FCS) | 100 ml |
| H₂O bidist. | ad 1 l |

The pH of the medium was adjusted to 7.2-7.3. FCS was added only after sterile filtration.

Inhibition test: V79 MZh11B1 and V79 MZh 11B2 cells ($8 \cdot 10^5$ cells per well) were grown to confluency on 24-well cell culture plates with 1.9 cm² culture area per well (Nunc, Roskilde, Denmark). Before the test, the DMEM culture medium present was removed, and 450 µl of fresh DMEM with inhibitor was added for at least three concentrations to each well to determine the $IC_{50}$. After preincubation (60 min, 37° C.), the reaction was started by adding 50 µl of DMEM with 2.5 µl of solution of the substrate 11-deoxycorticosterone (20 µM, containing 1.25 nCi of [4-$^{14}$C]11-deoxycorticosterone in ethanol). Thereafter, the plate was stored at 37° C. and 5% $CO_2$ in a $CO_2$ incubator. The V79 MZh 11B1 cells were incubated for 120 min, and the V79 MZh 11B2 cells were incubated for 40 min. Controls without inhibitor were treated in the same way. The enzyme reactions were quenched by extracting the supernatant with 500 µl of EtOAc. The samples were centrifuged (10,000 g, 2 min), the solvent was removed and evaporated. The residue was taken up in 10 µl of chloroform and analyzed by HPTLC (see below).

The conversion rate for V79 MZh 11B1 was calculated by analogy with equation 1 (Ex. 5A), where:

$PSL_B$ PSL for cortisol or corticosterone $PSL_{DOC}$ PSL for deoxycortisol (RSS) or deoxycorticosterone For V79 MZh11B2, the conversion rate was obtained in accordance with equation 3;

$$\% P = \frac{[PSL_B + PSL_{18OHB} + PSL_{Aldo}] - 3 \times PSL_{HG}}{[PSL_{DOC} + PSL_B + PSL_{18OHB} + PSL_{Aldo}] - 4 \times PSL_{HG}} \times 100 \quad \text{Equation 3}$$

% P conversion rate (proportion of product to the total steroid)

PSL phospho-stimulated luminescence (luminescence value)

$PSL_B$ PSL for corticosterone (B)

$PSL_{18OHB}$ PSL for 18-hydroxycorticosterone (18OHB)

$PSL_{Aldo}$ PSL for aldosterone $PSL_{DOC}$ PSL for 11-deoxycorticosterone (DOC)

$PSL_{HG}$ PSL of the background

The percent inhibition caused by an inhibitor in the respectively employed concentration was calculated according to equation 2 (Ex. 4A).

Determination of the $IC_{50}$: The $IC_{50}$ is defined as that concentration of the inhibitor at which the enzyme is inhibited by 50%. It was calculated by determining the percent inhibition for at least 3 different inhibitor concentrations, which must all be in the linear range of the sigmoidal $IC_{50}$ curve (log C/% inhibition).

The calculation was effected by linear regression. The values determined were used only if they formed a straight line with a reliability of r<0.95.

C) HPTLC Analysis and Phospho-Imaging of the Radioactively Labeled Steroids:

The resuspended residue from Example 4A or 4B which contained the radioactively labeled steroids was applied to an HPTLC plate (20×10 cm, silica gel 60$F_{254}$) with a concentration zone (Merck, Darmstadt, Germany). The plate was developed twice with the mobile solvent chloroform:methanol:water (300:20:1). Unlabeled 11-deoxycorticosterone and corticosterone were applied as a reference for the CYP11B1 reaction. For the CYP11B2 reaction, 11-deoxycorticosterone, corticosterone, 18-hydroxycorticosterone and aldosterone were used as references. The detection of the unlabeled references was effected at 260 nm. Subsequently, imaging plates (BAS MS2340, for $^{14}C$ samples, Raytest, Straubenhardt, Germany) were exposed to the HPTLC plates for 48 h. The imaging plates were scanned with the phosphoimager system Fuji FLA 3000 (Raytest, Straubenhardt, Germany), and the steroids were quantified.

Example 5

Inhibition of Adrenal CYP11B Enzymes in vitro by Heteroaryl-Substituted Naphthalenes Heteroaryl-substituted naphthalenes were tested as inhibitors as described in Examples 3 and 4. The results of the tests are summarized in Table 1.

TABLE 1

Heteroaryl-substituted naphthalenes: inhibition of adrenal CYP11B enzymes, CYP17 and CYP19 in vitro

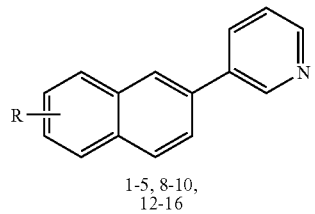

1-5, 8-10, 12-16

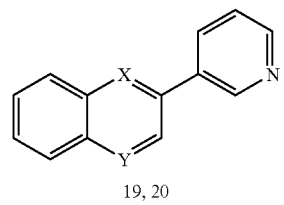

19, 20

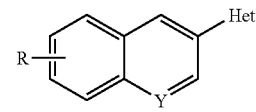

23-24, 27, 29, 30

| Compound | R | Het | % Inhib.[a] Human[b] hCYP11B2 | IC$_{50}$ value (nM)[c] V79 11B1[d] hCYP11B1 | IC$_{50}$ value (nM)[c] V79 11B2[e] hCYP11B2 | % Inhib.[a] [IC$_{50}$ (nM)[g]] Human[f] CYP17 | IC$_{50}$ (nM)[g] [% Inhib.[a]] Human[h] CYP19 |
|---|---|---|---|---|---|---|---|
| 1 | H | | 92 | 2395 | 28 | 40 | 5727 |
| 2 | 6-OMe | | 91 | 574 | 6 | [667] | 586 |
| 3 | 6-OH | | 88 | 715 | 23 | 65 | [61] |
| 4 | 6-Br | | 85 | 899 | 15 | 46 | [33] |
| 5 | 6-OEt | | 86 | 883 | 12 | 53 | 6639 |
| 8 | 6-CN | | 98 | 691 | 3 | [686] | [44] |
| 9 | 5-Cl-6-OMe | | 86 | 569 | 13 | 32 | 1805 |
| 10 | 5-Br-6-OMe | | 68 | 1531 | 33 | 38 | 9107 |
| 12 | 1,5-Cl-6-OMe | | 82 | 1545 | 28 | [233] | 970 |
| 13 | 7-OMe | | 46 | nd | nd | nd | nd |
| 14 | 1-Cl-7-OMe | | 85 | 771 | 29 | [27] | [65] |
| 15 | 3-OMe | | 38 | nd | nd | nd | nd |
| 16 | 6-COOMe | | 66 | 10505 | 73 | 12 | 1252 |
| 19 | X = CH, Y = N | | 40 | nd | nd | nd | nd |
| 20 | X = N, Y = CH | | 53 | nd | nd | nd | nd |

TABLE 1-continued

| | | | | | | | |
|---|---|---|---|---|---|---|---|
| 23 | H | 1-imidazolyl | 80 | 1052 | 38 | 13 | 2821 |
| 24 | 3-OMe | 1-imidazolyl | 86 | 5015 | 40 | 4 | 129 |
| 27 | H | 5-imidazolyl | 41 | 206 | nd | nd | nd |
| 29 | H | 5-oxazolyl | 16 | 805 | nd | nd | nd |
| 30 | 6-OMe | 5-pyrimidyl | 46 | nd | nd | nd | nd |
| Ketoconazole | — | | 36 | 224 | 81 | 40 | nd |
| Fadrozole | — | | 68 | 10 | 1 | 5 | 30 |

[a] Mean value of 4 determinations, standard error <10%.
[b] S. pombe cells which express human CYP11B2; deoxycorticosterone substrate, 100 nM; inhibitor, 500 nM.
[c] Mean value of 4 determinations, standard error <20%.
[d] hamster fibroblasts which express human CYP11B1; deoxycorticosterone substrate, 100 nM.
[e] hamster fibroblasts which express human CYP11B2; deoxycorticosterone substrate, 100 nM.
[f] E. coli which expresses human CYP17; 5 mg/ml protein; progesterone substrate, 2.5 μM; inhibitor, 2.5 μM.
[g] Mean value of 4 determinations, standard error <5%;
[h] human placental CYP19, 1 mg/ml protein; androstenedione substrate, 2.5 μM;
(n.d. = not determined)

Example 6

Inhibition of Adrenal CYP11B Enzymes in vitro by Heteroaryl-Substituted 3,4-dihydronaphthalenes and Indanes Heteroaryl-substituted 3,4-dihydronaphthalenes and indanes were tested as inhibitors as described in Examples 3 and 4. The results of the tests are summarized in Table 2.

TABLE 2

Heteroaryl-substituted 3,4-dihydronaphthalenes and indanes; inhibition of adrenal CYP11B enzymes, CYP17 and CYP19 in vitro

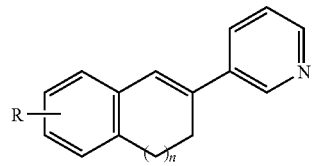

32-35, 37-41, 45-46

| Compound | n | R | % Inhibition[a] Human[b] hCYP11B2 | IC$_{50}$ value (nM)[c] V79 11B1[d] hCY11B1 | IC$_{50}$ value (nM)[c] V79 11B2[e] hCYP11B2 | % Inhib.[a] [IC$_{50}$ (nM)[g]] human[f] CYP17 | IC$_{50}$ (nM)[g] [% Inhib.[a]] Human[h] CYP19 |
|---|---|---|---|---|---|---|---|
| 32 | 0 | H | 90 | 862 | 13.5 | 2 | [47] |
| 33 | 1 | H | 95 | 411 | 7 | 37 | 4.073 |
| 34 | 0 | 6-OMe | 66 | 5684 | 4 | 7 | [50] |
| 35 | 1 | 6-OMe | 97 | 213 | 2 | 62 | 814 |
| 37 | 1 | 7-OMe | 51 | nd | nd | nd | nd |
| 38 | 1 | 1-Me | 94 | 1268 | 7 | [1085] | 6045 |
| 39 | 1 | 1-Et | 81 | 2117 | 30 | 57 | 1507 |
| 40 | 1 | 3-Me | 84 | 503 | 5 | 27 | 1787 |
| 41 | 1 | 4-Me | 82 | 437 | 13 | 23 | 3551 |
| 45 | 1 | H | 34 | 638 | nd | nd | nd |
| 46 | 1 | H | 35 | 763 | nd | nd | nd |
| Ketoconazole | — | | 36 | 224 | 81 | 40 | nd |
| Fadrozole | — | | 68 | 10 | 1 | 5 | 30 |

[a] Mean value of 4 determinations, standard error <10%.
[b] S. pombe cells which express human CYP11B2; deoxycorticosterone substrate, 100 nM; inhibitor, 500 nM.
[c] Mean value of 4 determinations, standard error <20%.
[d] hamster fibroblasts which express human CYP11B1; deoxycorticosterone substrate, 100 nM.
[e] hamster fibroblasts which express human CYP11B2; deoxycorticosterone substrate, 100 nM.
[f] E. coli which expresses human CYP17; 5 mg/ml protein; progesterone substrate, 2.5 μM; inhibitor, 2.5 μM.
[g] Mean value of 4 determinations, standard error <5%;
[h] human placental CYP19, 1 mg/ml protein; androstenedione substrate, 2.5 μM;
(n.d. = not determined)

Example 7

Inhibition of CYP Enzymes in vitro by the Reference Compounds Ketoconazole and Fadrozole Ketocoanzole or fadrozole were tested as inhibitors as described in Examples 3 and 4. The results of the tests are summarized in Table 3.

TABLE 3

Ketoconazole and fadrozole: Inhibition of adrenal CYP11B enzymes, CYP17 and CYP19 in vitro

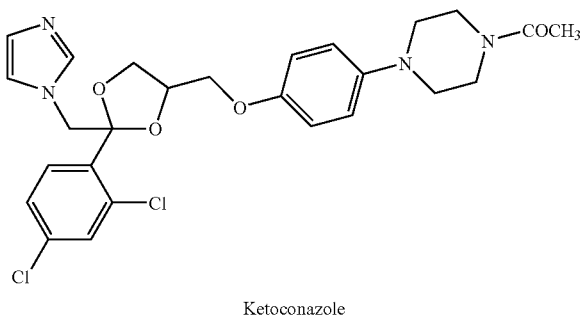 [SMILES: CC(=O)N1CCN(c2ccc(OCC3COC(Cn4ccnc4)(c4ccc(Cl)cc4Cl)O3)cc2)CC1]

Ketoconazole

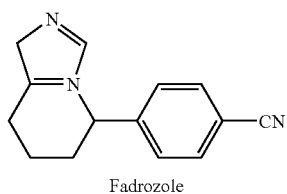

Fadrozole

| Compound | % Inhibition[a] human[b] hCYP11B2 | IC$_{50}$ (nM)[c] V79 11B1[d] hCYP11B1 | IC$_{50}$ (nM)[c] V79 11B2[e] hCYP11B2 | % Inhibition human[f] CYP17 | IC$_{50}$ (nM) human[g] CYP19 |
|---|---|---|---|---|---|
| Ketoconazole | 36 | n.d. | 80.5 | 40 | n.d. |
| Fadrozole | 68 | 9.7 | 1.0 | 7 | 29.5 |

[a]Mean value of 4 determinations, standard error <10%;

[b]S. pombe cells which express human CYP11B2; deoxycorticosterone substrate, 100 nM; inhibitor, 500 nM.

[c]Mean value of 4 determinations, standard error <20%.

[d]Hamster fibroblasts which express human CYP11B1; deoxycorticosterone substrate, 100 nM.

[e]Hamster fibroblasts which express human CYP11B2; deoxycorticosterone substrate, 100 nM.

[f]Mean value of 4 determinations, standard error <10%; E. coli which express human CYP17; 5 mg/ml protein; progesterone substrate, 2.5 μM; inhibitor, 2.5 μM.

[g]Mean value of 4 determinations, standard error <5%; human placental CYP19, 1 mg/ml protein; testosterone substrate, 2.5 μM;

(n.d. = not determined)

Example 8

Test of Selected Compounds with NCI-H295R cells

Of the compounds presented under Examples 5 and 6, some were examined on the NCI-H295R system. For comparison, fadrozole was used as a reference. The exemplary results obtained are not directly comparable with the IC$_{50}$ values and percent inhibition values obtained in V79 cells since other test parameters and a different substrate, inter alia, were used for the inhibitor assays on NCI-H295R (explanation see Table 4).

In comparison with fadrozole, a coarse correlation between the two test systems could be established, wherein compounds 1 and 2 influenced the CYP11B1 to a clearly lower extent.

TABLE 4

Comparison of inhibition data from NCI-H295R, V79 MZ

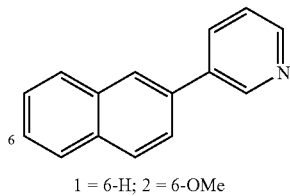 [SMILES: c1cncc(-c2ccc3ccccc3c2)c1]

1 = 6-H; 2 = 6-OMe

| | NCI-H295R | | | | |
|---|---|---|---|---|---|
| Compound | CYP11B1 RSS % inhibition[a] [IC$_{50}$ nM] | CYP11B2 B % inhibition[b] [IC$_{50}$ nM] | CYP11B2 DOC % inhibition[b] [IC$_{50}$ nM] | V79 11B1 CYP11B1 DOC [IC$_{50}$ nM][c] | V79 11B2 CYP11B2 DOC [IC$_{50}$ nM][c] |
| Fadrozole | 89.8 ± 1.5 [28.3 ± 2.8] | 32.2 ± 6.1 [20870 ± 6268] | 89.6 ± 0.2 [18.7 ± 0.8] | [9] | [1] |
| 1 | 43.4 ± 4.7 [3449 ± 273] | 45.6 ± 2.2 [2111 ± 124] | 82.9 ± 0.9 [163.9 ± 21.5] | [2395] | [28.4] |
| 2 | 48.5 ± 2.9 [2950 ± 54.3] | 49.5 ± 2.4 [558.5 ± 118.4] | 81.4 ± 6.6 [100.1 ± 7.6] | [574] | [6.2] |

[a]inhibition of CYP11B1 activity in NCI-H295R, inhibitor concentration 2.5 μM, [$^3$H]-deoxycortisol (RSS, 500 nM); quantification of the products after HPLC separation
[b]inhibition of CYP11B2 activity in NCI-H295R, inhibitor concentration 2.5 μM, [$^3$H]-corticosterone (B, 500 nM) or [$^{14}$C]deoxycorticosterone (DOC, 500 nM); quantification of the products after HPLC separation by means of phosphoimager system
[c]determination of IC$_{50}$ values for CYP11B1 and CYP11B2 in V79 MZh11B1 and V79 MZh11B2; [$^{14}$C]deoxycorticosterone (DOC, 100 nM); quantification of the products after HPLC separation by means of phosphoimager system. For determining IC$_{50}$ values, the compounds were tested in at least 3 different concentrations.
n.t.: not tested,
RSS = deoxycortisol;
B = corticosterone;
DOC = deoxycorticosterone, shown are the mean values (± standard deviations) of at least three independent tests.

For examining the effect of different inhibitors on NCI-H295R, a test method in a 24-well format has been developed. For testing inhibitors, a preincubation for one hour was performed first, followed by starting the enzyme reactions by adding substrate (500 nM), A) Seeding:

The cell lines were grown and passaged until a confluent cell lawn had formed. By tryptic treatment, the cell material of at least two culture dishes was obtained, and the number of cells determined by means of a CASY TT cell counter (150 μl capillary). By diluting the cell suspension with DMEM:Ham's F12, a cell density of 1×10$^6$ cells/ml was adjusted. Of the thus obtained cell suspensions, 1 ml each was placed on a well of a 24-well plate so that each well was coated with 1×10$^6$ cells. With the cell material of two confluently grown culture dishes, two 24-well plates could be coated. After 24 hours, the cells had grown on, and after another 24 hours' stimulation phase with a solution containing potassium ions (final concentration: 20 mM KCl), could be employed for the test.

B) Substrate Solutions:

For testing the influence of the inhibitors on CYP11B1, tritium-labeled deoxycortisol was employed as the substrate ([$^3$H]-RSS). For preparing the substrate stock solution, 60 μl of [$^3$H(G)]-deoxycortisol (3 Ci/mmol, 1 mCi/ml) in ethanol was diluted with 140 μl of ethanol (Hartmann Analytik, Braunschweig, Germany). Of this solution, 2.5 μl was employed per sample, which corresponded to a final concentration of 500 nM in the test for a test volume of 500 μl.

In the substrate solutions for the examinations on CYP11B2, the corticosterone substrate solution (final concentration in the test: 500 nM) consisted of 38.4 μl of [1,2-$^3$H(N)]corticosterone (1 mCi/ml, 76.5 Ci/mmol; NEN-Perkin-Elmer) in ethanol, 39.0 μl of unlabeled corticosterone solution (0.5 mM in ethanol) and 122.6 μl of ethanol. Deoxycorticosterone, which was also employed in a final concentration of 500 nM, was composed of 18 μl of [$^{14}$C]-labeled deoxycorticosterone (60.0 mCi/mmol; 0.5 nCi/μl) in ethanol in admixture with 54 μl of unlabeled substance (0.5 mM in ethanol) and 228 μl of ethanol.

C) Inhibitor Solutions:

The concentrations required for the determination of the IC$_{50}$ values were adjusted by diluting the stock solution (10 mM) at 1:40 with ethanol. Of this solution, 5 μl each was added to the samples.

D) Performance of the Tests:

Preincubation:

The medium present was sucked off and replaced by 450 μl of DMEM:Ham's F12 in which the inhibitor was added in the corresponding concentration (final concentration of the inhibitor in the final volume (500 μl) of the test: 2.5 μM), followed by preincubation for 1 h.

Test Start:

The reaction was initiated by adding 50 μl of DMEM:Ham's 112 containing 2.5 μl of the respective substrate mix (final concentration of the substrate: 0.5 μM).

Then, the 24-well plate was stored in a CO$_2$ incubator at 37° C. and 5% CO$_2$. The incubation time was 3 hours when deoxycorticosterone was used as the substrate, 24 hours for corticosterone, and 48 hours for deoxycortisol.

Test Stop:

After elapse of the incubation times, the plates were briefly swung, and then the content of the wells was removed quantitatively if possible and inactivated by mixing with 1000 μl of dichloromethane in a 2 ml Eppendorf vessel. After 10 minutes of shaking, it was centrifuged for phase separation, and the upper, organic phase was transferred into a 1.5 ml Eppendorf vessel.

After evaporating the solvent over night under a hood, the residue was taken up in 10 μl of chloroform and applied to the center of the concentration zone of an HPTLC plate. The steroids were separated by developing twice with a mobile solvent composed of chloroform, methanol and water in a ratio of 300:20:1. For detecting the steroids on the TLC, the radiation-exposed film was scanned in the phosphoimager FLA 3000 after two days.

In the case of deoxycortisol as the substrate, the separation was effected after reconstitution in 50 μl of methanol to which unlabeled deoxycortisol, cortisol and cortisone had been added as internal standards by HPLC over an RP18 column with the mobile solvent methanol:water 1.1 and a flow rate of 0.25 ml/min, the detection was effected by means of a Berthold Radiomonitor 509.

The conversion for the substrate deoxycortisol after HPLC separation was calculated according to equation 4;

$$\% \ P = \frac{A_{Cortisol} + A_{Cortison}}{[A_{Cortison} + A_{Cortisol} + A_{RSS}]} \times 100 \qquad \text{Equation 4}$$

% P conversion rate (proportion of product to total steroid in %)
A area in [units·sec]
$A_{Cortisol}$ area for cortisol
$A_{Cortison}$ area for cortisone
$A_{RSS}$ area for deoxycortisol (RSS)

For the substrate deoxycorticosterone, the conversion was obtained in accordance with equation 3 (Ex. 4B).

For the substrate corticosterone, equation 5 was valid:

$$\% \ P = \frac{[PSL_{18OHB} + PSL_{Aldo}] - 2 \times PSL_{HG}}{[PSL_B + PSL_{18OHB} + PSL_{Aldo}] - 3 \times PSL_{HG}} \times 100 \qquad \text{Equation 5}$$

% P conversion rate (proportion of product to total steroid in %)
PSL phospho-stimulated luminescence (luminescence value)
$PSL_B$ PSL for corticosterone (5)
$PSL_{18OHS}$ PSL for 18-hydroxycorticosterone (18OHB)
$PSL_{Aldo}$ PSL for aldosterone
$PSL_{HG}$ PSL of the background The percent inhibition caused by an inhibitor in the respectively employed concentration was calculated according to equation 2 (Ex. 4A).

The determination of C50 was effected as described in Example 4B.

Example 9

Quantification of Steroids in the Supernatant of a cell culture of NCI-H295R Cells H295R cells (see Example 8) were subcultured at a cell density of 1×10⁶ cells/ml in a volume of 1 ml each per well in a 24 well plate and incubated for 48 hours. Thereafter, the medium was replaced by 500 μl of Ultroser SF-free DMEM:Ham's F12 in which the inhibitor to be tested in the corresponding concentration and 1% ethanol were contained, Control incubations merely contained ¹% ethanol. After incubation at 37° C. and 5% $CO_2$ for 6 hours, the supernatant was removed and frozen until further analysis. The inhibitor activities were calculated from the difference between the steroid concentrations in the presence or absence of the test substances employed. The aldosterone concentration was determined with an RIA kit (DRG, Marburg, Germany) in accordance with the manufacturer's instructions. For determining the androgens (bHEA and androstendione) and of cortisol, specific ELrSA kits (ibl-Hamburg, Hamburg, Germany) and the Cortisol ELISA Kit of Cayman Chemical (Ann Arbor, USA), respectively, were used in accordance with the manufacturer's instructions, For measuring the total protein content, the cells were washed with PBS, solubilized in a lysis buffer (8 M urea, 4% (w/v) CHAPS) and frozen at −70° C. After three freezing-thawing cycles, the cells had been lysed, and their protein content was determined by means of the method of Bradford. The results of the steroid determinations were expressed in pg/mg of cell proteins for aldosterone and ng/mg of cell proteins for androgens and cortisol.

Figure 1B:
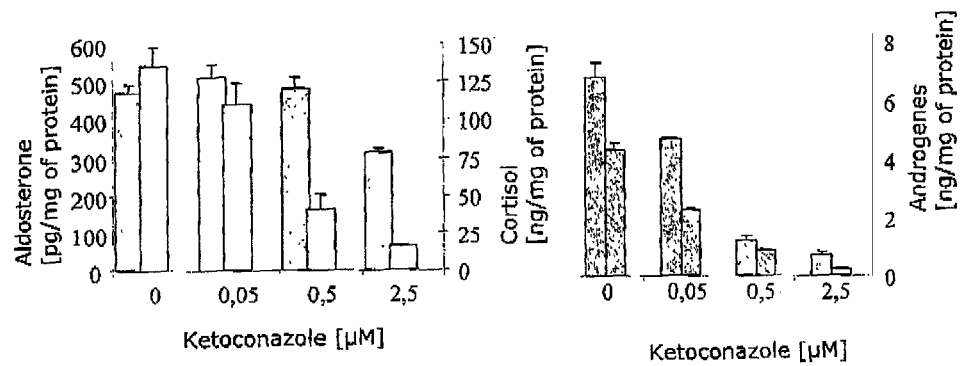
Figure 1C:
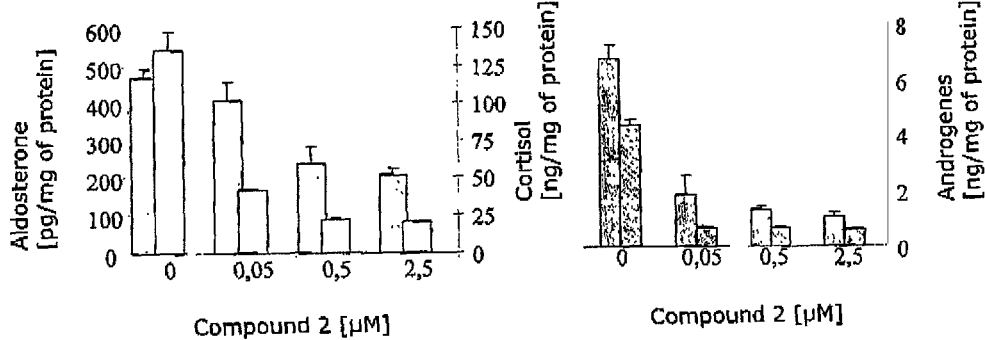

Within 6 hours, a significant concentration-dependent decrease of aldosterone secretion could be established when compound 2 and ketoconazole were employed (FIGS. 1B and 1C) Fadrozole reduced the production of aldosterone with an $IC_{50}$ that was 9 times lower that that of the cortisol production (39.4 nM versus 363.8 nM; FIG. 1A, Table 5), while the productin of adrenal androgens was reduced to a lesser extent ($IC_{50}$>3900 nM for androstendione and 150 nM for DHEA). Ketoconazole showed $IC_{50}$ values of 59.6 nM and 51.8 nM for the inhibition of androstendione and DHEA production. Compound 2 proved to be a potent suppressor of the production of cortisol and adrenal androgens ($IC_{50}$ values <1 nM), while the androsterone production was inhibited only to a low extent (FIG. 1C, Table 5).

TABLE 5

Inhibition of the steroid production in H295R cells, established from the steroid concentration in the supernatant

| Compound | % inhibition of aldosterone production[a] [$IC_{50}$ nM] | % inhibition of cortisol production[a] [$IC_{50}$ nM] | % inhibition of androstendione production[a] [$IC_{50}$ nM] | % inhibition of DHEA production[a] [$IC_{50}$ nM] |
|---|---|---|---|---|
| Fadrozole | 72.9 ± 1.3 [39.4] | 57.8 ± 2.3 [363.8] | 45.0 ± 0.9 [3976] | 66.5 ± 0.9 [150.1] |
| 2 | 56.4 ± 3.5 [962.7] | 78.6 ± 5.4 [<1] | 84.6 ± 2.0 [<1] | 84.5 ± 2.0 [<1] |
| Ketoconazole | 33.3 ± 3.3 [13105] | 88.1 ± 1.0 [154.6] | 89.2 ± 1.2 [59.6] | 94.4 ± 0.6 [51.8] |

[a]Quantification after 6 h of incubation with an inhibitor concentration of 2.5 μM. The supernatant of the cell cultures was used, and the determination was effected by specific immunoassays. Mean values (±SD) from at least three independent experiments.

The invention claimed is:

1. A method of treating hyperaldosteronism, heart failure, myocardial fibrosis, hypercortisolism, diabetes mellitus, depression, age-related cognitive decline or metabolic syndrome in a patient comprising, administering to said patient a therapeutically effective amount of a compound having a structure of formula (Ia)

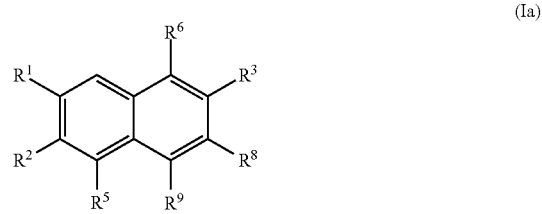

(Ia)

wherein $R^1$ or $R^2$ is hydrogen and the other of substituents $R^1$ or $R^2$ is selected from H and O—$C_{1-6}$ alkyl;
wherein $R^3$ is selected from oxazolyl, pyridyl, imidazolyl and pyrimidyl, which selection can be substituted with one $R^{12}$ residue;

wherein R⁵ and R⁶ are independently selected from H, fluorine, chlorine and bromine;
R⁸ and R⁹ are H; and
R¹² is selected from H, halogen, hydroxy, CN, $C_{1-3}$ alkyl and $C_{1-3}$ alkoxy; or
a pharmaceutically acceptable salt thereof.

2. The method according to claim 1, wherein the compound is chosen from:
3-(6-methoxynaphthalen-2-yl)pyridine;
3-(6-hydroxynaphthalen-2-yl)pyridine;
3-(6-bromonaphthalen-2-yl)pyridine;
3-(6-ethoxynaphthalen-2-yl)pyridine;
3-(6-propoxynaphthalen-2-yl)pyridine;
3-(6-benzyloxynaphthalen-2-yl)pyridine;
3-(6-cyanonaphthalen-2-yl)pyridine;
3-(5-chloro-6-methoxynaphthalen-2-yl)pyridine;
3-(5-bromo-6-methoxynaphthalen-2-yl)pyridine;
3-(7-methoxynaphthalen-2-yl)pyridine; and
3-(1-chloro-7-methoxynaphthalen-2-yl)pyridine.

3. The method according to claim 1, wherein R³ is selected from 3-pyridyl, 4-pyridyl, 1-imidazolyl, 4-imidazolyl, and 5-pyrimidyl.

4. The method according to claim 1, wherein R³ is 3-pyridyl.

5. A method of treating hyperaldosteronism, heart failure, myocardial fibrosis, hypercortisolism, diabetes mellitus, depression, age-related cognitive decline or metabolic syndrome in a patient comprising, administering to said patient a therapeutically effective amount of a compound selected from:
3-(1,5-dichloro-6-methoxynaphthalen-2-yl)pyridine;
3-(3-methoxynaphthalen-2-yl)pyridine;
methyl 6-(pyridin-3-yl)-2-naphthoate;
6-(pyridin-3-yl)-2-naphthamide; and
N-methyl-6-(pyridin-3-yl)-2-naphthamide.

6. A pharmaceutical composition comprising a compound having a structure of formula (Ia)

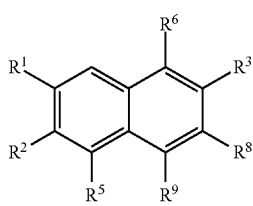

(Ia)

wherein R¹ or R² is hydrogen and the other of substituents R¹ or R² is O—$C_{1-6}$ alkyl;
wherein R³ is selected from oxazolyl, pyridyl, imidazolyl and pyrimidyl, which selection can be substituted with one R¹² residue;
wherein R⁵ and R⁶ are independently selected from H, fluorine, chlorine and bromine;
R⁸ and R⁹ are H; and
R¹² is selected from H, halogen, hydroxy, CN, $C_{1-3}$ alkyl and $C_{1-3}$ alkoxy;
or a pharmaceutically acceptable salt thereof.

7. The composition according to claim 6, wherein R³ is selected from 3-pyridyl, 4-pyridyl, 1-imidazolyl, 4-imidazolyl, and 5-pyrimidyl.

8. The composition according to claim 7, wherein R³ is 3-pyridyl.

9. The composition according to claim 6, wherein the compound is selected from:
3-(6-methoxynaphthalen-2-yl)pyridine;
3-(6-hydroxynaphthalen-2-yl)pyridine;
3-(6-bromonaphthalen-2-yl)pyridine;
3-(6-ethoxynaphthalen-2-yl)pyridine;
3-(6-propoxynaphthalen-2-yl)pyridine;
3-(6-benzyloxynaphthalen-2-yl)pyridine;
3-(5-chloro-6-methoxynaphthalen-2-yl)pyridine;
3-(5-bromo-6-methoxynaphthalen-2-yl)pyridine;
3-(1,5-dichloro-6-methoxynaphthalen-2-yl)pyridine;
3-(7-methoxynaphthalen-2-yl)pyridine; and
3-(1-chloro-7-methoxynaphthalen-2-yl)pyridine.

10. A pharmaceutical composition for treating hyperaldosteronism, heart failure, myocardial fibrosis, hypercortisolism, diabetes mellitus, depression, age-related cognitive decline and metabolic syndrome, comprising one or more compounds having a structure of formula (Ia)

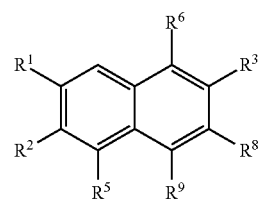

(Ia)

wherein R¹ or R² is hydrogen and the other of substituents R¹ or R² is O—$C_{1-6}$ alkyl;
wherein R³ is selected from oxazolyl, pyridyl, imidazolyl and pyrimidyl, which selection can be substituted with one R¹² residue;
wherein R⁵ and R⁶ are independently selected from H, fluorine, chlorine and bromine;
R⁸ and R⁹ are H; and
R¹² is selected from H, halogen, hydroxy, CN, $C_{1-3}$ alkyl and $C_{1-3}$ alkoxy;
or a pharmaceutically acceptable salt thereof.

11. A composition according to claim 10, wherein R³ is selected from oxazolyl, pyridyl, imidazolyl, and pyrimidyl; wherein R⁵ and R⁶ are each independently selected from H, fluorine, chlorine, or bromine; and wherein R⁴, R⁸, and R⁹ are H.

12. The composition according to claim 11, wherein R³ is selected from 3-pyridyl, 4-pyridyl, 1-imidazolyl, 4-imidazolyl, and 5-pyrimidyl.

13. The composition according to claim 12, wherein R³ is 3-pyridyl.

14. The composition according to claim 10, wherein the compound is selected from:
3-(6-methoxynaphthalen-2-yl)pyridine;
3-(6-bromonaphthalen-2-yl)pyridine;
3-(6-ethoxynaphthalen-2-yl)pyridine;
3-(6-propoxynaphthalen-2-yl)pyridine;
3-(6-benzyloxynaphthalen-2-yl)pyridine;
3-(5-chloro-6-methoxynaphthalen-2-yl)pyridine;
3-(5-bromo-6-methoxynaphthalen-2-yl)pyridine;
3-(1,5-dichloro-6-methoxynaphthalen-2-yl)pyridine;
3-(7-methoxynaphthalen-2-yl)pyridine; and
3-(1-chloro-7-methoxynaphthalen-2-yl)pyridine.

15. The composition according to claim 10, further comprising an additional pharmacologically active compound.

16. A compound having the formula (Ia)

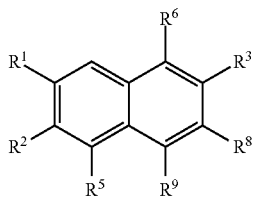

(Ia)

wherein $R^1$ or $R^2$ is hydrogen and the other of substituents $R^1$ or $R^2$ is —O—$C_{1-6}$ alkyl;
wherein $R^3$ is selected from oxazolyl, pyridyl, and imidazolyl, which selection can be substituted with one $R^{12}$ residue;
wherein $R^5$ and $R^6$ are independently selected from H, fluorine, chlorine and bromine;
$R^8$ and $R^9$ are H; and
$R^{12}$ is selected from H, halogen, hydroxy, CN, $C_{1-3}$ alkyl and $C_{1-3}$ alkoxy;
or a pharmaceutically acceptable salt thereof.

17. The compound according to claim 16, wherein $R^3$ is selected from 3-pyridyl, 1-imidazolyl, and 4-imidazolyl.

18. The compound according to claim 17, wherein $R^3$ is 3-pyridyl.

19. The compound according to claim 16, wherein the compound is selected from:
    3-(6-methoxynaphthalen-2-yl)pyridine;
    3-(6-bromonaphthalen-2-yl)pyridine;
    3-(6-ethoxynaphthalen-2-yl)pyridine;
    3-(6-propoxynaphthalen-2-yl)pyridine;
    3-(6-benzyloxynaphthalen-2-yl)pyridine;
    3-(5-chloro-6-methoxynaphthalen-2-yl)pyridine;
    3-(5-bromo-6-methoxynaphthalen-2-yl)pyridine;
    3-(1,5-dichloro-6-methoxynaphthalen-2-yl)pyridine;
    3-(7-methoxynaphthalen-2-yl)pyridine; and
    3-(1-chloro-7-methoxynaphthalen-2-yl)pyridine.

20. A method of selectively inhibiting aldosterone synthase or steroid 11β-hydroxylase comprising, administering to a human a compound having a structure of formula (Ia)

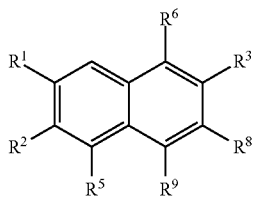

(Ia)

wherein $R^1$ or $R^2$ is hydrogen and the other of substituents $R^1$ or $R^2$ is selected from H and O—$C_{1-6}$ alkyl;
wherein $R^3$ is selected from oxazolyl, pyridyl, imidazolyl and pyrimidyl, which selection can be substituted with one $R^{12}$ residue;
wherein $R^5$ and $R^6$ are independently selected from H, fluorine, chlorine and bromine;
$R^8$ and $R^9$ are H;
and $R^{12}$ is selected from H, halogen, hydroxy, CN, $C_{1-3}$ alkyl and $C_{1-3}$ alkoxy;
or a pharmaceutically acceptable salt thereof.

21. The method according to claim 20, wherein the compound is chosen from:
    3-(6-methoxynaphthalen-2-yl)pyridine;
    3-(6-hydroxynaphthalen-2-yl)pyridine;
    3-(6-bromonaphthalen-2-yl)pyridine;
    3-(6-ethoxynaphthalen-2-yl)pyridine;
    3-(6-propoxynaphthalen-2-yl)pyridine;
    3-(6-benzyloxynaphthalen-2-yl)pyridine;
    3-(6-cyanonaphthalen-2-yl)pyridine;
    3-(5-chloro-6-methoxynaphthalen-2-yl)pyridine;
    3-(5-bromo-6-methoxynaphthalen-2-yl)pyridine;
    3-(1,5-dichloro-6-methoxynaphthalen-2-yl)pyridine;
    3-(7-methoxynaphthalen-2-yl)pyridine; and
    3-(1-chloro-7-methoxynaphthalen-2-yl)pyridine.

22. The method according to claim 20, wherein $R^3$ is selected from 3-pyridyl, 4-pyridyl, 1-imidazolyl, 4-imidazolyl, and 5-pyrimidyl.

23. The method according to claim 20, wherein $R^3$ is 3-pyridyl.

24. A pharmaceutical composition comprising a compound selected from:
    3-(6-cyanonaphthalen-2-yl)pyridine;
    3-[5-(pyridin-3-yl)-6-methoxynaphthalen-2-yl]pyridine;
    3-(3-methoxynaphthalen-2-yl)pyridine;
    methyl 6-(pyridin-3-yl)-2-naphthoate;
    6-(pyridin-3-yl)-2-naphthamide; and
    N-methyl-6-(pyridin-3-yl)-2-naphthamide.

25. A method of selectively inhibiting aldosterone synthase or steroid 11β-hydroxylase comprising, administering to a human a compound selected from:
    3-(1,5-dichloro-6-methoxynaphthalen-2-yl)pyridine;
    3-(3-methoxynaphthalen-2-yl)pyridine;
    methyl 6-(pyridin-3-yl)-2-naphthoate;
    6-(pyridin-3-yl)-2-naphthamide; and
    N-methyl-6-(pyridin-3-yl)-2-naphthamide.

\* \* \* \* \*